(12) United States Patent
Mostoslavsky et al.

(10) Patent No.: US 10,588,920 B2
(45) Date of Patent: Mar. 17, 2020

(54) AGENTS AND METHODS FOR TREATING PANCREATIC DUCTAL ADENOCARCINOMAS

(71) Applicant: The General Hospital Corporation, Boston, MA (US)

(72) Inventors: Raul Mostoslavsky, Boston, MA (US); Sita Kugel, Brookline, MA (US); Anders M. Naar, Arlington, MA (US)

(73) Assignee: The General Hospital Corporation, Boston, MA (US)

( * ) Notice: Subject to any disclaimer, the term of this patent is extended or adjusted under 35 U.S.C. 154(b) by 23 days.

(21) Appl. No.: 15/563,248

(22) PCT Filed: Mar. 31, 2016

(86) PCT No.: PCT/US2016/025134
§ 371 (c)(1),
(2) Date: Sep. 29, 2017

(87) PCT Pub. No.: WO2016/161058
PCT Pub. Date: Oct. 6, 2016

(65) Prior Publication Data
US 2018/0085389 A1 Mar. 29, 2018

Related U.S. Application Data

(60) Provisional application No. 62/141,317, filed on Apr. 1, 2015.

(51) Int. Cl.
| | | |
|---|---|---|
| *A61K 31/713* | (2006.01) | |
| *C12Q 1/6886* | (2018.01) | |
| *C12N 15/113* | (2010.01) | |
| *C12Q 1/34* | (2006.01) | |
| *G01N 33/574* | (2006.01) | |
| *G01N 33/50* | (2006.01) | |

(52) U.S. Cl.
CPC ........ *A61K 31/713* (2013.01); *C12N 15/1135* (2013.01); *C12Q 1/34* (2013.01); *C12Q 1/6886* (2013.01); *G01N 33/50* (2013.01); *G01N 33/57438* (2013.01); *G01N 33/57476* (2013.01); *C12Q 2600/106* (2013.01); *C12Q 2600/156* (2013.01); *G01N 2333/82* (2013.01); *G01N 2333/98* (2013.01)

(58) Field of Classification Search
None
See application file for complete search history.

(56) References Cited

U.S. PATENT DOCUMENTS

2010/0221266 A1  9/2010  Gregory et al.

OTHER PUBLICATIONS

Kugal et al., Cell, vol. 165:1401-1415, Jun. 2, 2016.*
Badea et al., "Combined gene expression analysis of whole-tissue and microdissected pancreatic ductal adenocarcinoma identifies genes specifically overexpressed in tumor epithelia," Hepato-Gastroenterology, 2008, 55: 2016-2027.
Barretina et al., "The Cancer Cell Line Encyclopedia enables predictive modelling of anticancer drug sensitivity," Nature, 2012, 483: 603-607.
Bell et al., "Insulin-like growth factor 2 mRNA-binding proteins (IGF2BPs): post-transcriptional drivers of cancer progression?," Cellular and Molecular Life Sciences, 2013, 70: 2657-2675.
Biankin et al., "Pancreatic cancer genomes reveal aberrations in axon guidance pathway genes," Nature, 2012, 491: 399-405.
Boyerinas et al., "Identification of let-7-regulated oncofetal genes," Cancer Research, 2008, 68: 2587-2591.
Bussing et al., "let-7 microRNAs in development, stem cells and cancer," Trends in Molecular Medicine, 2008, 14: 400-409.
Chang et al., "Lin-28B transactivation is necessary for Myc-mediated let-7 repression and proliferation," PNAS, 2009, 106: 3384-3389.
De Vries et al., "Prolonged Ezh2 Depletion in Glioblastoma Causes a Robust Switch in Cell Fate Resulting in Tumor Progression," Cell Reports, 2015, 10: 383-397.
Donner et al., "CDK8 is a stimulus-specific positive coregulator of p53 target genes," Molecular Cell, 2007, 27: 121-133.
Etchegaray et al., "The histone deacetylase SIRT6 controls embryonic stem cell fate via TET-mediated production of 5-ydroxymethylcytosine," Nature Cell Biology, May 2015, 17: 545-557.
Fitamant et al., "YAP Inhibition Restores Hepatocyte Differentiation in Advanced HCC, Leading to Tumor Regression," Cell Reports, 2015, 1692-1707.
Funato et al., "Use of human embryonic stem cells to model pediatric gliomas with H3.3K27M histone mutation," Science, 2014, 346: 1529-1533.
Furukawa et al., "Long-term culture and immortalization of epithelial cells from normal adult human pancreatic ducts transfected by the E6E7 gene of human papilloma virus 16," The American Journal of Pathology, Jun. 1996, 148: 1763-1770.
Hamilton and Aaltonen, World Health Organization Classification of Tumours. Pathology and Genetics of Tumours of the Digestive System, IARC Press, 2000, 314 pages.
Heo et al., "Lin28 mediates the terminal uridylation of let-7 precursor MicroRNA," Molecular Cell, 2008, 32: 276-284.
Iliopoulos et al., "An epigenetic switch involving NF-kappaB, Lin28, Let-7 MicroRNA, and IL6 links inflammation to cell transformation," Cell, 2009, 139: 693-706.
International Preliminary report on Patentability in International Application No. PCT/US16/25134, dated Oct. 12, 2017, 7 pages.
Jackson et al., "Analysis of lung tumor initiation and progression using conditional expression of oncogenic K-ras," Genes & Development, 2001, 15: 3243-3248.

(Continued)

*Primary Examiner* — Sean McGarry
(74) *Attorney, Agent, or Firm* — Fish & Richardson P.C.

(57) ABSTRACT

It has been discovered that NAD+-dependent histone deacetylase SIRT6 is critical for suppression of PDAC by controlling the expression of Lin28b, which is a negative regulator of let-7 microRNA. Specifically, SIRT6 loss results in histone hyperacetylation at the Lin28b promoter, Myc recruitment, and pronounced induction of Lin28b and downstream let-7 target genes, HMGA2, IGF2BP1, and IGF2BP3. This invention relates generally to agents and methods of reducing expression or activity of Lin28b to treat (aggressive) PDAC in a subject.

11 Claims, 40 Drawing Sheets

Specification includes a Sequence Listing.

(56) References Cited

OTHER PUBLICATIONS

Johnson et al., "RAS is regulated by the let-7 microRNA family," Cell, 2005, 120: 635-647.
Kawaguchi et al., "The role of the transcriptional regulator Ptf1a in converting intestinal to pancreatic progenitors," Nature Genetics, 2002, 32: 128-134.
King et al., "LIN28B promotes colon cancer progression and metastasis," Cancer Research, 2011, 71: 4260-4268.
Kugel et al., Identification of and Molecular Basis for SIRT6 Loss-of-Function Point Mutations in Cancer, Cell Reports, 2015, 13: 479-488.
Lei et al., "Determinants of mRNA recognition and translation regulation by Lin28," Nucleic Acids Res, 2012, 40: 3574-84.
Li and Durbin, "Fast and accurate short read alignment with Burrows-Wheeler transform," Bioinformatics, Jul. 2009, 25: 1754-1760.
Liang and Keles, "Detecting differential binding of transcription factors with ChIP-seq," Bioinformatics, 2012, 28: 121-122.
Lu et al., "Pluripotent factor lin-28 and its homologue lin-28b in epithelial ovarian cancer and their associations with disease outcomes and expression of let-7a and IGF-II," European Journal of Cancer, Aug. 2009, 45: 2212-2218.
Marino et al., "Induction of medulloblastomas in p53-null mutant mice by somatic inactivation of Rb in the external granular layer cells of the cerebellum," Genes & Development, 2000, 14: 994-1004.
Mayr et al., "Disrupting the pairing between let-7 and Hmga2 enhances oncogenic transformation," Science, 2007, 315: 1576-1579.
Mootha et al., "PGC-1alpha-responsive genes involved in oxidative phosphorylation are coordinately downregulated in human diabetes," Nature Genetics, 2003, 34: 267-273.
Moss and Tang, "Conservation of the heterochronic regulator Lin-28, its developmental expression and microRNA complementary sites," Developmental Biology, 2003, 258: 432-442.
Mostoslavsky et al., "Genomic instability and aging-like phenotype in the absence of mammalian SIRT6," Cell, 2006, 124: 315-329.
Newman et al., "Lin-28 interaction with the Let-7 precursor loop mediates regulated microRNA processing," RNA, 2008, 14: 1539-1549.
Nguyen et al., "Lin28b is sufficient to drive liver cancer and necessary for its maintenance in murine models," Cancer Cell, 2014, 26: 248-261.
Nielsen et al., "Sequential dimerization of human zipcode-binding protein IMP1 on RNA: a cooperative mechanism providing RNP stability," Nucleic Acids Research, 2004, 32: 4368-4376.
Noubissi et al., "CRD-BP mediates stabilization of betaTrCP1 and c-myc mRNA in response to beta-catenin signaling," Nature, 2006, 441: 898-901.
Park et al., "Let-7 prevents early cancer progression by suppressing expression of the embryonic gene HMGA2," Cell Cycle, 2007, 6: 2585-2590.
Pasquinelli et al., "Conservation of the sequence and temporal expression of let-7 heterochronic regulatory RNA," Nature, 2000 408: 86-89.
Pei et al., "FKBP51 affects cancer cell response to chemotherapy by negatively regulating Akt," Cancer Cell, 2009, 16: 259-266.
Perez-Mancera et al., "The deubiquitinase USP9X suppresses pancreatic ductal adenocarcinoma," Nature, 2012, 486: 266-270.
Piscuoglio et al., "HMGA1 and HMGA2 protein expression correlates with advanced tumour grade and lymph node metastasis in pancreatic adenocarcinoma," Histopathology, 2012, 60: 397-404.
Piskounova et al., "Determinants of microRNA processing inhibition by the developmentally regulated RNA-binding protein Lin28," The Journal of Biological Chemistry, 2008, 283: 21310-21314.
Polesskaya et al., "Lin-28 binds IGF-2 mRNA and participates in skeletal myogenesis by increasing translation efficiency," Genes & Development, 2007, 21: 1125-1138.
Robinson et al., "edgeR: a Bioconductor package for differential expression analysis of digital gene expression data," Bioinformatics, 2010, 26: 139-140.
Ryan et al., "Pancreatic adenocarcinoma," The New England Journal of Medicine, 2014, 371: 1039-1049.
Rybak et al., "A feedback loop comprising lin-28 and let-7 controls pre-let-7 maturation during neural stem-cell commitment," Nature Cell Biology, 2008, 10: 987-993.
Sampson et al., "MicroRNA let-7a down-regulates MYC and reverts MYC-induced growth in Burkitt lymphoma cells," Cancer Research, 2007, 67: 9762-9770.
Schaeffer et al., "Insulin-like growth factor 2 mRNA binding protein 3 (IGF2BP3) overexpression in pancreatic ductal adenocarcinoma correlates with poor survival," BMC Cancer, 2010, 10: 59.
Sebastian et al., "The histone deacetylase SIRT6 is a tumor suppressor that controls cancer metabolism," Cell, 2012, 151: 1185-1199.
Subramanian et al., "Gene set enrichment analysis: a knowledge-based approach for interpreting genome-wide expression profiles," PNAS, 2005, 102: 15545-15550.
Taniuchi et al., "IGF2BP3-mediated translation in cell protrusions promotes cell invasiveness and metastasis of pancreatic cancer," Oncotarget, 2014, 5, 6832-6845.
Thakur et al., "Gene expression profiles in primary pancreatic tumors and metastatic lesions of Ela-c-myc transgenic mice," Molecular Cancer, 2008, 7: 11.
Thornton and Gregory, "How does Lin28 let-7 control development and disease?," 2012, Trends in Cell Biology, 2012, 22: 474-482.
Viswanathan and Daley, Lin28: A microRNA regulator with a macro role. Cell, 2010, 140: 445-449.
Viswanathan et al., "Lin28 Enhances Tumorigenesis and is Associated With Advanced Human Malignancies," Nature Genetics, 2009, 41: 843-848.
Viswanathan et al., "Selective blockade of microRNA processing by Lin28," Science, 2008, 320: 97-100.
Waddell et al., "Whole genomes redefine the mutational landscape of pancreatic cancer," Nature, 2015, 518: 495-501.
Wagner et al., "Transgenic overexpression of the oncofetal RNA binding protein KOC leads to remodeling of the exocrine pancreas," Gastroenterology, 2009, 124: 1901-1914.
Wang et al., "miRExpress: analyzing high-throughput sequencing data for profiling microRNA expression," BMC Bioinformatics, 2009, 10: 328.
Yang and Moss, "Temporally regulated expression of Lin-28 in diverse tissues of the developing mouse," GEP, 2003, 3: 719-726.
Yantiss et al., "KOC (K homology domain containing protein overexpressed in cancer): a novel molecular marker that distinguishes between benign and malignant lesions of the pancreas," The American Journal of Surgical Pathology, 2005, 29: 188-195.
Ying et al., "Oncogenic Kras maintains pancreatic tumors through regulation of anabolic glucose metabolism," Cell, 2012, 149: 656-670.
Zhang et al., "DPEP1 inhibits tumor cell invasiveness, enhances chemosensitivity and predicts clinical outcome in pancreatic ductal adenocarcinoma," PloS one, 2012, 7: e31507.
Zhang et al., "Model-based analysis of ChIP-Seq (MACS)," Genome Biology, 2008, 9: R137.
Zhong et al., "The histone deacetylase Sirt6 regulates glucose homeostasis via Hif1alpha," Cell, 2010, 140: 280-293.
International Search Report and Written Opinion dated Aug. 26, 2016 in international application No. PCT/US16/25134, 15 pgs.
Bhutia et al., "Differential Processing of let-7 a Precursors Influences RRM2 Expression and Chemosensitivity in Pancreatic Cancer: Role of LIN-28 and SET Oncoprotein." PLOS ONE 8(1):: e53436, 13 pgs. (2013).
Wang et al., "Lin-28B expression promotes transformation and invasion in human hepatocellular carcinoma," Carcinogenesis 31(9): 1516-1522 (2010).

* cited by examiner

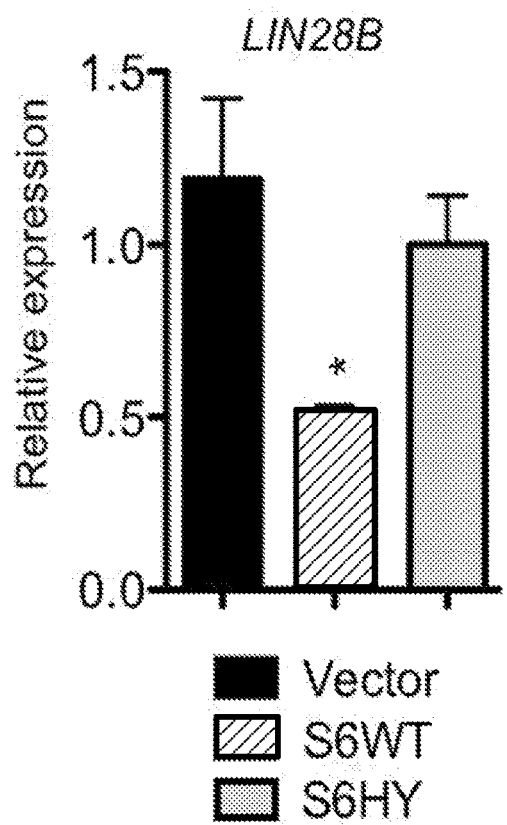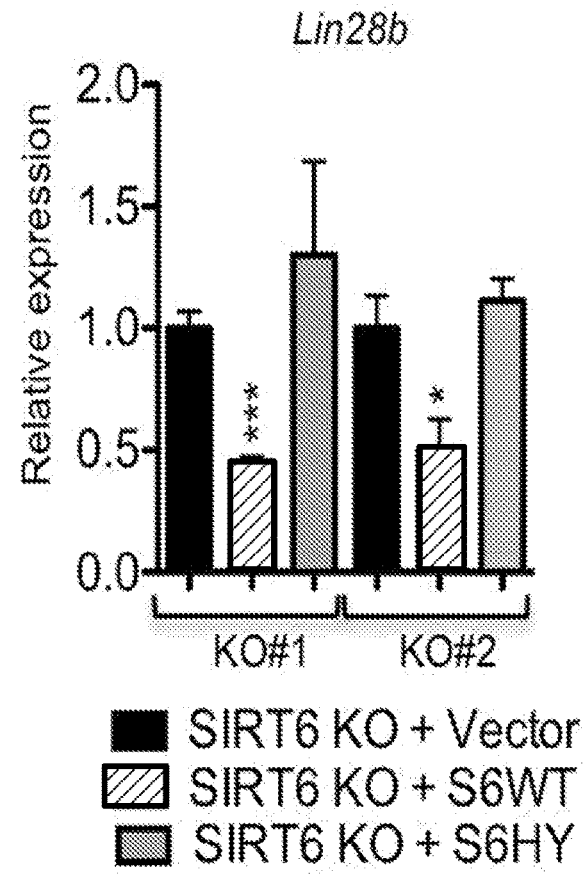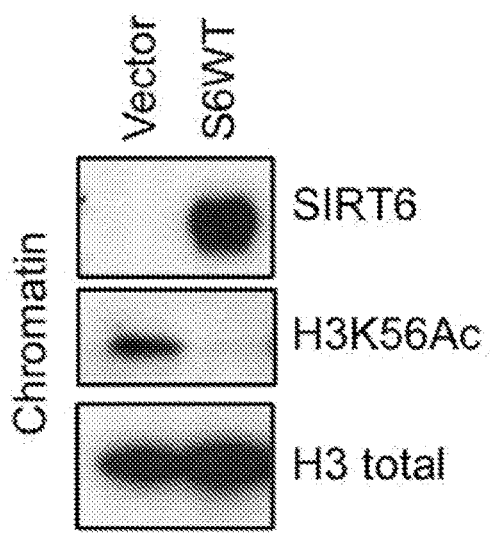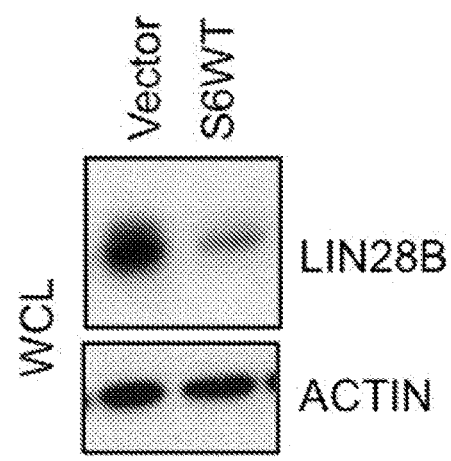
FIG. 3H
FIG. 3J
FIG. 3I

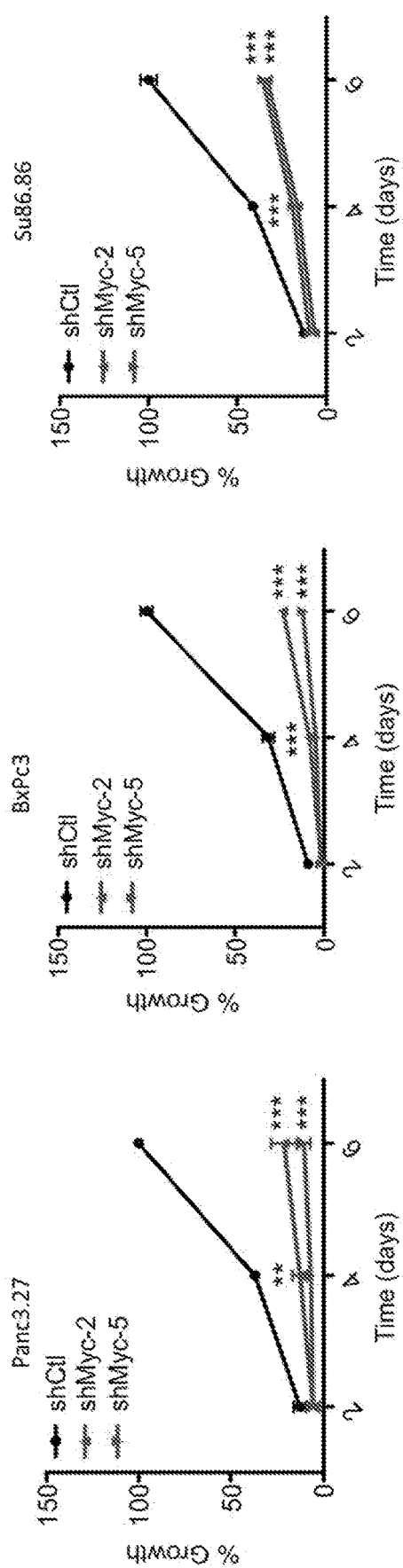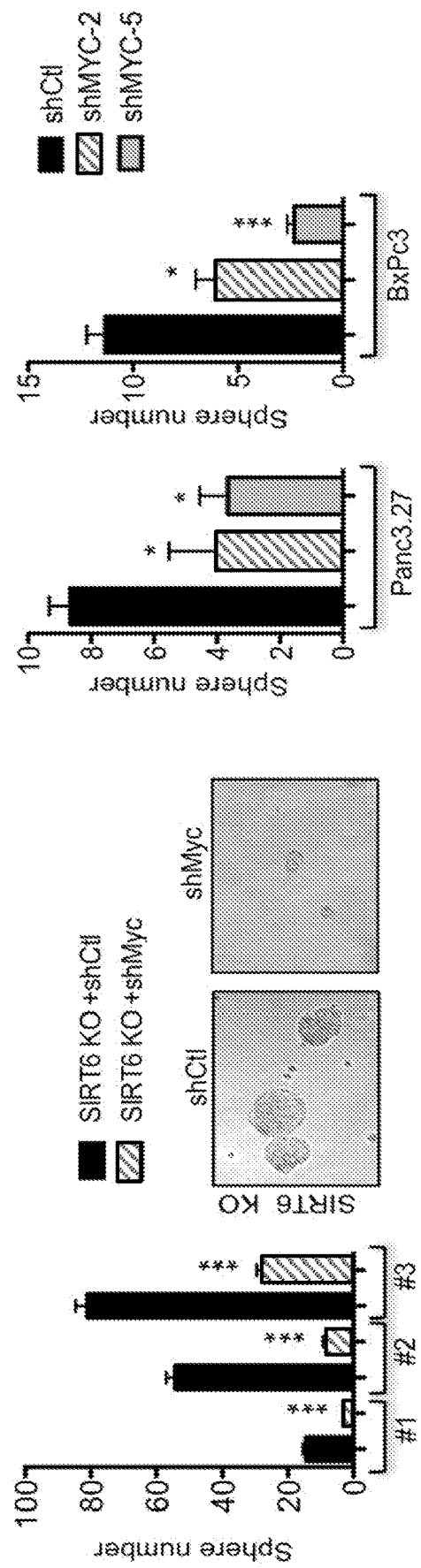
FIG. 4H
FIG. 4I
FIG. 4J

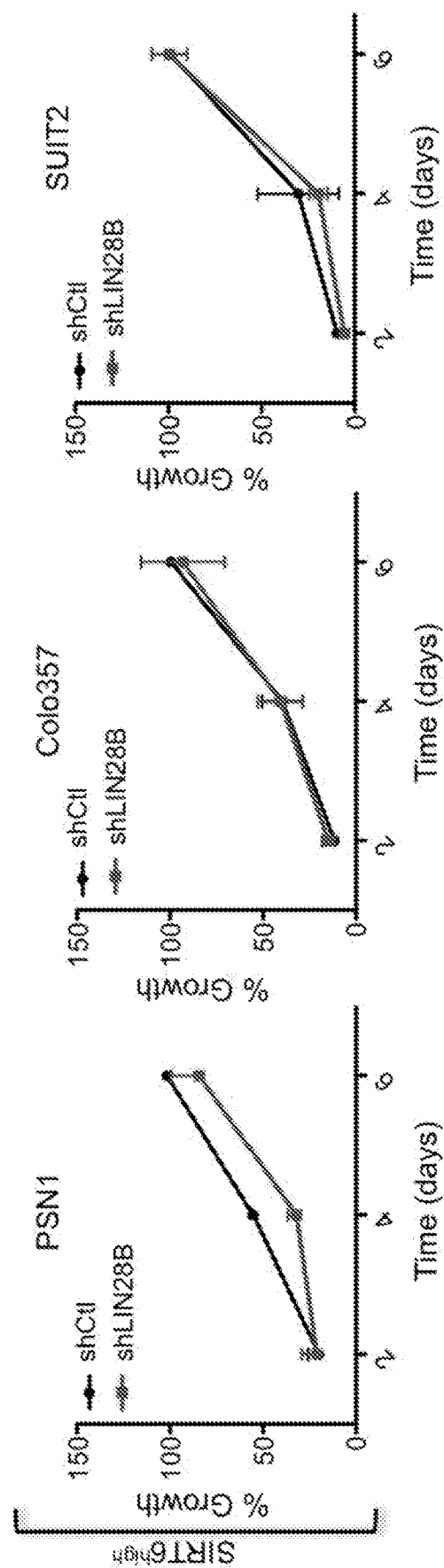
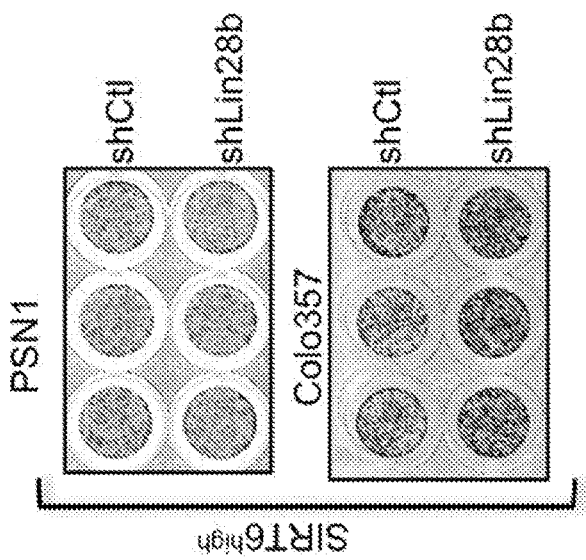
FIG. 5F
FIG. 5G

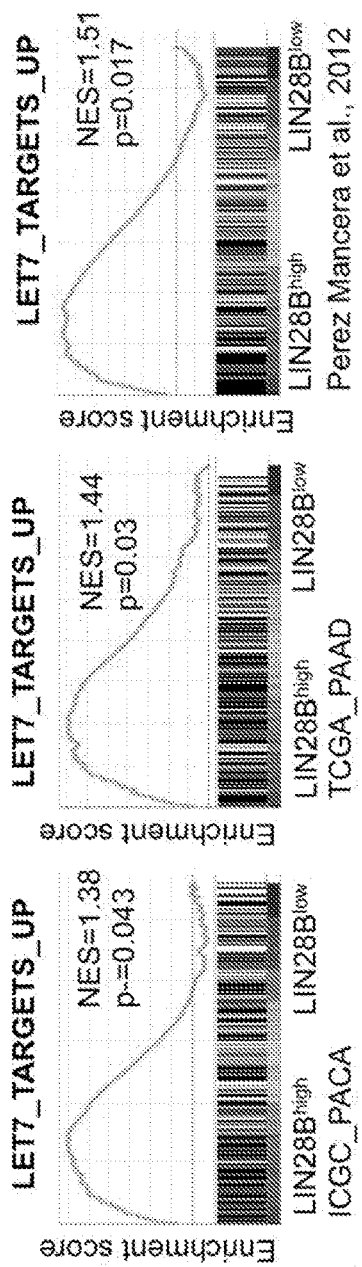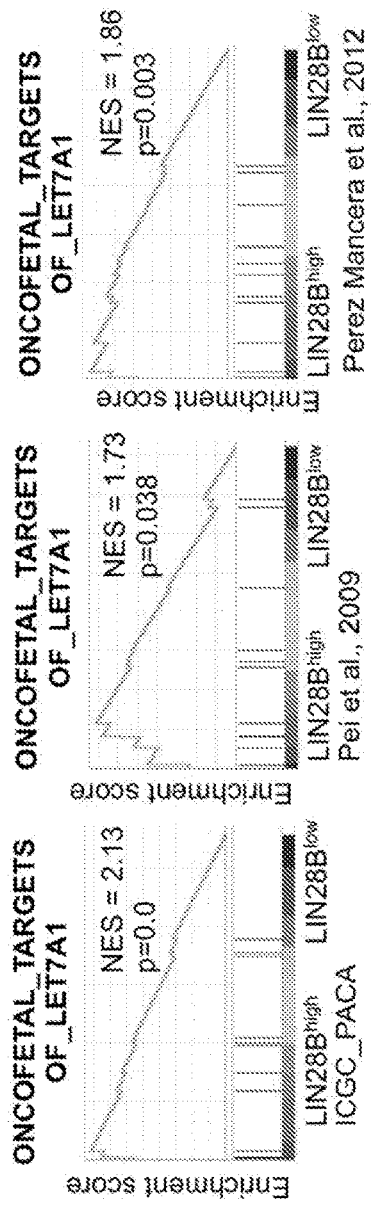

AGENTS AND METHODS FOR TREATING PANCREATIC DUCTAL ADENOCARCINOMAS

CROSS REFERENCE TO RELATED APPLICATION

This application is a U.S. National Phase Application under 35 U.S.C. § 371 of International Patent Application No. PCT/US2016/025134, filed on Mar. 31, 2016, which claims the benefit of U.S. Application No. 62/141,317, filed on Apr. 1, 2015, which is incorporated by reference in its entirety.

TECHNICAL FIELD

This invention relates to agents and methods for treating (aggressive) pancreatic ductal adenocarcinoma (PDAC).

BACKGROUND

Pancreatic ductal adenocarcinoma (PDAC) remains one of the most lethal of all human malignancies and is responsible for hundreds of thousands of deaths each year. Thus, there is an urgent need to improve our understanding of the molecular underpinnings that drive PDAC initiation, progression and metastasis and to leverage that understanding toward better therapeutic options. The current model proposes that a series of genetic alterations results in a stepwise progression through increasingly dysplastic precursor lesions, or pancreatic intraepithelial neoplasias (PanINs), toward invasive and finally metastatic PDAC. Initiating events identified in early PanIN lesions (PanIN I) include mutations and/or amplification in the KRAS oncogene and the loss of CDKN2A (p16INK4A) tumor suppressor gene, present in >90% and >50% of PDAC/PanINs, respectively (Ryan et al., 2014). Higher grade lesions (PanIN III) and invasive PDAC may accumulate additional genetic lesions, including inactivation of TP53 and TGFβ pathway components (SMAD4, TGFβR1, and TGFβR2), found in 60-70% and 50% of PDAC, respectively (Ryan et al., 2014). However, this fundamental model of PDAC pathogenesis, which is recapitulated in genetically engineered mice, has failed to identify either critical pathways that may be effectively targeted in the clinic or relevant molecular subsets for improved prognosis and stratification of patients toward a more effective therapy.

In addition to the above well-characterized genetic aberrations, it is becoming increasingly apparent that the dysregulation of epigenetic modifiers is central to the initiation and progression of human PDAC as well as many other tumors. Genomic deletions, mutations, and rearrangements recurrently targeting genes encoding components of the SWitch/Sucrose NonFermentable (SWI/SNF) chromatin remodeling complex, including all three putative DNA binding subunits (ARID1A, ARID1B, and PBRM1) and both enzymatic subunits (SMARCA2 and SMARC4), have been recently identified in at least 10-15% of PDAC cases. Additionally, mutations in the histone methyltransferase mixed-lineage leukemia protein 2 & 3 (MLL2 & MLL3) and the histone demethylase Kdm6a have been identified in 5-10% of PDAC (Ryan et al., 2014). However, since these chromatin-modifying enzymes may simultaneously regulate the transcription of thousands of genes by altering chromatin structure throughout the genome or may be involved in other cellular functions such as DNA repair and replication, the mechanisms by which these proteins control tumorigenesis have been difficult to elucidate. Specifically, whether these enzymes regulate an individual target gene or set of genes to drive survival, proliferation, cellular transformation, metabolic adaptations or invasive functions in PDAC is unknown; yet this understanding is critical to our ability to leverage data from the molecular profiling of human tumors to identify new therapeutic opportunities in molecularly-defined subsets of disease.

SUMMARY

This invention is based, at least in part, on the discovery that Sirtuin 6 (SIRT6) acts a potent tumor suppressor in genetically-engineered mouse models (GEMMs) of oncogenic Kras-driven PDAC, regardless of p53 status. Surprisingly, loss of SIRT6 did not accelerate PDAC tumorigenesis by enhancing aerobic glycolysis, as observed in colon cancer. Instead, loss of SIRT6 results in reactivation of the oncofetal protein Lin28b in both human and murine PDAC. Importantly, this de-repression results in the upregulation of numerous let-7 target genes and is critical for the survival of SIRT6-deficient PDAC. The SIRT6/Lin28b axis is a novel pathway in PDAC carcinogenesis and a molecularly defined subset that may benefit from therapeutic intervention.

In one aspect, the present disclosure features use of a Lin28b inhibitor for treating PDAC in a subject. In one aspect, the present disclosure provides methods of treating PDAC in a subject by administering a therapeutically effective amount of a Lin28b inhibitor to the subject.

In another aspect, the present disclosure features methods of diagnosing and optionally treating PDAC in a subject, wherein the methods include providing a sample comprising pancreatic cells from the subject; performing an assay to determine a level of Lin28b and/or SIRT6 expression in the sample; comparing the level of Lin28b and/or SIRT6 expression in the sample to a reference level of Lin28b and/or SIRT6 expression, respectively; identifying a subject who has a level of Lin28b expression in the sample above the reference level as having PDAC or having an increased risk of developing PDAC; identifying a subject who has a level of SIRT6 expression in the sample below the reference level as having PDAC or having an increased risk of developing PDAC; and optionally administering a treatment for PDAC to the identified subject who has a level of Lin28b expression in the sample that is above the reference level and/or to the identified subject who has a level of SIRT6 expression in the sample that is below the reference level, wherein the treatment comprises an inhibitory nucleic acid effective to specifically reduce expression of Lin28b. In some embodiment, the level of Lin28b and/or SIRT6 expression in the sample is determined by quantitative PCR, flow cytometry, or quantitative immunoassay.

The uses and methods are effective for a variety of subjects including mammals, e.g., humans and other animals, such as laboratory animals, e.g., mice, rats, rabbits, or monkeys, or domesticated and farm animals, e.g., cats, dogs, goats, sheep, pigs, cows, or horses.

In some embodiments, the Lin28b inhibitor can be an inhibitory nucleic acid effective to specifically reduce expression of Lin28b, e.g., a small interfering RNA molecule, antisense nucleic acid, locked nucleic acid (LNA) molecule, peptide nucleic acid (PNA) molecule, or ribozyme.

In some embodiments, the inhibitory nucleic acid is 5 to 40 bases in length (optionally 12-30, 12-28, or 12-25 bases in length). In one embodiment, the inhibitory nucleic acid has a sequence of 5'-GCCTTGAGTCAATACGGGTAA-3' (SEQ ID NO:3).

In some embodiments, the inhibitory nucleic acid is 10 to 50 bases in length.

In some embodiments, the inhibitory nucleic acid comprises a base sequence at least 90% complementary to at least 10 bases of the RNA sequence.

In some embodiments, the inhibitory nucleic acid comprises a sequence of bases at least 80% or 90% complementary to, e.g., at least 5-30, 10-30, 15-30, 20-30, 25-30 or 5-40, 10-40, 15-40, 20-40, 25-40, or 30-40 bases of the RNA sequence.

In some embodiments, the inhibitory nucleic acid comprises a sequence of bases with up to 3 mismatches (e.g., up to 1, or up to 2 mismatches) in complementary base pairing over 10, 15, 20, 25 or 30 bases of the RNA sequence.

In some embodiments, the inhibitory nucleic acid comprises a sequence of bases at least 80% complementary to at least 10 bases of the RNA sequence.

In some embodiments, the inhibitory nucleic acid comprises a sequence of bases with up to 3 mismatches over 15 bases of the RNA sequence.

In some embodiments, the inhibitory nucleic acid is single stranded.

In some embodiments, the inhibitory nucleic acid is double stranded.

In some embodiments, the inhibitory nucleic acid comprises one or more modifications comprising: a modified sugar moiety, a modified internucleoside linkage, a modified nucleotide and/or combinations thereof.

In some embodiments, the inhibitory nucleic acid is an antisense oligonucleotide, LNA molecule, PNA molecule, ribozyme or siRNA.

In some embodiments, the inhibitory nucleic acid is double stranded and comprises an overhang (optionally 2-6 bases in length) at one or both termini.

In some embodiments, the inhibitory nucleic acid is selected from the group consisting of antisense oligonucleotides, ribozymes, external guide sequence (EGS) oligonucleotides, siRNA compounds, micro RNAs (miRNAs); small, temporal RNAs (stRNA), and single- or double-stranded RNA interference (RNAi) compounds.

In some embodiments, the RNAi compound is selected from the group consisting of short interfering RNA (siRNA); or a short, hairpin RNA (shRNA); small RNA-induced gene activation (RNAa); and small activating RNAs (saRNAs).

In some embodiments, the antisense oligonucleotide is selected from the group consisting of antisense RNAs, antisense DNAs, and chimeric antisense oligonucleotides.

In some embodiments, the modified internucleoside linkage comprises at least one of: alkylphosphonate, phosphorothioate, phosphorodithioate, alkylphosphonothioate, phosphoramidate, carbamate, carbonate, phosphate triester, acetamidate, carboxymethyl ester, or combinations thereof.

In some embodiments, the modified sugar moiety comprises a 2'-O-methoxyethyl modified sugar moiety, a 2'-methoxy modified sugar moiety, a 2'-O-alkyl modified sugar moiety, or a bicyclic sugar moiety. In some embodiments, the inhibitory nucleic acids include 2'-OMe, 2'-F, LNA, PNA, FANA, ENA or morpholino modifications.

The invention provides several advantages. The prophylactic and therapeutic methods described herein using a Lin28b inhibitor are effective in treating PDAC and have minimal, if any, side effects.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. Other features, objects, and advantages of the invention will be apparent from the detailed description, and from the claims.

Figure 1A:
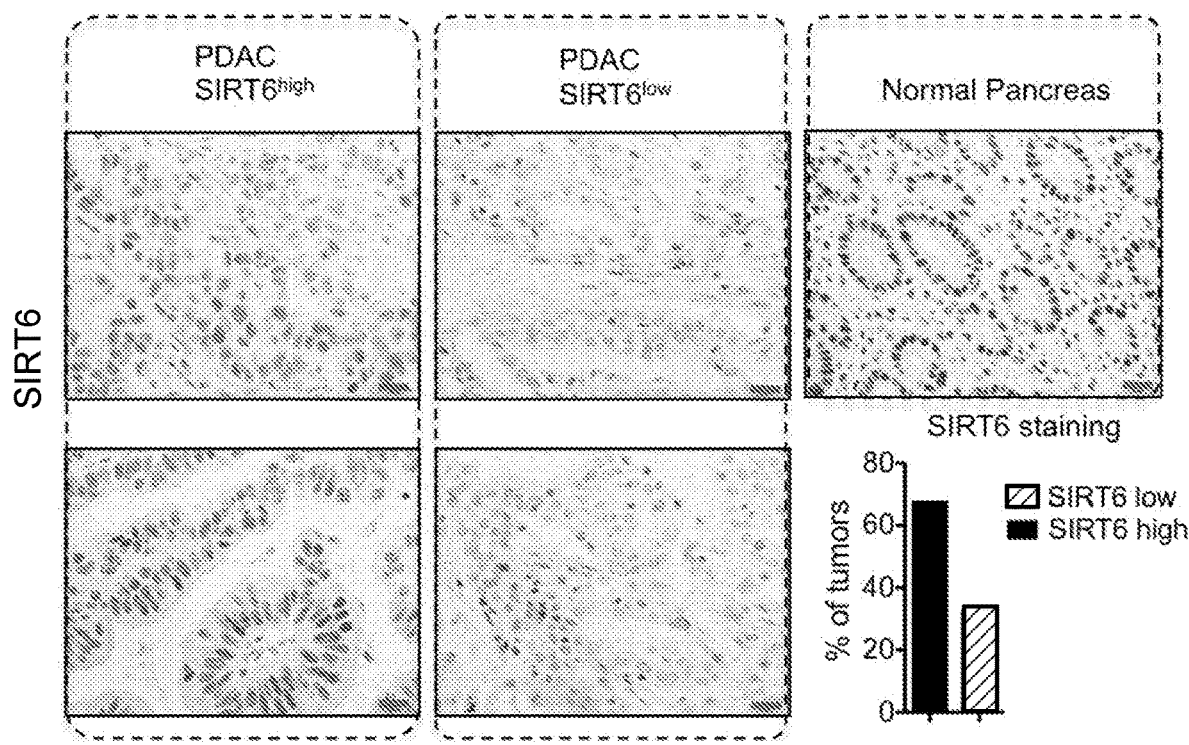
FIGS. 1A-1H are a panel of eight figures showing loss of SIRT6 cooperates with oncogenic Kras to accelerate PDAC. 1A, Immunohistochemistry of SIRT6 in human PDAC samples (left & center) compared to normal pancreas (right) and quantification of IHC scoring (bottom right). 1B, Kaplan-Meier analysis of the indicated PDAC patient samples based on SIRT6 IHC score (n=120). 1C, Kaplan-Meier analysis of the indicated GEMMs showing time until signs of illness necessitated euthanasia. All animals euthanized had pancreatic tumors. 1D, Necropsy of Sirt6$^{f/f}$; Kras$^{G12D}$; p53$^{f/+}$; p48-Cre (SIRT6 KO) GEMM euthanized at 13 weeks. Top left, Image of abdominal contents showing pancreatic mass and splenomegaly. Top middle, extracted SIRT6 KO tumor. Upper right, haematoxylin and eosin (H&E) staining showing PDAC histology. Bottom left, Gross image of liver with metastases. Bottom middle, H&E stain of liver metastasis. Bottom right, H&E stain of lung metastasis. 1E, Quantification of the number of metastases in the livers or the lungs of Sirt6$^{f/f}$; Kras$^{G12D}$; p53$^{f/+}$; p48-Cre and Sirt6$^{+/+}$; Kras$^{G12D}$; p53$^{f/+}$; p48-Cre GEMMs from the Kaplan-Meier analysis in FIG. 1C. 1F, Kaplan-Meier analysis of the indicated GEMMs showing time until signs of illness necessitated euthanasia. All animals euthanized had pancreatic tumors. 1G, Necropsy of Sirt6$^{f/f}$; Kras$^{G12D}$; p53$^{+/+}$ p48-Cre GEMM euthanized at 55 weeks. Top left, Image of abdominal contents showing pancreatic mass and splenomegaly. Top middle, extracted Sirt6$^{f/f}$; Kras$^{G12D}$; p53$^{+/+}$, p48-Cre pancreatic tumor with spleen attached. Upper right, haematoxylin and eosin (H&E) staining showing PDAC histology. Bottom left, H&E of liver metastasis. Bottom right, H&E stain of lung metastasis. 1H, Quantification of the number of metastases in the livers or the lungs of Sirt6$^{f/f}$; Kras$^{G12D}$; p53$^{+/+}$; p48-Cre and Sirt6$^{+/+}$; Kras$^{G12D}$; p53$^{+/+}$; p48-Cre GEMMs from the Kaplan-Meier analysis in FIG. 1F. Scale bars, black 50 μm, blue 20 μm. *p≤0.05; p≤0.01; *p≤0.001.

2G-2J, Panc3.27 and Panc-1 cells were engineered to express empty vector (vector), SIRT6 WT (S6WT), or SIRT6 HY (S6HY) catalytically inactive mutant under a doxycycline (Dox)-inducible system. 2G, Immunoblot of chromatin extract. 2H, Immunoblot of chromatin extract from Panc3.27 cells treated with dox for indicated times. The partial effect of S6HY on H3K56Ac levels after 4 days of overexpression likely relates to its partial catalytic activity. 2I, Proliferation was quantified by trypan blue exclusion assay. 2J, Photomicrographs (left) and quantification of Panc3.27 cells grown as in 2A. 2K-2M, HPDE cells were engineered to express empty vector (shCtl) and shSIRT6 under a doxycycline (Dox)-inducible system. 2K, (left) Immunoblot of whole cell lysate. 2L, Quantitative polymerase chain reaction with reverse transcription (qRTPCR) analysis of glycolytic genes. 2M, FDG-Glucose uptake in HPDE cells. 2N-2P, Panc3.27 and Panc-1 cells were engineered to express empty vector (vector), SIRT6 WT (S6WT), or SIRT6 HY (S6HY) catalytically inactive mutant under a doxycycline (Dox)-inducible system. 2N, Immunoblot of whole cell lysate. 2O, qRTPCR analysis of glycolytic genes. 2P, FDG-Glucose uptake in Panc3.27 cells after cells were treated with dox for the indicated times. *$p \leq 0.05$; $p \leq 0.01$; *$p \leq 0.001$.

FIGS. 3A-3J are a series of 10 figures showing that SIRT6 suppresses expression of the oncofetal protein Lin28b in human and murine PDAC. 3A, Venn diagram of gene promoters decorated by H3K56Ac in SIRT6 WT, SIRT6 KO, and SIRT6 KO PDAC cells engineered to express SIRT6 WT as determined by Chromatin immunoprecipitation (ChIP) sequencing (Seq). 3B, Integrative genomics viewer track of H3K56Ac levels along Lin28b promoter of the indicated murine PDAC cell lines. 3C, Expression of Lin28b in four independent SIRT6 WT and SIRT6 KO murine PDAC cell lines as measured by qRTPCR; data are presented as mean±s.e.m. between three independent experiments. 3D, Immunoblot of chromatin and whole cell lysates from individual SIRT6 WT and SIRT6 KO PDAC cell lines. 3E, 3F qRTPCR analysis for expression of LIN28B and SIRT6 in human PDAC cell lines displayed as a bar graph; data represent mean±s.e.m. between three independent experiments. (3E) and scatter plot (3F) demonstrating an inverse correlation. 3G, Immunohistochemistry of LIN28B and SIRT6 in human PDAC samples (left) compared to normal pancreas (right). 3H, 3I, LIN28B levels in Panc3.27 expressing empty vector, S6WT or the S6HY catalytically inactive mutant as measured by qRTPCR (3H) and immunoblot (3I). 3J, Lin28b levels in two independent SIRT6 KO murine PDAC cells lines expressing empty vector, S6WT or S6HY. Scale bars, black 50 μm, blue 20 μm. *$p \leq 0.05$; $p \leq 0.01$; *$p \leq 0.001$.

FIGS. 4A-4J are a series of 10 figures showing that SIRT6 co-represses Myc-driven transcription of Lin28b through histone deacetylation. 4A, Schematic representation of the human genomic region near the transcription start site of LIN28B. Putative Myc binding sites are indicated (CACGTG or CATGTG); both sites are conserved between human and mouse. 4B, 4C, ChIP of H3K56Ac (4B) and H3K9Ac (4C) marks followed by amplification of the regions surrounding the Myc binding sites in the LIN28B promoter. 4D, 4F, & 4I, Analysis of three independent SIRT6 KO murine PDAC cell lines expressing the either shMyc or control hairpins for expression of Myc (left) and Lin28b (right) by qRTPCR (4D), cell proliferation (4F), and tumor sphere forming ability (4I). 4E, 4G, 4H, & 4J, Analysis of three independent SIRT6$^{low}$ PDAC cell lines expressing the either shMyc or control hairpins for expression of MYC (left) and LIN28B (right) by qRTPCR (4E), immunoblot of MYC knockdown (4G), cell proliferation (4H), and tumor sphere forming ability (4J). For 4E, 4H, & 4J, data are represented as mean±std between triplicates. *$p \leq 0.05$; $p \leq 0.01$; *$p \leq 0.001$.

FIGS. 5A-5H are a panel of eight figures showing SIRT6$^{low}$ human PDAC cells are addicted to Lin28b. 5A-5H, Human PDAC cell lines with either high or low levels of SIRT6 expression were treated with shLIN28B versus a control hairpin. 5A, Immunoblot of whole cell lysate for SIRT6 and LIN28B. 5B, Number (left) and size (right) of tumor spheres grown under nonadherent conditions. 5C, Photo-micrographs of tumor spheres. 5D, 5F, Growth curve of SIRT6$^{low}$ (5D) and SIRT6$^{high}$ (5F) human PDAC cells, quantified by MTT assay. 5E, 5G, show visualization of day 6 results in SIRT6$^{low}$ (5E) and SIRT6$^{high}$ (G) human PDAC cells. 5H, Tumor weights of SIRT6$^{low}$ and SIRT6$^{high}$ PDAC lines grown as subcutaneous xenografts (n=5). *$p \leq 0.05$; $p \leq 0.01$; *$p \leq 0.001$.

FIGS. 6A-6H are a panel of eight figures showing Lin28b decreases let-7 levels and increases Igf2bp1/3 and Hmga2 levels in PDAC. 6A, Immunoblot of whole cell lysate and chromatin of human PDAC cell lines. SIRT6 and ACTIN have been reproduced from FIG. 2F for comparison. 6B-6E, SIRT6$^{low}$ and SIRT6$^{high}$ human PDAC cells treated with either shHMGA2 or control hairpin. Confirmation of HMGA2 knockdown by qRTPCR (6B), immunoblot (6C) growth curves of SIRT6$^{low}$ (Panc3.27, BxPc3 and Su86.86) and SIRT6$^{high}$ (COLO357) human PDAC cell lines (6D). Quantification of sphere diameter of SIRT6$^{low}$ (Panc3.27 and BxPc3) and SIRT6$^{high}$ (COLO357) human PDAC cell lines (left) and representative photo pictomicrographs (right) (6E). 6F-6H, SIRT6$^{low}$ and SIRT6$^{high}$ human PDAC cells treated with either shIGF2BP3 or control hairpins. Confirmation of IGF2BP3 knockdown by qRTPCR (6F), growth curves of SIRT6$^{low}$ (Panc3.27, BxPc3 and Su86.86) and SIRT6$^{high}$ (SUIT2) human PDAC cell lines (6G). Quantification of sphere diameter and number of SIRT6$^{low}$ (Panc3.27 and BxPc3) and SIRT6$^{high}$ (COLO357) human PDAC cell lines (left) and representative photo pictomicrographs (right) (6H). For 6B & 6D-6H, data are represented as mean±std between triplicates. *$p \leq 0.05$; $p \leq 0.01$; *$p \leq 0.001$.

FIGS. 7A-7G are a panel of seven figures showing that increased expression of LIN28B and let-7 target genes correlates with poor survival in PDAC. 7A, Kaplan-Meier analysis of the indicated PDAC patient samples based on LIN28B IHC score (n=120). 7B-7C, Gene set Enrichment Analysis (GSEA) plots showing that human PDAC tumors (7B) and PDAC cell lines from the Cancer Cell line Encyclopedia (CCLE) (7C) with high levels of LIN28B (LIN28B$^{high}$) overexpress many of the genes that are regulated by let-7. 7D, GSEA plots showing that human LIN28B$^{high}$ PDAC tumors overexpress targets of let-7 which are oncofetal genes. 7E, Correlation of HMGA2 and IGF2BP3 RNA expression in human PDAC samples from the TCGA pancreatic cancer dataset. 7F, Kaplan-Meier survival curves for HMGA2 (left) and IGF2BP3 (right) in human pancreatic cancer datasets from the TCGA. 7G, Model for SIRT6 loss in PDAC pathogenesis. *$p \leq 0.05$; $p \leq 0.01$; *$p \leq 0.001$.

DETAILED DESCRIPTION

PDAC is the most common malignancy of the pancreas. PDAC is an aggressive and difficult malignancy to treat. Complete surgical removal of the tumor remains the only chance for cure, however 80-90% of patients have disease that is surgically incurable at the time of clinical presentation. Despite advancing knowledge of the tumor biology of PDAC, improvement in diagnosis and management, and the rise of centers specialized in the care of patients with PDAC, the prognosis remains strikingly poor.

Alterations in epigenetic control are an important hallmark of cancer. Such alterations are thought to endow cells with the plasticity to override normal differentiation and growth control programs. Due to their poor vascularity and dense stroma, PDAC cells must acquire multiple metabolic adaptations to grow in a hypoperfused microenvironment. SIRT6 is an nicotinamide adenine dinucleotide (NAD)$^+$-dependent histone deacetylase which removes acetyl groups from histone 3 lysine 9 (H3K9) and histone 3 lysine 56 (H3K56) motifs and has pleiotropic functions including glucose homeostasis, maintenance of genome stability, and suppression of cellular transformation (Mostoslaysky et al., 2006; Sebastian et al., 2012; Zhong et al., 2010). These functions are exemplified in both Sirt6-deficient mice, which exhibit complete loss of subcutaneous fat and lethal hypoglycemia, as well as SIRT6-deficient cells, which show increased glucose uptake, enhanced glycolysis, anchorage independent growth and tumor formation in an in vivo model of colon cancer (Mostoslaysky et al., 2006; Sebastian et al., 2012). SIRT6 is downregulated in PDAC relative to normal tissue and loss of SIRT6 leads to dysregulation of the PDAC epigenome to drive its growth. By developing novel GEMMs, the present disclosure demonstrates that ablation of SIRT6 potently cooperates with activated Kras (which is mutated in >90% of human PDAC) to accelerate PDAC onset and promote metastasis. Mechanistically, loss of SIRT6 results in hyperacetylation of H3K9 and H3K56 at the promoter of the LIN28B gene, creating a more permissive chromatin state and allowing for the Myc transcription factor to drive its expression. This aberrant Lin28b expression is required for the growth of SIRT6-deficient tumor cells, thus identifying Lin28b as a novel oncogenic driver in this distinct subset, representing ~30-40% of human PDACs.

The Lin28/let-7 axis is now recognized as central to maintaining proper cell fate and coordinating proliferation, growth, and energy utilization at the cellular level as well as growth, developmental timing, tissue homeostasis and metabolism in whole organisms (Thornton and Gregory, 2012). While Lin28b is silenced during embryonic development (Moss and Tang, 2003; Rybak et al., 2008; Yang and Moss, 2003), it may be aberrantly reactivated in a variety of human cancers (Iliopoulos et al., 2009; Thornton and Gregory, 2012; Viswanathan et al., 2009) by mechanisms that remain poorly understood. Eight loss-of-function tumor-associated SIRT6 point mutations were recently identified, several of which specifically abrogated SIRT6 deacetylase activity, and many human cancer cell lines demonstrate copy number loss of the SIRT6 locus (Kugel et al., 2015).

Figure 7A:
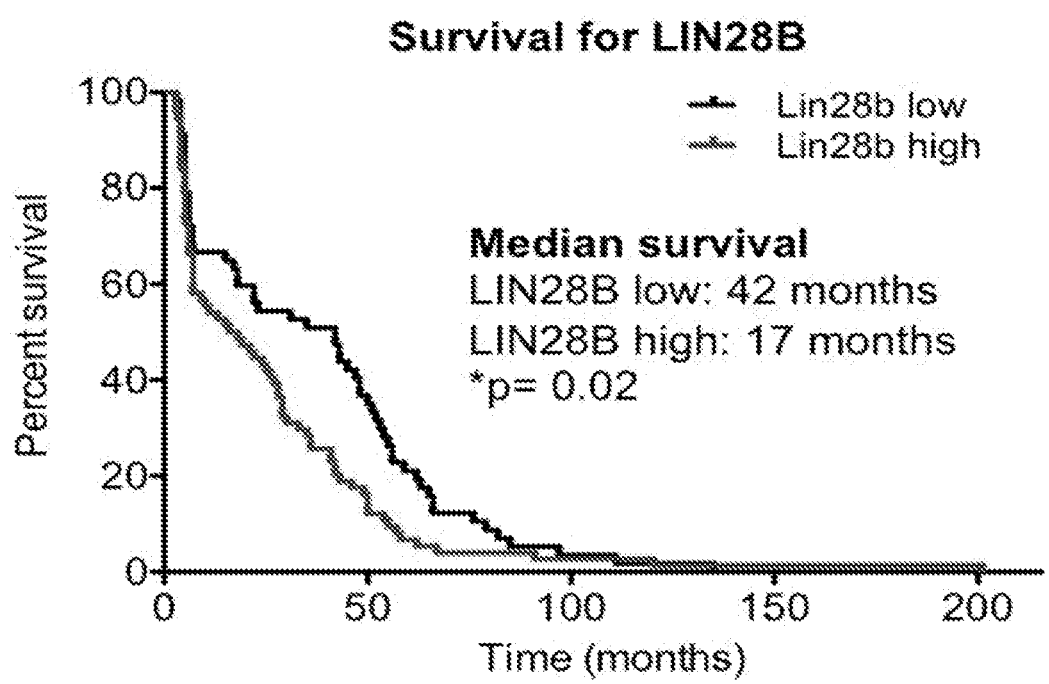
Figure 7E:
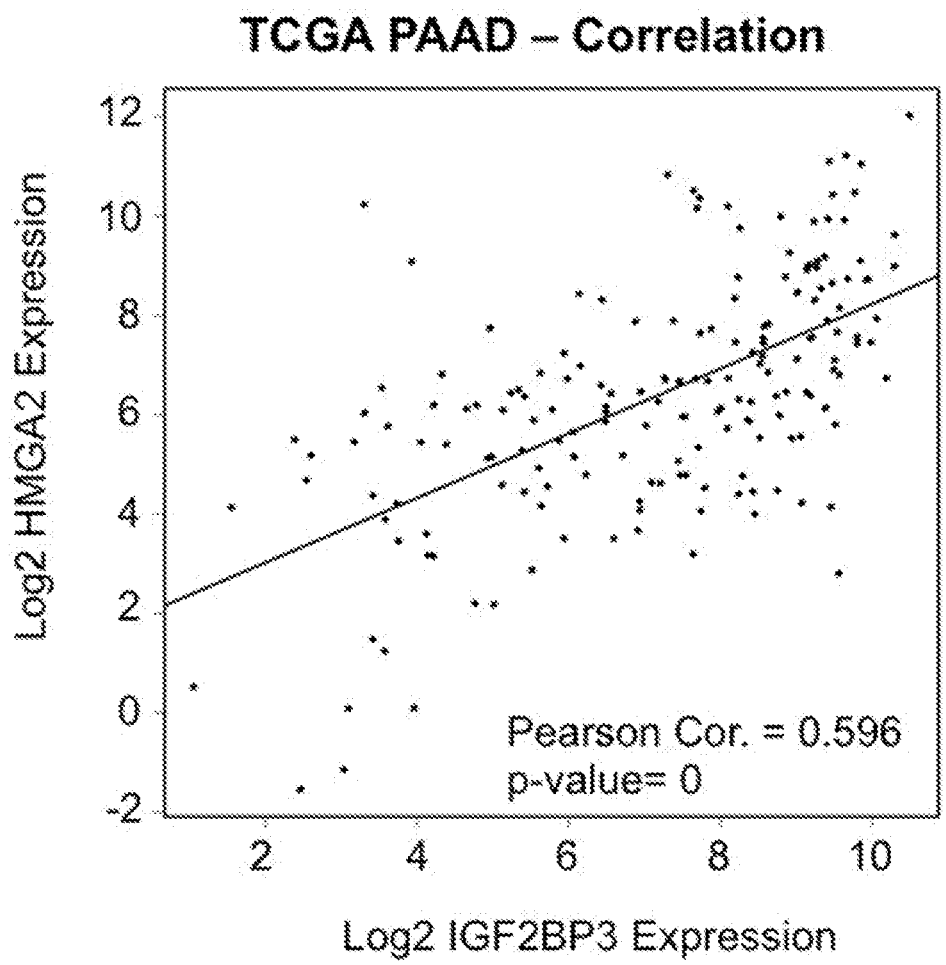
Figure 7F:
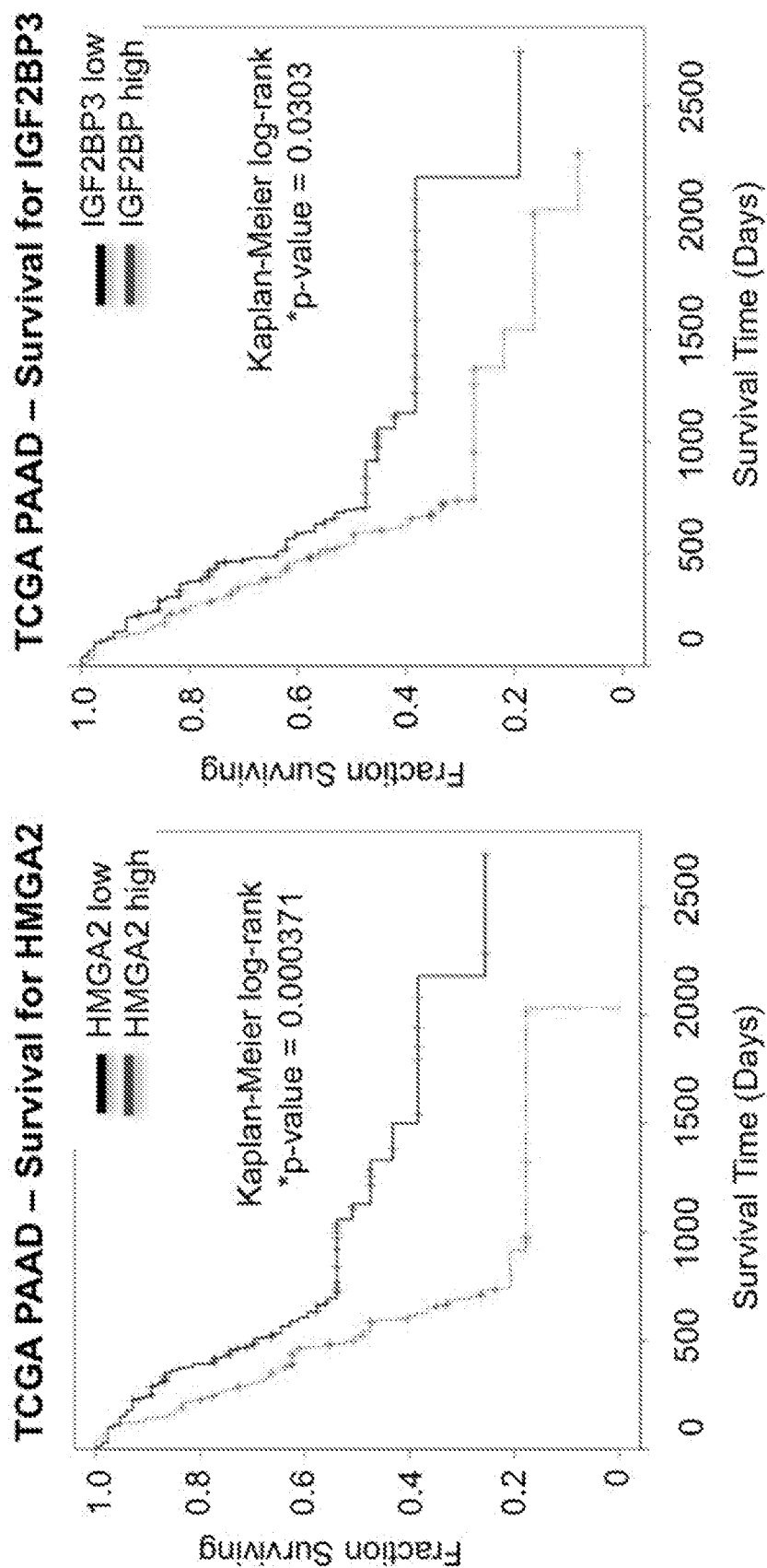
Figure 7G:
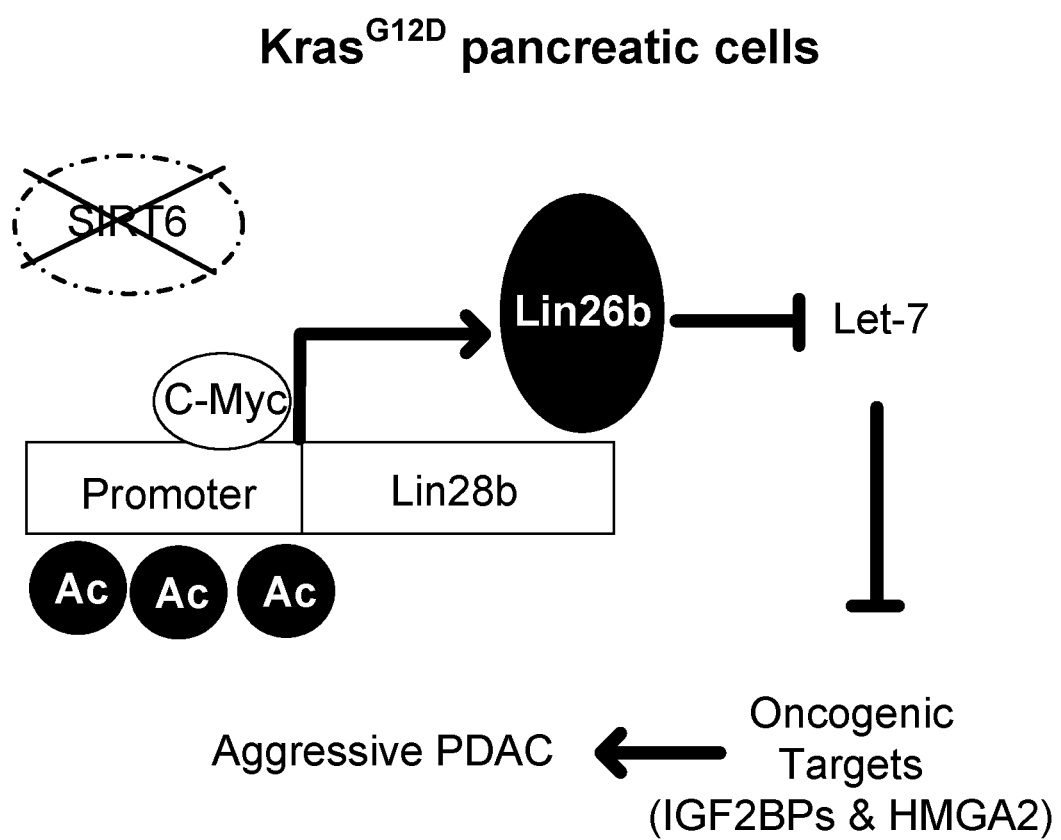

Given the critical roles for Lin28b in stem cell pluripotency, one can speculate that overexpression of oncofetal proteins reactivate programs of embryonic growth to promote a more "undifferentiated" and thereby aggressive form of pancreatic cancer. Consistently, upregulated genes downstream of Lin28b, includes the oncofetal RNA-binding proteins Igf2bp1 & 3 that have been associated with poorly differentiated PDAC. Expression of Igf2bps increase progressively with PDAC tumor stage (Yantiss et al., 2005) and high levels of Igf2bps in PDAC correlate with increased metastasis and extremely poor survival outcome (Schaeffer et al., 2010; Taniuchi et al., 2014). In this context, signs of accelerated initiation (increased number of PanIN) as well as increased metastatic potential were observed in mice expressing high levels of Lin28b and Igf2bps. Igf2bps also has functions in binding and stabilizing IGF2 and Myc transcripts, thus increasing their translation (Bell et al., 2013; Nielsen et al., 2004; Noubissi et al., 2006). Reinforcing Myc signaling and increasing IGF2 signaling could both serve to encourage proliferation and survival of PDAC cells. Strikingly, knockdown of Igf2bp3 in multiple independent SIRT6$^{low}$ and SIRT6 KO cell lines was sufficient to significantly inhibit their growth, while having no effect on the growth of SIRT6$^{high}$ and SIRT6 WT lines. Similarly, elevated protein expression of HMGA2 in PDAC has been associated with a more advanced tumor grade, epithelial to mesenchymal transition, and lymph node metastases, and this protein also promoted the growth of SIRT6$^{low}$ but not SIRT6$^{high}$ PDAC cells. Thus, Lin28b appears to drive the growth of SIRT6-deficient PDAC through the inhibition of multiple let-7 isoforms, resulting in a coordinated upregulation of a large number of Lin28b/let-7 target genes, including oncofetal proteins like IGF2BPs and HMGA2 (FIG. 7G).

There is evidence that reactivation of Lin28b may be the result of a more general mechanism that follows loss of epigenetic barriers. When human embryonic stem cells were used to model pediatric gliomas with H3.3K27M histone mutations, the gene that was reactivated to the highest extent in response to global H3K27 hypomethylation was LIN28B (Funato et al., 2014). Additionally, prolonged inhibition of the methyltransferase EZH2, in glioblastoma leads to upregulation of Lin28b expression (de Vries et al., 2015). EZH2 acts mainly through trimethylation of histone H3 lysine27, which is associated with transcriptional repression, thus loss of H3K27 trimethylation in two different contexts lead to upregulation of Lin28b expression. The activity of SIRT6 may provide a previously unrecognized epigenetic barrier, suppressing the expression of Lin28b specifically in PDAC. The H3K9 and H3K56 hyperacetylation of the Lin28b gene in response to SIRT6 loss may function to inhibit the reciprocal methylation of this histone residue, preventing H3K9Me3-mediated gene silencing, thereby licensing the aberrant re-expression of Lin28b to drive this fatal disease.

Novel therapeutic strategies for Kras-driven cancers such as PDAC have been limited by a failure to identify pathways that are specifically required in cancer cells but dispensable in normal tissues. Oncofetal proteins represent attractive targets for such strategies, as they are highly expressed in embryonic tissues but silenced in normal adult cells. Thus, the findings presented in the present disclosure highlight Lin28b as a novel oncogene in PDAC and identify a clinically-relevant and molecularly-defined subset of PDAC, which will benefit from novel therapeutic approaches aimed at targeting components of the Lin28b/let-7 pathway and provide new insights into the epigenetic mechanisms governing the reactivation of these developmental programs in cancer.

SIRT6 is a member of a highly conserved family of NAD$^+$-dependent deacetylases with various roles in metabolism, stress resistance, and life span. Seven examples of SIRT6 are highlighted below in Table 1. SIRT6-deficient mice develop normally but succumb to lethal hypoglycemia early in life. The present disclosure relates to the role of SIRT6 as a histone deacetylase to control the expression of LIN28b. Specifically, SIRT6 is critical for suppression of PDAC. SIRT6 inactivation accelerates PDAC progression and metastasis via upregulation of Lin28b, a negative regulator of the let-7 microRNA. SIRT6 loss results in histone hyperacetylation at the Lin28b promoter, Myc recruitment, and pronounced induction of Lin28b and downstream let-7 target genes, HMGA2, IGF2BP1, and IGF2BP3. This epigenetic program defines a distinct subset representing 30-40% of human PDAC, characterized by poor prognosis and an exquisite dependence on Lin28b for tumor growth. Thus, SIRT6 is an important PDAC tumor suppressor, and the Lin28b pathway acts as a therapeutic target in a molecularly-defined PDAC subset. Provided herein are methods for treating PDAC in a subject by administering to the subject a therapeutically effective amount of a Lin28b inhibitor, e.g., an inhibitory nucleic acid, e.g., a small interfering RNA molecule, antisense nucleic acid, LNA molecule, PNA molecule, and/or ribozyme.

TABLE 1

SIRT6 orthologs from seven different species along with their GenBank RefSeq Accession Numbers.

| Species | Nucleic Acid | Amino Acid | GeneID |
| --- | --- | --- | --- |
| Homo sapiens | NM_016539.1 | NP_057623.1 | 51548 |
| Mus musculus | NM_181586.3 | NP_853617.1 | 50721 |
| Rattus norvegicus | NM_001031649.1 | NP_001026819.1 | 299638 |
| Macaca mulatta | NC_007876.1 | NW_001106369.1 | 714545 |
| Pan troglodytes | NC_006486.2 | NW_001228145.1 | 737026 |
| Canis lupus familiaris | NC_006602.2 | NW_876272.1 | 485045 |
| Bos taurus | NM_001098084.1 | NP_001091553.1 | 535416 |

SIRT6 is a nuclear, chromatin-bound protein (Mostoslaysky et al., Cell 124:315-329, 2006). Among the sirtuins, SIRT6 deficiency causes the most striking phenotype. SIRT6 deficient mice are born normally, but at around 3 weeks of age they develop several acute degenerative processes, dying before one month of age. The defects include a severe metabolic imbalance, with low levels of serum IGF-1, complete loss of subcutaneous fat, lymphopenia, osteopenia, and acute onset of hypoglycemia, leading to death (Mostoslaysky et al., Cell 124:315-329, 2006). Furthermore, SIRT6 promotes resistance to DNA damage and oxidative stress, and suppresses genomic instability in mouse cells, in association with a role in base excision DNA repair (BER) (Mostoslaysky et al., Cell 124:315-329, 2006). Recent studies have demonstrated that SIRT6 is located at the telomeres in human cells, and knock-down of SIRT6 in those cells altered the telomere structure, causing accelerated senescence and telomere-dependent genomic instability.

Lin28b is an RNA-binding protein that regulates cell growth and differentiation (Lei et al., 2012). Developmental timing in Caenorhabditis elegans is regulated by a heterochronic gene pathway. The heterochronic gene LIN28 is a key regulator early in the pathway. LIN28 encodes an approximately 25-kDa protein with two RNA-binding motifs: a so-called "cold shock domain" (CSD) and a pair of retroviral-type CCHC zinc fingers; it is the only known animal protein with this motif pairing. The CSD is a β-barrel structure that binds single-stranded nucleic acids. LIN28 inhibits the biogenesis of a group of microRNAs (miRNAs), among which are the let-7 family miRNAs shown to participate in regulation of the expression of genes involved in cell growth and differentiation. LIN28 binds to the terminal loop region of pri/pre-let-7 and blocks their processing. miRNAs are small RNA molecules (21-23 nucleotides) that act as negative regulators of gene expression either by blocking mRNA translation into protein or through RNA interference. Seven examples of Lin28b are presented below in Table 2.

TABLE 2

Lin28b orthologs from seven different species along with their GenBank RefSeq Accession Numbers.

| Species | Nucleic Acid | Amino Acid | GeneID |
| --- | --- | --- | --- |
| Homo sapiens | NM_001004317.3 | NP_001004317.1 | 389421 |
| Mus musculus | NM_001031772.2 | NP_001026942.1 | 380669 |
| Gallus gallus | NM_001034818.1 | NP_001029990.1 | 421786 |
| Rattus norvegicus | XM_008773029.1 | XP_008771251.1 | 689054 |
| Macaca mulatta | XM_015137022.1 | XP_014992508.1 | 696130 |
| Pan troglodytes | XM_009451721.1 | XP_009449996.1 | 737588 |
| Canis lupus familiaris | XM_539064.5 | XP_539064.2 | 481943 |

As used herein, "substantially identical" refers to a nucleotide sequence that contains a sufficient or minimum number of identical or equivalent nucleotides to the sequence of SIRT6, such that homologous recombination can occur. For example, nucleotide sequences that are at least about 75% identical to the sequence of SIRT6 are defined herein as substantially identical. In some embodiments, the nucleotide sequences are about 80%, 85%, 90%, 95%, 99%, or 100% identical.

To determine the percent identity of two sequences, the sequences are aligned for optimal comparison purposes (gaps are introduced in one or both of a first and a second amino acid or nucleic acid sequence as required for optimal alignment, and non-homologous sequences can be disregarded for comparison purposes). The length of a reference sequence aligned for comparison purposes is at least 80% (in some embodiments, about 85%, 90%, 95%, or 100% of the length of the reference sequence) is aligned. The nucleotides or residues at corresponding positions are then compared. When a position in the first sequence is occupied by the same nucleotide or residue as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can be determined using the Needleman and Wunsch ((1970) J. Mol. Biol. 48:444-453) algorithm which has been incorporated into the GAP program in the GCG software package, using a Blossum 62 scoring matrix with a gap penalty of 12, a gap extend penalty of 4, and a frameshift gap penalty of 5.

Methods of Diagnosing or Predicting Risk Based on SIRT6 and/or Lin28b Expression Included herein are methods for diagnosing and predicting risk of developing PDAC, or providing a prognosis for a subject who has PDAC. The methods include obtaining a sample comprising (e.g., enriched in) pancreatic cells from a subject, and evaluating the presence and/or level of SIRT6 and Lin28b in the sample, and comparing the presence and/or level with one or more reference levels. The presence and/or level of SIRT6 and Lin28b can be evaluated using methods known in the art, e.g., using quantitative immunoassay methods, ELISA, enzymatic assays, flow cytometry with or without cell permeabilization, spectrophotometry, colorimetry, fluorometry, bacterial assays, liquid chromatography, gas chromatography, mass spectrometry, gas chromatography-mass spectrometry (GC-MS), liquid chromatography-mass spectrometry (LC-MS), LC-MS/MS, tandem MS, high pressure liquid chromatography (HPLC), HPLC-MS, and nuclear magnetic resonance spectroscopy, or other known techniques for determining the presence and/or quantity of a protein. The presence and/or level of a nucleic acid can be evaluated using methods known in the art, e.g., using quantitative PCR methods. In some embodiments, high throughput methods, e.g., protein or gene chips as are known in the art (see, e.g., Ch. 12, Genomics, in Griffiths et al., Eds. *Modern genetic Analysis,* 1999, W. H. Freeman and Company; Ekins and Chu, Trends in Biotechnology, 1999, 17:217-218; MacBeath and Schreiber, Science 2000, 289 (5485): 1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect the presence and/or level of Lin28b in a sample.

In some embodiments, the presence and/or level of SIRT6 and Lin28b is comparable to the presence and/or level of the protein in the disease reference, and the subject has one or more symptoms associated with PDAC, e.g., with aggressive PDAC, then the subject is diagnosed with (aggressive) PDAC. Skilled practitioners will recognize that aggressive PDACs can exhibit early onset of liver metastases and/or rapid general deterioration of the patient (i.e., cachexia). PDACs in general are very aggressive tumors, with most PDAC patients (~90%) dying within one year of diagnosis. In some embodiments, the subject has no overt signs or symptoms of PDAC, but the presence and/or level of SIRT6 and/or Lin28b evaluated is comparable to the presence and/or level of SIRT6 and Lin28b in the disease reference, then the subject has an increased risk of developing (aggressive) PDAC.

Suitable reference values can be determined using methods known in the art, e.g., using standard clinical trial methodology and statistical analysis. The reference values can have any relevant form. In some cases, the reference comprises a predetermined value for a meaningful level of SIRT6 and Lin28b, e.g., a control reference level that represents a normal level of SIRT6 and Lin28b, e.g., a level in an unaffected subject or a subject who is not at risk of developing PDAC, and/or a disease reference that represents a level of SIRT6 and Lin28b associated with (aggressive) PDAC.

The predetermined level can be a single cut-off (threshold) value, such as a median or mean, or a level that defines the boundaries of an upper or lower quartile, tertile, or other segment of a clinical trial population that is determined to be statistically different from the other segments. It can be a range of cut-off (or threshold) values, such as a confidence interval. It can be established based upon comparative groups, such as where association with risk of developing PDAC or presence of PDAC in one defined group is a fold higher, or lower, (e.g., approximately 2-fold, 4-fold, 8-fold, 16-fold or more) than the risk or presence of PDAC in another defined group. It can be a range, for example, where a population of subjects (e.g., control subjects) is divided equally (or unequally) into groups, such as a low-risk group, a medium-risk group and a high-risk group, or into quartiles, the lowest quartile being subjects with the lowest risk and the highest quartile being subjects with the highest risk, or into n-quantiles (i.e., n regularly spaced intervals) the lowest of the n-quantiles being subjects with the lowest risk and the highest of the n-quantiles being subjects with the highest risk.

In some embodiments, the predetermined level is a level or occurrence in the same subject, e.g., at a different time point, e.g., an earlier time point.

Subjects associated with predetermined values are typically referred to as reference subjects. For example, in some embodiments, a control reference subject does not have (aggressive) PDAC. In some cases it may be desirable that the control subject has (aggressive) PDAC. A disease reference subject is one who has or has an increased risk of developing (aggressive) PDAC. An increased risk is defined as a risk above the risk of subjects in the general population.

Thus, in some cases, the level of Lin28b in a subject being greater than or equal to a reference level of Lin28b is indicative of PDAC or aggressive PDAC. In other cases, the level of Lin28b in a subject being less than or equal to the reference level of Lin28b is indicative of the absence of disease or normal risk of PDAC. In some embodiments, the amount by which the level in the subject is the greater than the reference level is sufficient to distinguish a subject from a control subject, and optionally is a statistically significantly greater than the level in a control subject. In cases where the level of Lin28b in a subject being equal to the reference level of Lin28b, the "being equal" refers to being approximately equal (e.g., not statistically different).

In some cases, the level of SIRT6 in a subject being less than or equal to a reference level of SIRT6 is indicative of PDAC or aggressive PDAC. In other cases, the level of SIRT6 in a subject being greater than or equal to the reference level of SIRT6 is indicative of the absence of disease or normal risk of PDAC. In some embodiments, the amount by which the level in the subject is the greater than the reference level is sufficient to distinguish a subject from a control subject, and optionally is a statistically significantly greater than the level in a control subject. In cases where the level of SIRT6 in a subject being equal to the reference level of Lin28b, the "being equal" refers to being approximately equal (e.g., not statistically different).

The predetermined value can depend upon the particular population of subjects (e.g., human subjects) selected. For example, an apparently healthy population will have a different 'normal' range of levels of Lin28b than will a population of subjects which have, or are likely to have, PDAC. Accordingly, the predetermined values selected may take into account the category (e.g., sex, age, health, risk, presence of other diseases) in which a subject (e.g., human subject) falls. Appropriate ranges and categories can be selected with no more than routine experimentation by those of ordinary skill in the art.

In characterizing likelihood, or risk, numerous predetermined values can be established.

The methods described herein are useful for diagnosing and/or treating PDAC, e.g., aggressive PDAC. In some embodiments, once it has been determined that a person has PDAC, or has an increased risk of developing PDAC, then a treatment, e.g., an inhibitory nucleic acid as described herein, can optionally be administered.

Subjects to be Treated

In one aspect of the methods described herein, a subject is selected on the basis that they have, or are at risk of developing, (aggressive) PDAC, e.g., a subject with a level of SIRT6 expression below a reference level and/or a level of Lin28b expression above a reference level. PDAC develops from cells lining the ducts that carry the digestive juices into the main pancreatic duct and then on into the duodenum. They can grow anywhere in the pancreas, although most often they are found in the head of the pancreas. There are several very rare variants of PDAC, including adenosquamous carcinoma and colloid carcinoma.

A subject that has, or is at risk of developing, (aggressive) PDAC is one having one or more symptoms of the condition. Symptoms of (aggressive) PDAC are known to those of skill in the art and include, without limitation, abdominal pain, jaundice, weight loss, bowel problems, e.g., steatorrhea and diarrhea, nausea, vomiting, indigestion, heartburn, fever, shivering, diabetes, back pain, extreme tiredness/fatigue, feeling unusually full after food, venous thromboembolism, and unexplained acute pancreatitis. There is evidence that age, smoking, being overweight, a family history of pancreatic cancer, pancreatitis, diabetes, alcohol, red and processed meat, history of cancer, blood group A, hepatitis, stomach or gall bladder surgery, and *Helicobacter pylori* infection may increase risk of pancreatic cancer.

The methods are effective for a variety of subjects including mammals, e.g., humans and other animals, such as laboratory animals, e.g., mice, rats, rabbits, or monkeys, or domesticated and farm animals, e.g., cats, dogs, goats, sheep, pigs, cows, or horses.

Methods of Modulating Gene Expression

The methods described herein can be used for modulating expression of oncogenes and tumor suppressors in cells, e.g., PDAC cells. For example, to decrease expression of LIN28B in a cell, the methods include introducing into the cell an inhibitory nucleic acid or small molecule that specifically binds, or is complementary, to LIN28B mRNA.

In preferred embodiments, the inhibitory nucleic acid binds to a region within or near (e.g., within 100, 200, 300, 400, 500, 600, 700, 1K, 2K, or 5K bases of) LIN28B. A nucleic acid that binds "specifically" binds primarily to the target LIN28B RNA to inhibit Lin28b but not of other non-target RNAs. The specificity of the nucleic acid interaction thus refers to its function (e.g., inhibiting Lin28b gene expression) rather than its hybridization capacity. Inhibitory nucleic acids may exhibit nonspecific binding to other sites in the genome or other RNAs, without interfering with binding of other regulatory proteins and without causing degradation of the non-specifically-bound RNA. Thus, this nonspecific binding does not significantly affect function of other non-target RNAs and results in no significant adverse effects.

These methods can be used to treat (aggressive) PDAC in a subject by administering to the subject a composition (e.g., as described herein) comprising an LIN28B-inhibitory nucleic acid.

As used herein, treating includes "prophylactic treatment," which means reducing the incidence of or preventing (or reducing risk of) a sign or symptom of PDAC in a patient at risk for the disease, and "therapeutic treatment," which means reducing signs or symptoms of PDAC, reducing progression of PDAC, reducing severity of PDAC, in a patient diagnosed with PDAC, e.g., inhibiting tumor cell proliferation, increasing tumor cell death or killing, inhibiting rate of tumor cell growth or metastasis, reducing size of tumors, reducing number of tumors, reducing number of metastases, increasing 1-year or 5-year survival rate.

As used herein, the terms "cancer", "hyperproliferative", and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The term "carcinoma" is art recognized and refers to malignancies of epithelial or endocrine tissues including those forming from tissue of the pancreas. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

In some embodiments, the methods described herein include administering a composition, e.g., a sterile composition, comprising an inhibitory nucleic acid that is complementary to LIN28B. Inhibitory nucleic acids for use in practicing the methods described herein can be an antisense or small interfering RNA, including but not limited to a shRNA or siRNA. In some embodiments, the inhibitory nucleic acid is a modified nucleic acid polymer (e.g., a locked nucleic acid (LNA) molecule). Inhibitory nucleic acids have been employed as therapeutic moieties in the treatment of disease states in animals, including humans. Inhibitory nucleic acids can be useful therapeutic modalities that can be configured to be useful in treatment regimens for the treatment of cells, tissues, and animals, especially humans.

For therapeutics, an animal, preferably a human, suspected of having (aggressive) PDAC is treated by administering an inhibitory nucleic acid in accordance with this invention. For example, in one non-limiting embodiment, the methods comprise a step of administering to the animal in need of treatment, a therapeutically effective amount of an inhibitory nucleic acid as described herein.

Inhibitory Nucleic Acids

Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, molecules comprising modified bases, locked nucleic acid molecules (LNA molecules), antagomirs, peptide nucleic acid molecules (PNA molecules), and other oligomeric compounds or oligonucleotide mimetics which hybridize to at least a portion of the target nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, e.g., WO 2010040112.

In the present methods, the inhibitory nucleic acids are preferably designed to target LIN28B. These "inhibitory" nucleic acids are believed to work by inhibiting expression of LIN28B.

In some embodiments, the inhibitory nucleic acids are 10 to 50, 13 to 50, or 13 to 30 nucleotides in length. One having ordinary skill in the art will appreciate that this embodies oligonucleotides having antisense (complementary) portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. It is understood that non-complementary bases may be included in such inhibitory nucleic acids; for example, an inhibitory nucleic acid 30 nucleotides in length may have a portion of 15 bases that is complementary to the targeted RNA. In some embodiments, the oligonucleotides are 15 nucleotides in length. In some embodiments, the antisense or oligonucleotide compounds of the invention are 12 or 13 to 30 nucleotides in length. One having ordinary skill in the art will appreciate that this embodies inhibitory nucleic acids having antisense (complementary) portions of 12, 13, 14, 15, 16, 17, 18, 19, 20, 21, 22, 23, 24, 25, 26, 27, 28, 29, or 30 nucleotides in length, or any range therewithin.

Preferably, the inhibitory nucleic acid comprises one or more modifications comprising: a modified sugar moiety, and/or a modified internucleoside linkage, and/or a modified nucleotide and/or combinations thereof. It is not necessary for all positions in a given oligonucleotide to be uniformly modified, and in fact more than one of the modifications described herein may be incorporated in a single oligonucleotide or even at within a single nucleoside within an oligonucleotide.

In some embodiments, the inhibitory nucleic acids are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides, and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5, 220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, $CH_2$—N($CH_3$)—O—$CH_2$ (known as a methylene(methylimino) or MMI backbone, $CH_2$—O—N($CH_3$)—$CH_2$, $CH_2$—N ($CH_3$)—N ($CH_3$)—$CH_2$ and O—N($CH_3$)—$CH_2$—$CH_2$ backbones, wherein the native phosphodiester backbone is represented as O—P—O—$CH_2$); amide backbones (see De Mesmaeker et al. Acc. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5, 177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506. In some embodiments, the morpholino-based oligomeric compound is a phosphorodiamidate morpholino oligomer (PMO) (e.g., as described in Iverson, Curr. Opin. Mol. Ther., 3:235-238, 2001; and Wang et al., J. Gene Med., 12:354-364, 2010; the disclosures of which are incorporated herein by reference in their entireties.

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and CH2 component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

Modified oligonucleotides are also known that include oligonucleotides that are based on or constructed from arabinonucleotide or modified arabinonucleotide residues. Arabinonucleosides are stereoisomers of ribonucleosides, differing only in the configuration at the 2'-position of the sugar ring. In some embodiments, a 2'-arabino modification is 2'-F arabino. In some embodiments, the modified oligonucleotide is 2'-fluoro-D-arabinonucleic acid (FANA) (as described in, for example, Lon et al., Biochem., 41:3457-3467, 2002 and Min et al., Bioorg. Med. Chem. Lett., 12:2651-2654, 2002; the disclosures of which are incorporated herein by reference in their entireties). Similar modifications can also be made at other positions on the sugar, particularly the 3' position of the sugar on a 3' terminal nucleoside or in 2'-5' linked oligonucleotides and the 5' position of 5' terminal nucleotide.

PCT Publication No. WO 99/67378 discloses arabinonucleic acids (ANA) oligomers and their analogues for improved sequence specific inhibition of gene expression via association to complementary messenger RNA.

Other preferred modifications include ethylene-bridged nucleic acids (ENAs) (e.g., International Patent Publication No. WO 2005/042777, Morita et al., Nucleic Acid Res., Suppl 1:241-242, 2001; Surono et al., Hum. Gene Ther., 15:749-757, 2004; Koizumi, Curr. Opin. Mol. Ther., 8:144-149, 2006 and Horie et al., Nucleic Acids Symp. Ser (Oxf), 49:171-172, 2005; the disclosures of which are incorporated herein by reference in their entireties). Preferred ENAs include, but are not limited to, 2'-O,4'-C-ethylene-bridged nucleic acids.

Examples of LNAs are described in WO 2008/043753 and include compounds of the following formula.

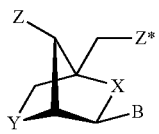

where X and Y are independently selected among the groups —O—,
—S—, —N(H)—, N(R)—, —CH2- or —CH— (if part of a double bond),
—CH$_2$—O—, —CH$_2$—S—, —CH$_2$—N(H)—, —CH$_2$—N(R)—, —CH$_2$—CH$_2$— or —CH$_2$—CH— (if part of a double bond),
—CH=CH—, where R is selected from hydrogen and C$_{1-4}$-alkyl; Z and Z* are independently selected among an internucleoside linkage, a terminal group or a protecting group; B constitutes a natural or non-natural nucleotide base moiety; and the asymmetric groups may be found in either orientation.

Preferably, the LNA used in the oligomer of the invention comprises at least one LNA unit according any of the formulas

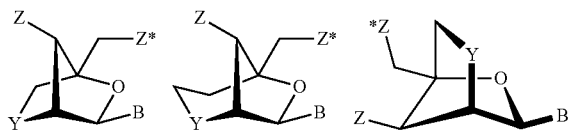

wherein Y is —O—, —S—, —NH—, or N(R$^H$); Z and Z* are independently selected among an internucleoside linkage, a terminal group or a protecting group; B constitutes a natural or non-natural nucleotide base moiety, and RH is selected from hydrogen and C$_{1-4}$-alkyl.

Preferably, the LNA used in the oligomeric compound, such as an antisense oligonucleotide, of the invention comprises at least one nucleotide comprises a LNA unit according any of the formulas shown in "Scheme 2" of PCT/DK2006/000512.

Preferably, the LNA used in the oligomer of the invention comprises internucleoside linkages selected from —O—P(O)$_2$—O—, —O—P(O,S)—O—, —O—P(S)$_2$—O—, —S—P(O)$_2$—O—, —S—P(O,S)—O—, —S—P(S)$_2$—O—, —O—(O)$_2$—S—, —O—P(O,S)—S—, —S—P(O)$_2$—S—, —O—PO(R$^H$)—O—, O—PO(OCH$_3$)—O—, —O—PO(NR$^H$)—O—, —O—PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—O—, —NR$^H$—CO—O—, where R$^H$ is selected from hydrogen and C$_{1-4}$-alkyl.

Specifically, preferred LNA units are shown in Scheme 1:

Scheme 1

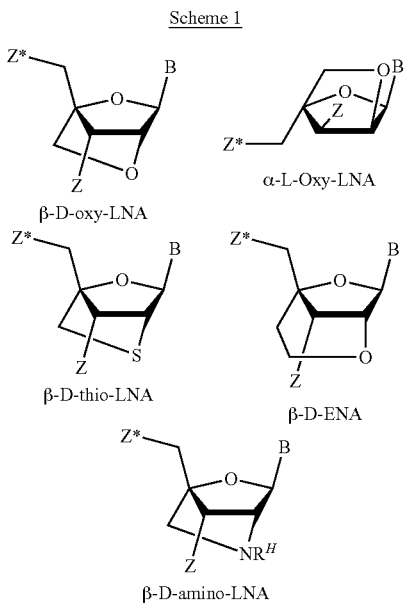

β-D-oxy-LNA

α-L-Oxy-LNA

β-D-thio-LNA

β-D-ENA

β-D-amino-LNA

The term "thio-LNA" comprises a locked nucleotide in which at least one of X or Y in the general formula above is selected from S or —CH2-S—. Thio-LNA can be in both beta-D and alpha-L-configuration.

The term "amino-LNA" comprises a locked nucleotide in which at least one of X or Y in the general formula above is selected from —N(H)—, N(R)—, CH$_2$—N(H)—, and —CH$_2$—N(R)— where R is selected from hydrogen and C$_{1-4}$-alkyl. Amino-LNA can be in both beta-D and alpha-L-configuration.

The term "oxy-LNA" comprises a locked nucleotide in which at least one of X or Y in the general formula above represents —O— or —CH$_2$—O—. Oxy-LNA can be in both beta-D and alpha-L-configuration.

The term "ena-LNA" comprises a locked nucleotide in which Y in the general formula above is —CH$_2$—O— (where the oxygen atom of —CH$_2$—O— is attached to the 2'-position relative to the base B). LNAs are described in additional detail below.

One or more substituted sugar moieties can also be included, e.g., one of the following at the 2' position: OH, SH, SCH₃, F, OCN, OCH₃, OCH₃ O(CH₂)n CH₃, O(CH₂)n NH₂ or O(CH₂)n CH₃ where n is from 1 to about 10; Ci to C10 lower alkyl, alkoxyalkoxy, substituted lower alkyl, alkaryl or aralkyl; Cl; Br; CN; CF3; OCF3; O—, S—, or N-alkyl; O—, S—, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-0-CH₂CH₂OCH₃, also known as 2'-O-(2-methoxyethyl)] (Martin et al, Helv. Chim. Acta, 1995, 78, 486). Other preferred modifications include 2'-methoxy (2'-0-CH₃), 2'-propoxy (2'-OCH₂ CH₂CH₃) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, isocytosine, pseudoisocytosine, as well as synthetic nucleobases, e.g., 2-aminoadenine, 2-(methylamino)adenine, 2-(imidazolylalkyl)adenine, 2-(aminoalkylamino)adenine or other heterosubstituted alkyladenines, 2-thiouracil, 2-thiothymine, 5-bromouracil, 5-hydroxymethyluracil, 5-propynyluracil, 8-azaguanine, 7-deazaguanine, N6 (6-aminohexyl)adenine, 6-aminopurine, 2-aminopurine, 2-chloro-6-aminopurine and 2,6-diaminopurine or other diaminopurines. See, e.g., Kornberg, "DNA Replication," W. H. Freeman & Co., San Francisco, 1980, pp 75-77; and Gebeyehu, G., et al. Nucl. Acids Res., 15:4513 (1987)). A "universal" base known in the art, e.g., inosine, can also be included. 5-Me-C substitutions have been shown to increase nucleic acid duplex stability by 0.6-1.2<0>C. (Sanghvi, in Crooke, and Lebleu, eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the modifications described herein may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone.

Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in "The Concise Encyclopedia of Polymer Science And Engineering", pages 858-859, Kroschwitz, ed. John Wiley & Sons, 1990; those disclosed by Englisch et al., Angewandle Chemie, International Edition, 1991, 30, page 613, and those disclosed by Sanghvi, Chapter 15, Antisense Research and Applications," pages 289-302, Crooke, and Lebleu, eds., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, et al., eds, "Antisense Research and Applications," CRC Press, Boca Raton, 1993, pp. 276-278) and are presently preferred base substitutions, even more particularly when combined with 2'-O-methoxyethyl sugar modifications. Modified nucleobases are described in U.S. Pat. Nos. 3,687,808, as well as 4,845,205; 5,130,302; 5,134, 066; 5,175,273; 5,367,066; 5,432,272; 5,457,187; 5,459, 255; 5,484,908; 5,502,177; 5,525,711; 5,552,540; 5,587, 469; 5,596,091; 5,614,617; 5,750,692; and 5,681,941, each of which is herein incorporated by reference.

In some embodiments, the inhibitory nucleic acids are chemically linked to one or more moieties or conjugates that enhance the activity, cellular distribution, or cellular uptake of the oligonucleotide. For example, one or more inhibitory nucleic acids, of the same or different types, can be conjugated to each other; or inhibitory nucleic acids can be conjugated to targeting moieties with enhanced specificity for a cell type or tissue type. Such moieties include, but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxy-cholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552, 538; 5,578,717, 5,580,731; 5,580,731; 5,591,584; 5,109,124; 5,118,802; 5,138,045; 5,414,077; 5,486, 603; 5,512,439; 5,578,718; 5,608,046; 4,587,044; 4,605,735; 4,667,025; 4,762, 779; 4,789,737; 4,824,941; 4,835,263; 4,876,335; 4,904,582; 4,958,013; 5,082, 830; 5,112,963; 5,214,136; 5,082,830; 5,112,963; 5,214,136; 5, 245,022; 5,254,469; 5,258,506; 5,262,536; 5,272,250; 5,292,873; 5,317,098; 5,371,241, 5,391, 723; 5,416,203, 5,451,463; 5,510,475; 5,512,667; 5,514,785; 5, 565,552; 5,567,810; 5,574,142; 5,585,481; 5,587,371; 5,595,726; 5,597,696; 5,599,923; 5,599, 928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; and 5,688,941.

The inhibitory nucleic acids useful in the present methods are sufficiently complementary to the target RNA, e.g., hybridize sufficiently well and with sufficient biological functional specificity, to give the desired effect. "Complementary" refers to the capacity for pairing, through base stacking and specific hydrogen bonding, between two sequences comprising naturally or non-naturally occurring (e.g., modified as described above) bases (nucleosides) or analogs thereof. For example, if a base at one position of an inhibitory nucleic acid is capable of hydrogen bonding with a base at the corresponding position of an RNA, then the bases are considered to be complementary to each other at that position. 100% complementarity is not required. As noted above, inhibitory nucleic acids can comprise universal bases, or inert abasic spacers that provide no positive or negative contribution to hydrogen bonding. Base pairings may include both canonical Watson-Crick base pairing and non-Watson-Crick base pairing (e.g., Wobble base pairing and Hoogsteen base pairing). It is understood that for complementary base pairings, adenosine-type bases (A) are complementary to thymidine-type bases (T) or uracil-type bases (U), that cytosine-type bases (C) are complementary to guanosine-type bases (G), and that universal bases such as such as 3-nitropyrrole or 5-nitroindole can hybridize to and are considered complementary to any A, C, U, or T. Nichols et al., Nature, 1994; 369:492-493 and Loakes et al., Nucleic Acids Res., 1994; 22:4039-4043. Inosine (I) has also been considered in the art to be a universal base and is considered complementary to any A, C, U, or T. See Watkins and SantaLucia, Nucl. Acids Research, 2005; 33 (19): 6258-6267.

In some embodiments, the location on a target RNA to which an inhibitory nucleic acids hybridizes is defined as a region to which a protein binding partner binds. Routine methods can be used to design an inhibitory nucleic acid that binds to this sequence with sufficient specificity. In some embodiments, the methods include using bioinformatics methods known in the art to identify regions of secondary structure, e.g., one, two, or more stem-loop structures, or pseudoknots, and selecting those regions to target with an inhibitory nucleic acid. For example, methods of designing oligonucleotides similar to the inhibitory nucleic acids described herein, and various options for modified chemistries or formats, are exemplified in Lennox and Behlke, Gene Therapy (2011) 18:1111-1120, which is incorporated herein by reference in its entirety, with the understanding that the present disclosure does not target miRNA 'seed regions'.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure. Target segments 5-500 nucleotides in length comprising a stretch of at least five (5) consecutive nucleotides within the protein binding region, or immediately adjacent thereto, are considered to be suitable for targeting as well. Target segments can include sequences that comprise at least the 5 consecutive nucleotides from the 5'-terminus of one of the protein binding regions (the remaining nucleotides being a consecutive stretch of the same RNA beginning immediately upstream of the 5'-terminus of the binding segment and continuing until the inhibitory nucleic acid contains about 5 to about 100 nucleotides). Similarly preferred target segments are represented by RNA sequences that comprise at least the 5 consecutive nucleotides from the 3'-terminus of one of the illustrative preferred target segments (the remaining nucleotides being a consecutive stretch of the same RNA beginning immediately downstream of the 3'-terminus of the target segment and continuing until the inhibitory nucleic acid contains about 5 to about 100 nucleotides). One having skill in the art armed with the sequences provided herein will be able, without undue experimentation, to identify further preferred protein binding regions to target with complementary inhibitory nucleic acids.

In the context of the present disclosure, hybridization means base stacking and hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as the term is used in the art, refers to the capacity for precise pairing between two nucleotides. For example, if a nucleotide at a certain position of an oligonucleotide is capable of hydrogen bonding with a nucleotide at the same position of a RNA molecule, then the inhibitory nucleic acid and the RNA are considered to be complementary to each other at that position. The inhibitory nucleic acids and the RNA are complementary to each other when a sufficient number of corresponding positions in each molecule are occupied by nucleotides that can hydrogen bond with each other through their bases. Thus, "specifically hybridizable" and "complementary" are terms which are used to indicate a sufficient degree of complementarity or precise pairing such that stable and specific binding occurs between the inhibitory nucleic acid and the RNA target. For example, if a base at one position of an inhibitory nucleic acid is capable of hydrogen bonding with a base at the corresponding position of a RNA, then the bases are considered to be complementary to each other at that position. 100% complementarity is not required.

It is understood in the art that a complementary nucleic acid sequence need not be 100% complementary to that of its target nucleic acid to be specifically hybridizable. A complementary nucleic acid sequence for purposes of the present methods is specifically hybridizable when binding of the sequence to the target RNA molecule interferes with the normal function of the target RNA to cause a loss of activity (e.g., inhibiting LIN28B) and there is a sufficient degree of complementarity to avoid non-specific binding of the sequence to non-target RNA sequences under conditions in which avoidance of the non-specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

In general, the inhibitory nucleic acids useful in the methods described herein have at least 80% sequence complementarity to a target region within the target nucleic acid, e.g., 90%, 95%, or 100% sequence complementarity to the target region within an RNA. For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Antisense and other compounds of the invention that hybridize to an RNA are identified through routine experimentation. In general the inhibitory nucleic acids must retain specificity for their target, i.e., either do not directly bind to, or do not directly significantly affect expression levels of, transcripts other than the intended target.

Target-specific effects, with corresponding target-specific functional biological effects, are possible even when the inhibitory nucleic acid exhibits non-specific binding to a large number of non-target RNAs. For example, short 8 base long inhibitory nucleic acids that are fully complementary to a RNA may have multiple 100% matches to hundreds of sequences in the genome, yet may produce target-specific effects, e.g. downregulation of a MIN28B. 8-base inhibitory nucleic acids have been reported to prevent exon skipping with a high degree of specificity and reduced off-target effect. See Singh et al., RNA Biol., 2009; 6(3): 341-350. 8-base inhibitory nucleic acids have been reported to interfere with miRNA activity without significant off-target effects. See Obad et al., Nature Genetics, 2011; 43: 371-378.

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNA molecules); US2007/0191294 (siRNA analogues); US2008/0249039 (modified siRNA); and WO2010/129746 and WO2010/040112 (inhibitory nucleic acids).

Antisense

In some embodiments, the inhibitory nucleic acids are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to an RNA in vitro, and are expected to inhibit the activity of Lin28b in vivo. Thus, oligonucleotides are chosen that are sufficiently complementary to the target, i.e., that hybridize sufficiently well and with sufficient biological functional specificity, to give the desired effect.

Modified Base, including Locked Nucleic Acids (LNAs)

In some embodiments, the inhibitory nucleic acids used in the methods described herein comprise one or more modified bonds or bases. Modified bases include phosphorothioate, methylphosphonate, peptide nucleic acids, or locked nucleic acids (LNAs). Preferably, the modified nucleotides are part of locked nucleic acid molecules, including [alpha]-L-LNAs. LNAs include ribonucleic acid analogues wherein the ribose ring is "locked" by a methylene bridge between the 2'-oxygen and the 4'-carbon—i.e., oligonucleotides containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., RNAs as described herein.

The modified base/LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the RNA. The modified base/LNA molecules can be chemically synthesized using methods known in the art.

The modified base/LNA molecules can be designed using any method known in the art; a number of algorithms are known, and are commercially available (e.g., on the internet, for example at exiqon.com). See, e.g., You et al., Nucl. Acids. Res. 34:e60 (2006); McTigue et al., Biochemistry 43:5388-405 (2004); and Levin et al., Nucl. Acids. Res. 34:e142 (2006). For example, "gene walk" methods, similar to those used to design antisense oligos, can be used to optimize the inhibitory activity of a modified base/LNA molecule; for example, a series of oligonucleotides of 10-30 nucleotides spanning the length of a target RNA can be prepared, followed by testing for activity. Optionally, gaps, e.g., of 5-10 nucleotides or more, can be left between the LNAs to reduce the number of oligonucleotides synthesized and tested. GC content is preferably between about 30-60%. General guidelines for designing modified base/LNA molecules are known in the art; for example, LNA sequences will bind very tightly to other LNA sequences, so it is preferable to avoid significant complementarity within an LNA molecule. Contiguous runs of three or more Gs or Cs, or more than four LNA residues, should be avoided where possible (for example, it may not be possible with very short (e.g., about 9-10 nt) oligonucleotides). In some embodiments, the LNAs are xylo-LNAs.

For additional information regarding LNA molecules see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175; and 20100035968; Koshkin et al. Tetrahedron 54, 3607-3630 (1998); Obika et al. Tetrahedron Lett. 39, 5401-5404 (1998); Jepsen et al., Oligonucleotides 14:130-146 (2004); Kauppinen et al., Drug Disc. Today 2(3):287-290 (2005); and Ponting et al., Cell 136(4):629-641 (2009), and references cited therein.

As demonstrated herein and previously (see, e.g., WO 2012/065143 and WO 2012/087983, incorporated herein by reference), LNA molecules can be used as a valuable tool to manipulate and aid analysis of RNAs. Advantages offered by an LNA molecule-based system are the relatively low costs, easy delivery, and rapid action. While other inhibitory nucleic acids may exhibit effects after longer periods of time, LNA molecules exhibit effects that are more rapid, e.g., a comparatively early onset of activity, are fully reversible after a recovery period following the synthesis of new RNA, and occur without causing substantial or substantially complete RNA cleavage or degradation. One or more of these design properties may be desired properties of the inhibitory nucleic acids of the invention. Additionally, LNA molecules make possible the systematic targeting of domains within much longer nuclear transcripts. Although a PNA-based system has been described earlier, the effects on Xi were apparent only after 24 hours (Beletskii et al., Proc Natl Acad Sci USA. 2001; 98:9215-9220). The LNA technology enables high-throughput screens for functional analysis of non-coding RNAs and also provides a novel tool to manipulate chromatin states in vivo for therapeutic applications.

In various related aspects, the methods described herein include using LNA molecules to target RNAs for a number of uses, including as a research tool to probe the function of a specific RNA, e.g., in vitro or in vivo. The methods include selecting one or more desired RNAs, designing one or more LNA molecules that target the RNA, providing the designed LNA molecule, and administering the LNA molecule to a cell or animal. The methods can optionally include selecting a region of the RNA and designing one or more LNA molecules that target that region of the RNA.

Aberrant imprinted gene expression is implicated in several diseases including Long QT syndrome, Beckwith-Wiedemann, Prader-Willi, and Angelman syndromes, as well as behavioral disorders and carcinogenesis (see, e.g., Falls et al., Am. J. Pathol. 154:635-647 (1999); Lalande, Annu Rev Genet 30:173-195 (1996); Hall, Ann Rev Med. 48:35-44 (1997)). LNA molecules can be created to treat such imprinted diseases. As one example, the long QT Syndrome can be caused by a K⁺ gated calcium-channel encoded by Kcnq1. This gene is regulated by its antisense counterpart, the long noncoding RNA, Kcnq1ot1 (Pandey et al., Mol Cell. 2008 Oct. 24; 32(2):232-46). Disease arises when Kcnq1ot1 is aberrantly expressed. LNA molecules can be created to downregulate Kcnq1ot1, thereby restoring expression of Kcnq1. As another example, LNA molecules could inhibit RNA cofactors for polycomb complex chromatin modifiers to reverse the imprinted defect.

From a commercial and clinical perspective, the timepoints between about 1 to 24 hours potentially define a window for epigenetic reprogramming. The advantage of the LNA system is that it works quickly, with a defined half-life, and is therefore reversible upon degradation of LNAs, at the same time that it provides a discrete timeframe during which epigenetic manipulations can be made. By targeting nuclear long RNAs, LNA molecules or similar polymers, e.g., xylo-LNAs, might be utilized to manipulate the chromatin state of cells in culture or in vivo, by transiently eliminating the regulatory RNA and associated proteins long enough to alter the underlying locus for therapeutic purposes. In particular, LNA molecules or similar polymers that specifically bind to, or are complementary to, LIN28B can inhibit LIN28B expression, in a gene-specific fashion.

Interfering RNA, Including siRNA/shRNA

In some embodiments, the inhibitory nucleic acid sequence that is complementary to an RNA can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as a "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); Yu et al. Proc Natl Acad Sci USA 99:6047-6052, (2002).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target.

Ribozymes

In some embodiments, the inhibitory nucleic acids are ribozymes. Trans-cleaving enzymatic nucleic acid molecules can also be used; they have shown promise as therapeutic agents for human disease (Usman & McSwiggen, 1995 Ann. Rep. Med. Chem. 30, 285-294; Christoffersen and Marr, 1995 J. Med. Chem. 38, 2023-2037). Enzymatic nucleic acid molecules can be designed to cleave specific RNA targets within the background of cellular RNA. Such a cleavage event renders the RNA non-functional.

In general, enzymatic nucleic acids with RNA cleaving activity act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, 1979, Proc. R. Soc. London, B 205, 435) have been used to evolve new nucleic acid catalysts capable of catalyzing a variety of reactions, such as cleavage and ligation of phosphodiester linkages and amide linkages, (Joyce, 1989, Gene, 82, 83-87; Beaudry et al., 1992, Science 257, 635-641; Joyce, 1992, Scientific American 267, 90-97; Breaker et al, 1994, TIBTECH 12, 268; Bartel et al, 1993, Science 261 :1411-1418; Szostak, 1993, TIBS 17, 89-93; Kumar et al, 1995, FASEB J., 9, 1183; Breaker, 1996, Curr. Op. Biotech., 1, 442). The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 $\text{min}^{-1}$ in the presence of saturating (10 mM) concentrations of $\text{Mg}^{2+}$ cofactor. An artificial "RNA ligase" ribozyme has been shown to catalyze the corresponding self-modification reaction with a rate of about 100 $\text{min}^{-1}$. In addition, it is known that certain modified hammerhead ribozymes that have substrate binding arms made of DNA catalyze RNA cleavage with multiple turn-over rates that approach 100 $\text{min}^{-1}$.

Making and Using Inhibitory Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. If desired, nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)).

Preferably, inhibitory nucleic acids of the invention are synthesized chemically. Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066; WO/2008/043753 and WO/2008/049085, and the references cited therein.

Nucleic acid sequences of the invention can be stabilized against nucleolytic degradation such as by the incorporation of a modification, e.g., a nucleotide modification. For example, nucleic acid sequences of the invention includes a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O—NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290 (2005); Koshkin et al., J. Am. Chem. Soc., 120(50):13252-13253 (1998)). For additional modifications see US 20100004320, US 20090298916, and US 20090143326.

It is understood that any of the modified chemistries or formats of inhibitory nucleic acids described herein can be combined with each other, and that one, two, three, four, five, or more different types of modifications can be included within the same molecule.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., Molecular Cloning; A Laboratory Manual 3d ed. (2001); Current Protocols in Molecular Biology, Ausubel et al., eds. (John Wiley & Sons, Inc., New York 2010); Kriegler, Gene Transfer and Expression: A Laboratory Manual (1990); Laboratory Techniques In Biochemistry And Molecular Biology: Hybridization With Nucleic Acid Probes, Part I. Theory and Nucleic Acid Preparation, Tijssen, ed. Elsevier, N.Y. (1993).

Pharmaceutical Compositions

The methods described herein can include the administration of pharmaceutical compositions and formulations comprising inhibitory nucleic acid sequences designed to target an RNA.

In some embodiments, the compositions are formulated with a pharmaceutically acceptable carrier. The pharmaceutical compositions and formulations can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., Remington: The Science and Practice of Pharmacy, 21st ed., 2005.

The inhibitory nucleic acids can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations of this invention can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

The pharmaceutical compounds can also be administered by in intranasal, intraocular and intravaginal routes including suppositories, insufflation, powders and aerosol formulations (for examples of steroid inhalants, see e.g., Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols.

In some embodiments, the pharmaceutical compounds can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In some embodiments, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising an inhibitory nucleic acid can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. 20040028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; and 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587. As used in the present invention, the term "liposome" means a vesicle composed of amphiphilic lipids arranged in a bilayer or bilayers. Liposomes are unilamellar or multilamellar vesicles that have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes can also include "sterically stabilized" liposomes, i.e., liposomes comprising one or more specialized lipids. When incorporated into liposomes, these specialized lipids result in liposomes with enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The formulations of the invention can be administered for prophylactic and/or therapeutic treatments. In some embodiments, for therapeutic applications, compositions are administered to a subject who is need of reduced triglyceride levels, or who is at risk of or has a disorder described herein, in an amount sufficient to cure, alleviate or partially arrest the clinical manifestations of the disorder or its complications; this can be called a therapeutically effective amount. For example, in some embodiments, pharmaceutical compositions of the invention are administered in an amount sufficient to decrease serum levels of triglycerides in the subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; Remington: The Science and Practice of Pharmacy, 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, the degree and amount of therapeutic effect generated after each administration (e.g., effect on tumor size or growth), and the like. The formulations should provide a sufficient quantity of active agent to effectively treat, prevent or ameliorate conditions, diseases or symptoms.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington: The Science and Practice of Pharmacy, 21st ed., 2005.

Various studies have reported successful mammalian dosing using complementary nucleic acid sequences. For example, Esau C., et al., (2006) Cell Metabolism, 3(2):87-98 reported dosing of normal mice with intraperitoneal doses of miR-122 antisense oligonucleotide ranging from 12.5 to 75 mg/kg twice weekly for 4 weeks. The mice appeared healthy and normal at the end of treatment, with no loss of body weight or reduced food intake. Plasma transaminase levels were in the normal range (AST 3/4 45, ALT 3/4 35) for all doses with the exception of the 75 mg/kg dose of miR-122 ASO, which showed a very mild increase in ALT and AST levels. They concluded that 50 mg/kg was an effective, non-toxic dose. Another study by Krützfeldt J., et al., (2005) Nature 438, 685-689, injected anatgomirs to silence miR-122 in mice using a total dose of 80, 160 or 240 mg per kg body weight. The highest dose resulted in a complete loss of miR-122 signal. In yet another study, locked nucleic acid molecules ("LNA molecules") were successfully applied in primates to silence miR-122. Elmen J., et al., (2008) Nature 452, 896-899, report that efficient silencing of miR-122 was achieved in primates by three doses of 10 mg kg-1 LNA-antimiR, leading to a long-lasting and reversible decrease in total plasma cholesterol without any evidence for LNA-associated toxicities or histopathological changes in the study animals.

In some embodiments, the methods described herein can include co-administration with other drugs or pharmaceuticals, e.g., compositions for providing cholesterol homeostasis. For example, the inhibitory nucleic acids can be co-administered with other treatment options for treating or reducing risk of PDAC, e.g., surgery (e.g., a Whipple's operation), chemotherapy (e.g., gemcitabine (GEMZAR®), FOLFIRINOX, Nab-paclitaxel (ABRAXANE®), fluorouracil (5-FU), capecitabine (XELODA®), oxaliplatin (ELOXATIN®)), radiotherapy, and/or irreversible electroporation (e.g., NANOKNIFE®).

EXAMPLES

The invention is further described in the following examples, which do not limit the scope of the invention described in the claims.
Experimental Procedures
The following methods were used in the Examples set forth below, unless otherwise noted.
Mice
Mice were housed in pathogen-free animal facilities. All experiments were conducted under protocol 2007N000200 approved by the Subcommittee on Research Animal Care at Massachusetts General Hospital. Mice were maintained on a mixed 129SV/C57BL/6 background. Data presented include both male and female mice. All mice included in the survival analysis were euthanized when criteria for disease burden were reached.

Sirt6$^{flox/flox}$ conditional strain (Sebastian et al., 2012) were crossed with the p48-Cre strain (Kawaguchi et al., 2002), the conditional p53$^{flox}$ strain (Marino et al., 2000) and the LSL-Kras$^{G12D}$ strain (Jackson et al., 2001) which consists of a mutant Kras$^{G12D}$ allele knocked into the endogenous Kras locus, preceded by an LSL cassette.

Cell Lines
Pancreatic cancer cell lines, HPAFII, KP4, MiaPaCa, SW1990, YAPC, 8988T, PSN1, 89a, Panc03.27, Panc-1, BxPc3, HPAC, Panc8.13, ASPC-1, Su86.86 and HPNE were obtained from American Type Culture Collection (ATCC; Rockville, Md.), and grown in their required growth medium per ATCC description. The DanG pancreatic cancer cells were obtained from DSMZ, SUIT-2 were obtained from JCRB cell bank and COLO357 was a gift from Paul Chiao (MD Anderson). All were grown in RPMI 1640 supplemented with 10% fetal bovine serum and 1% penicillin (100 U/ml)/streptomycin (100 Ug/ml) (Invitrogen Gibco). Human pancreatic ductal epithelial cells (HPDE) (Furukawa et al., 1996) were obtained from Ming Tsao (University of Toronto) and grown in keratinocyte serum-free (KSF) medium with 0.2 ng/ml EGF and 30 µg/ml bovine pituitary extract (Invitrogen Gibco, Carlsbad, Calif.) at 37° C. under 5% CO2. To establish mouse pancreatic cancer cell lines, freshly isolated tumor specimens from Sirt6$^{f/f}$; Kras$^{G12D}$; p53$^{f/+}$; p48-Cre (SIRT6 KO) and Sirt6$^{+/+}$; Kras$^{G12D}$; p53$^{f/+}$; p48-Cre (SIRT6 WT) mice were minced with sterile razor blades, digested with trypsin for 30 minutes at 37° C., and then resuspended in RPMI 1640 and supplemented with 10% fetal bovine serum and 1% penicillin (100 U/ml)/streptomycin (100 Ug/ml) (Invitrogen Gibco) and seeded on plates coated with rat tail collagen (BD Biosciences). Cells were passaged by trypsinization. All studies were done on cells cultivated for less than ten passages. SIRT6 knockout (KO) primary mouse embryonic fibroblast (MEFs) were generated from 13.5-day-old embryos as described (Mostoslaysky et al., 2006). These cells were immortalized by using the standard 3T3 protocol. Cells were cultured in high glucose Dulbecco's modified Eagle's medium (DMEM) supplemented with 10% fetal bovine serum, 1% penicillin (100 U/ml)/streptomycin (100 Ug/ml) (Invitrogen), 2 mM L-glutamine, 0.1mM NEAA, 1mM sodium pyruvate, and 20 mM HEPES.

Constructs and Viral Infection
Full-length wild-type SIRT6 cDNA (variant 1; NM_016539.2) was amplified from the HPDE cells using the following primers (CAGGATCCTTGTTC-CCGTGGGGCAGTCGAGG (SEQ ID NO:1); bold sequence indicates BamHI site) and (CAGAATTCCTA-CAAAAAGCCCCACCCTCCC (SEQ ID NO:2); bold sequence indicates EcoRI site). Following PCR amplification and subcloning into pGEMT (Promega), SIRT6 constructs were digested with BamHI and EcoRI, and purified with the QIAquick Gel extraction kit (Qiagen). Digested SIRT6 was subcloned into pRetroX-TIGHT-Pur plasmid (Clontech) and site-directed mutagenesis of wild-type SIRT6 used the QuikChange Lightning site-directed mutagenesis kit (Stratagene, La Jolla, Calif., USA) to generate the H133Y, catalytic dead mutant. pLVX-Tet-On was obtained from Clontech. pMSCV-3xFlag-SIRT6 was previously described in (Sebastian et al., 2012).

The following lentiviral plasmids were used: Human pTRIPz-shSIRT6 (Dharmacon RHS4740) and negative control shRNA vector was a kind gift from David Lombard. Human and mouse (target sequence conserved) pLKO.1-shLIN28B vector (TRCN0000122599) target sequence: 5'-GCCTTGAGTCAATACGGGTAA-3' (SEQ ID NO:3); pLKO.1-shHMGA2 vector (TRCN0000021965) target sequence: 5'-GCCACAACAAGTTGTTCAGAA-3' (SEQ ID NO:4); pLKO.1-shMYC-2 vector (TRCN0000039639) target sequence: 5'-CCCAAGGTAGTTATCCTTAAA-3' (SEQ ID NO:5); pLKO.1-shMYC-5 vector (TRCN0000039642) target sequence: 5'-CCTGAGACA-GATCAGCAACAA-3' (SEQ ID NO:6); pLKO.1-shIGF2BP3-1 vector (TRCN0000074673) target sequence: 5'-GCCTCATTCTTATTTCAAGAT-3' (SEQ ID NO:7); pLKO.1-shIGF2BP3-3 vector (TRCN0000074675) target sequence: 5'-CGGTGAATGAACTTCAGAATT-3' (SEQ ID NO:8); pLKO.1-shIGF2BP1-2 vector (TRCN0000075149) target sequence: 5'-GCAGTGGTGAATGTCACCTAT-3' (SEQ ID NO:9); pLKO.1-shIGF2BP1-5 vector (TRCN0000075152) target sequence: 5'-CCTGGC-CCATAATAACTTTGT-3' (SEQ ID NO:10); mouse pLKO.1-shPdk1 vector (TRCN0000078808) target sequence: 5'-GCTGAGTATTTCTTTCAAGTT-3' (SEQ ID NO:11) and mouse pLKO1-shLdha-2 vector (TRCN0000041744) target sequence: 5'-CGTGAACATCT-TCAAGTTCAT-3' (SEQ ID NO:12) and mouse pLKO.1 shLdha-5 vector (TRCN0000041747) target sequence: 5'-CGTCTCCCTGAAGTCTCTTAA-3' (SEQ ID NO:13) were obtained from the MGH RNAi Consortium Library. Mouse pLKO.1-shMYC vector (TRCN0000042514) target sequence: 5'-GCCTACATCCTGTCCATTCAA-3' (SEQ ID NO:14; Open Biosciences). pLKO.1 shRNA (shCtl) with target sequence 5'-GCAAGCTGACCCTGAAGTTCAT-3' (SEQ ID NO:15) was used as negative control shRNA. pBabe let-7g 7S21L mutant construct was a kind gift from Richard Gregory.

Viral particles containing the above mentioned plasmids were synthesized using either lentiviral (pCMV-dR8.91) or retroviral (pCL-ECO) packaging plasmids with pCMV-VSV-G (Addgene). Cells were infected by incubating with virus and 10 μg/ml polybrene. Twenty-four hours later, cells were selected in 2.5 μg/ml puromycin for at least two days and the pooled populations were used for various experiments. For all experiments involving the dox-inducible pRetro construct cells were treated with 1 μg/mL dox for 48 hours and for the dox-inducible shSIRT6 cells were treated with 1 μg/mL dox for 72 hours unless otherwise indicated.

Silencer Select siRNA were purchased from Ambion and 10 nM was transfected into cells with Lipofectamine RNAiMax (Invitrogen). Negative control #1 (4390843), mouse siLin28b #1 (4390771 s117291), mouse siLin28b #2 (4390771 s117292), mouse siIgf2bp3 (4390771 s100444) human siLin28b #1 (4392420 s52477) and human siLin28b #2 (4392420 s52478). miRCURY LNA Let-7 mimetics were purchased from Exiquon and 50 nM was reverse transfected into cells with Lipofectamine RNAiMax (Invitrogen). Negative control mimetic (479903-001), hsa-let7c-5p (471696-001) and hsa-let7d-5p (470030-001).

Gel Electrophoresis and Western Blotting

Chromatin fractions were prepared by resuspending the cell pellet in lysis buffer containing 10mM HEPES pH 7.4, 10 mM KCl, 0.05% NP-40 supplemented with a protease inhibitor cocktail (Complete EDTA-free, Roche Applied Science), 5 μM TSA, 5 mM sodium butyrate, 1 mM DTT, 1 mM PMSF, 50 mM NaF, 0.2 mM sodium orthovanadate and phosphatase inhibitors (Phosphatase Inhibitor Cocktail Sets I and II, Calbiochem) and incubated on ice for 20 minutes. The lysate was then centrifuged at 14,000 rpm for 10 minutes at 4° C. The supernatant was removed (cytosolic fraction) and the pellet (nuclei) was acid-extracted using 0.2N HCl and incubated on ice for 20 minutes. The lysate was then centrifuged at 14,000 rpm for 10 minutes at 4° C. The supernatant (contains acid soluble proteins) was neutralized using 1M Tris-HCl pH 8. For whole cell lysate (WCL), the cell pellet was resuspended in RIPA buffer supplemented with a protease inhibitor cocktail (Complete EDTA-free, Roche Applied Science), 5 μM TSA, 5 mM sodium butyrate, 1 mM DTT, 1 mM PMSF, 50 mM NaF, 0.2 mM sodium orthovanadate and phosphatase inhibitors (Phosphatase Inhibitor Cocktail Sets I and II, Calbiochem) and incubated on ice for 20 minutes. The lysate was then centrifuged at 14,000 rpm for 10 minutes at 4° C. and the supernatant was harvested. Protein concentration was quantified by Biorad Protein Assay. Ten-micrograms protein (chromatin) 20 μg (WCL) was electrophoresed on a 10-20% gradient polyacrylamide gel with SDS (Biorad) and electroblotted onto polyvinylidene difluoride membranes (PVDF) (Millipore). Membranes were blocked in TBS with 5% non-fat milk and 0.1% Tween and probed with anti-SIRT6 (Abcam, ab62739), anti-H3K9Ac (Millipore 07-352), anti-H3K56Ac (ab76307), anti-Lin28b (ab71415 and Cell Signaling 4196), anti-PDK1 (Cell signaling #3820), anti-Myc (ab32072), anti-IGF2BP1 (Cell Signaling #8482), anti-HMGA2 (Cell Signaling #8179), anti-IGF2BP3 (Proteintech 14642-1-AP) and anti-β actin (Sigma A5316) or total-H3 (ab1791) as a loading control. Bound proteins were detected with horseradish-peroxidase-conjugated secondary antibodies (Vector Biolaboratories) and SuperSignal West Pico Luminol/Enhancer Solution (Thermo Scientific).

Glucose Uptake Assay

Cells were grown under normal conditions for 24 hours and 100 μM 2-NBDG (Invitrogen) was added to the media for 2 hours. Fluorescence was measured by flow cytometry using a FACSCalibur Analyzer (BD). Data are shown as mean±std between duplicates and are representative of two independent experiments.

Real-Time RT-PCR Analysis

Total RNA was extracted with the TriPure Isolation Reagent (Roche) as described by the manufacturer. For cDNA synthesis, 1 μg of total RNA was reverse-transcribed by using the QuantiTect Reverse Transcription Kit (Qiagen). Real-time PCR was run in duplicate using SYBR green master mix (Roche), following the manufacturer's instructions, with the exception that the final volume was 12.5 μl of SYBR green reaction mix. Real-time monitoring of PCR amplification was performed using the LightCycler 480 detection system (Roche). Data were expressed as relative mRNA levels normalized to the β-actin expression level in each sample and are represented as mean±s.e.m. between two independent experiments unless otherwise indicated in the figure legend.

MicroRNA Sequencing Analysis

Next-generation sequencing of small RNA-Seq for PLKO and shLIN28b knockdown samples (three replicates each) was performed using Illumina HiSeq instrument, resulting in approximately 35 million pairs of 50-bp reads per sample. These reads were aligned and miRNA expression profiles were generated using miRExpress (Wang et al., 2009), followed by the analysis of differential expression using edgeR package (Robinson et al., 2010).

Tumor Sphere Assay

Cells were plated as single-cell suspension in ultralow attachment 24-well plates (Corning) and grown in DMEM/F12 medium (serum free) supplemented with 20 μl ml$^{-1}$ B27 (Invitrogen), 20 ng ml$^{-1}$ EGF and 20 ng ml$^{-1}$ bFGF. Fresh media (300 μl) was added every 3 days. Tumor spheres were counted and photographed at day 10. Tumor sphere assay was performed in triplicate, and are represented as mean±s.e.m. between three independent experiments.

Xenografts

For murine PDAC xenografts $2 \times 10^4$ cells were injected subcutaneously into the flanks of SCID mice (Charles River). For human PDAC xenografts $5 \times 10^6$ cells in 100 μl PBS: 100 μl Matrigel (Corning) was injected subcutaneously into the flanks of SCID mice (Charles River) For both models, mice were checked for the appearance of tumors twice per week, and the tumors were harvested when they reached ~100 mm in diameter.

Histology and Immunostaining

Pancreata were harvested, submitted for histological examination, and analyzed in a blinded fashion by pathologist (V.D.). For quantification of PanIN and PDAC, a grading scheme endorsed by the WHO (Aaltonen et al., 2000) we used, which is based primarily on the extent of gland formation. Tissue samples were fixed overnight in 4% buffered formaldehyde, and then embedded in paraffin and sectioned (5 μm thickness) by the DF/HCC Research Pathology Core. Haematoxylin and eosin staining was performed using standard methods. Tissue microarrays were constructed from formalin-fixed paraffin embedded tissue with each core measuring 3 mm in diameter. Immunohistochemistry was performed as previously described (Fitamant et al., 2015). Primary antibodies were diluted in blocking solution as follows: anti-Lin28b (LS Bio LS-B3423) 1:200 for mouse and human tissues; anti-SIRT6 (Cell Signaling Technology, #12486) 1:300 for mouse tissues and 1:200 for human tissues. Stained slides were photographed with an Olympus DP72 microscope. Immunohistochemistry was scored semi quantitatively, in a blinded fashion by pathologist (V.D.) on a 0 (no staining) to 3 (strongest intensity) scale based on the intensity of reactivity. A score of 0 was considered $SIRT6^{low}$ while 1-3 was considered $SIRT6^{high}$. For LIN28B staining 0-1 was considered $LIN28B^{low}$ and 2-3 was considered $LIN28B^{high}$.

RNA In Situ Hybridization (RISH) Assay

For the manual (nonautomated) format for ISH, formalin-fixed paraffin-embedded (FFPE) baked tissue sections were subjected to Histoclear deparaffinization (National Diagnostics, Atlanta, Ga.), followed by ethanol dehydration. To unmask the RNA targets, dewaxed sections were incubated in 1× pre-treatment buffer (Affymetrix) (at 90 to 95° C. for 10 minutes and digested with 1:100 dilution protease at 40° C. for 10 minutes, followed by fixation with 10% neutral buffered formalin at room temperature for 5 minutes. Unmasked tissue sections were subsequently hybridized with 1:30 dilution of the Let7a (Affymetrix VM1-10266) probe for 3 hours at 40° C., followed by a series of post-hybridization washes. Signal amplification was achieved by a series of sequential hybridizations and washes as described in the View-RNA user manual (see link below). The specific conditions were as follow: pre-AMP: 25 minutes at 40° C.; AMP: 15 minutes at 40° C.; hybridization with labeled probe: 1:1000 dilution for 15 minutes at 40° C.; signal detection with fast-red substrate: 30 minutes at 40° C. Slides were counterstained with Gill hematoxylin and mounted using Dako Ultramount (Dako, Carpinteria, Calif.).

For the automated Housekeeping gene (HKG) ISH, the assay was performed by using View-RNA eZL Detection Kit (Affymetrix) on the Bond RX immunohistochemistry and ISH Staining System with BDZ 6.0 software (Leica Biosystems). FFPE tissue sections on slides were processed automatically from deparaffinization, through ISH staining to hematoxylin counterstaining. Briefly, 5 mm-thick sections of formalin-fixed tissue were baked for 1 hour at 60° C. and placed on the Bond RX for processing. The Bond RX user-selectable settings were as follows: ViewRNA eZ-1 Detection 1-plex (Red) protocol; ViewRNA Dewaxl Preparation protocol; View RNA HIER 10 minutes, ER1 (setting 95); ViewRNA Enzyme 2 (setting 10); ViewRNA Probe Hybridization. With these settings, the RNA unmasking conditions for the FFPE tissue consisted of a 10-minute incubation at 95° C. in Bond Epitope Retrieval Solution 1 (Leica Biosystems), followed by 10-minute incubation with Proteinase K from the Bond Enzyme Pretreatment Kit at 1:1000 dilution (Leica Biosystems). ViewRNA eZ Check-Human TYPE 1 (Affymetrix Cat # DVA1-16742) (a cocktail of GAPDH, PPIB, and ACTB) was diluted 1:40 in ViewRNA Probe Diluent (Affymetrix). Post run, slides were rinsed with water, air dried for 30 minutes at room temperature and mounted using Dako Ultramount (Dako, Carpinteria, Calif.), and visualized and photographed with an Olympus DP72 microscope. Punctate like red color hybridization signals in the cell nuclei and cytoplasm were defined as positive signal. Slides were scored semi quantitatively in a blinded manner on a 0-3 scale based on the intensity of reactivity. If punctate red dots could be visualized using the 2× or 4× microscope objective then the section was given a score of +3, at 10× a score of +2, at 20× or 40× a score of +1 and finally no signal at 40× was given a score of zero. A score of zero was considered let-7a low and a score of 1-3 was considered let-7a high.

Proliferation Assay

Cells were plated in duplicate on collagen-coated 6-well dishes ($1\times10^4$ per well) in culture medium. Adherent cells were harvested, trypsinized and counted by trypan-blue exclusion using a Countess Automated Cell Counter (Invitrogen) 24, 72, or 120 hours later. Proliferation assays were performed in duplicate and are represented as mean±s.e.m. between three independent experiments. Alternatively, cells were plated in triplicate in 96-well plates (2000 cells/well for human PDAC cells and 500 cells/well on collagen coated plates for murine PDAC cells) in culture medium. MTT (3-(4,5-Dimethylthiazol-2-yl)-2,5-Diphenyltetrazolium Bromide) assay was performed each day for six days. MTT (1.25 mg/mL final concentration) was added to the culture media and incubated for 3 hours. Formazan crystals were solubilized with 100 μL/well of DMSO and absorbance was read at 570 nm. To determine the sensitivity of cells to dichloroacetate, 500 cells/well were seeded on collagen coated plates in culture medium. The following day dichloroacetate was added to the culture medium and cells were allowed to grow for five days after which MTT was added to the culture medium as described above. MTT proliferation assays were performed in triplicate and are represented as mean±s.e.m. between three independent experiments unless otherwise noted in the figure legend.

Apoptosis Assay

Cells were washed with PBS and resuspended in 50 μl of 1× Binding Buffer (10 mM HEPES, pH 7.4; 140 mM NaCl; 2.5 mM CaCl2). 2.5 μl of Annexin V-FITC was added to each sample and incubated 15 minutes in the dark. After this time, 450 μl of 1× Binding Buffer was added and Annexin V positive cells analyzed by flow cytometry. Data are shown as mean±std between triplicates and are representative of two independent experiments.

Caspase 3/7 Activity

Cells were plated at confluency (10,000 cells/well) and allowed to adhere for 24 hours in 96-well plate format. The following day caspase 3/7 activity was assessed using a Caspase-Glo® 3/7 Assay (G8090, Promega) per the manufacturer's recommended protocol. Data are shown as mean±std between triplicates.

Cell Cycle Analysis

Briefly, cells were resuspended in 500 μl of PBS and fixed in ethanol by adding drop-wise 1 ml of 95% ethanol. Fixed cells were incubated at 4 C overnight, washed with PBS and resuspended in 500 μl of PBS-0.1% Triton-X-100 supplemented with 1 μg/ml of RNAse A and 20 μg/ml of propidium iodide. Samples were incubated at 37° C. for 20 minutes followed by 1 hour at 4° C. and DNA content analyzed by flow cytometry. Cell cycle analysis was performed using the ModFit LT software. Data are shown as mean±std between triplicates and are representative of two independent experiments.

Chromatin Immunoprecipitation

ChIP and qRT-PCR were performed as previously described (Donner et al., 2007). The antibodies used were anti-H3K9Ac (Millipore 07-352), anti-H3K56Ac (ab76307). Quantitative RTPCR for ChIP analyses were performed in duplicate and are represented as mean±s.e.m. between two independent experiments.

Chromatin Immunoprecipitation Sequencing

The steps of ChIP followed by sequencing (ChIP-seq) were performed using a modified version of our previous protocols adapted to the Bravo liquid handling platform (Agilent) as previously described (Etchegaray et al., 2015). Mouse PDAC cells were crosslinked, fixed cells were lysed and the chromatin was then sheared on Covaris E-220 to a size range between 200 and 800 bp. An anti-H3K56Ac (ab76307) antibody was used. The antibody was incubated a mix of Protein-A and Protein-G Dynabeads (Invitrogen) then incubated overnight. Next, samples were washed eluted, reverse crosslinked, treated with RNaseA (Roche) and Proteinase K (NEB). Illumina library construction reactions were performed as described previously (Etchegaray et al., 2015), using the Bravo liquid handling platform (Agilent).

H3K56ac ChIP-Seq Data Analysis

Reads from H3K56ac ChIP-Seq for RP07 SIRT6 wild type (S6WT), SK03 SIRT6 knock-out (S6KO), and SK03 SIRT6 knock-out with SIRT6 restored (S6WT) (referred to as samples S1, S2, and S3 respectively) from mouse pancreatic cancer cell lines were aligned to mouse genome mm9 using bwa (Li and Durbin, 2009) and duplicate reads were marked with Picard tools (picard.sourceforge.net). Peaks were called using MACS2 (version 2.0.10) with a False Discovery Rate (FDR) set to 0.01 (Zhang et al., 2008). UCSC Mus musculus mm9 refGene gene annotation was used to generate a list of transcription start sites (TSS) for all genes and used to generate a bed file with TSS +/− 1 kb regions for all genes. The bedtools program intersectBed (bedtools.readthedocs.org/en/latest/index.html) was used to associate the MACS2 peaks from the three H3K56ac ChIP-Seq samples with the TSS +/− 1 kb regions and identify genes with peaks. Intersections of these gene lists were used to generate the Venn diagrams of FIG. 3A. Genes from the 184 gene subset with TSS +/− 1 kb peaks in S2 SK03 S6KO but not in S1 RP07 S6WT and not it S3 SK03 S6WT were prioritized for follow-up according to differential binding of H3K56ac ChIP-Seq reads from S2 SK03 S6KO relative to S1 RP07 S6WT. The R Bioconductor program DBChIP (Liang and Keles, 2012) was used to analyze the differential binding at the TSS locations associated with the 184 S2 but not S1 or S3 peaks. DBChIP was run with a window size of 1000, fragment lengths of 229 and 219 from the MACS2 estimate of fragment length for S1 and S2 respectively, and library sizes of 19319155 and 19059445 from the number of tags after filtering.

Gene Expression Analysis and GSEA

Gene expression data from pancreatic cancer datasets used for the Gene Set Enrichment Analysis (GSEA) in FIGS. 7B-D are accessible from GEO (ncbi.nlm.nih.gov/gds/) (91 pancreatic cancer tumor samples from Perez-Mancera et al. 2012 (GSE36294) (Perez-Mancera et al., 2012), 36 pancreatic cancer tumor samples from Pei et al. 2009 (GSE16515) (Pei et al., 2009), 45 pancreatic cancer tumor samples from Zhang et al. 2012 (GSE28735) (Zhang et al., 2012), and 36 pancreatic ductal adenocarcinoma tumor samples from Badea et al. 2008 (GSE15471) (Badea et al., 2008)), 177 pancreatic adenocarcinoma (PAAD) primary tumor samples from TCGA (cancergenome.nih.gov/), 269 pancreatic cancer ductal adenocarcinoma (PACA-AU v18) tumor samples from Australian pancreatic ICGC (icgc.org) (Waddell et al., 2015), and 43 pancreatic cancer cell line samples from CCLE (broadinstitute.org/software/cprg/?q=node/11) (Bar-retina et al., 2012). For the GEO patient sample data sets GSE16515, GSE28735, and GSE15471 and the CCLE data set, raw expression values in the form of CEL files were collected and then processed using RMA in the R Bioconductor package. For the GEO patient sample data set GSE36924 the series matrix file for the Illumina HumanHT-12 V4.0 expression beadchip data was download. For TCGA data, expression data sets were created by combining RNASeqV2 Level3 normalized gene result files for individual samples and producing tables with genes in rows and samples in columns. ICGC data was read in from the ICGC PACA-AU v18 array file exp_array.PACA-AU.tsv.gz. Gene Set Enrichment Analysis (Mootha et al., 2003; Subramanian et al., 2005) was used to evaluate the association of LIN28B expression with known pathways and phenotypes. GSEA was run using Pearson correlation with LIN28B to rank genes and p-values were obtained from 2500 permutations of the LIN28B expression phenotype. GSEA was performed using two libraries from version 4.0 of the molecular signature database (MolSigDB) (broadinstitute.org/gsea/msigdb/index.jsp): the c2 curated gene sets from online pathway databases, PubMed publications, knowledge of domain experts and the c3 motif gene sets.

Statistics

For qRTPCR analysis, proliferation assays, glucose uptake, tumor sphere formation, and tumor size, significance was analyzed using 2-tailed Student's t test. A p-value of less than 0.05 was considered statistically significant. A log-rank test was used to determine significance for Kaplan-Meier analyses. Fisher's exact t test was performed for comparison of metastatic disease burdens.

Example 1: Loss of SIRT6 Cooperates with Oncogenic Kras to Accelerate PDAC

Figure 1B:
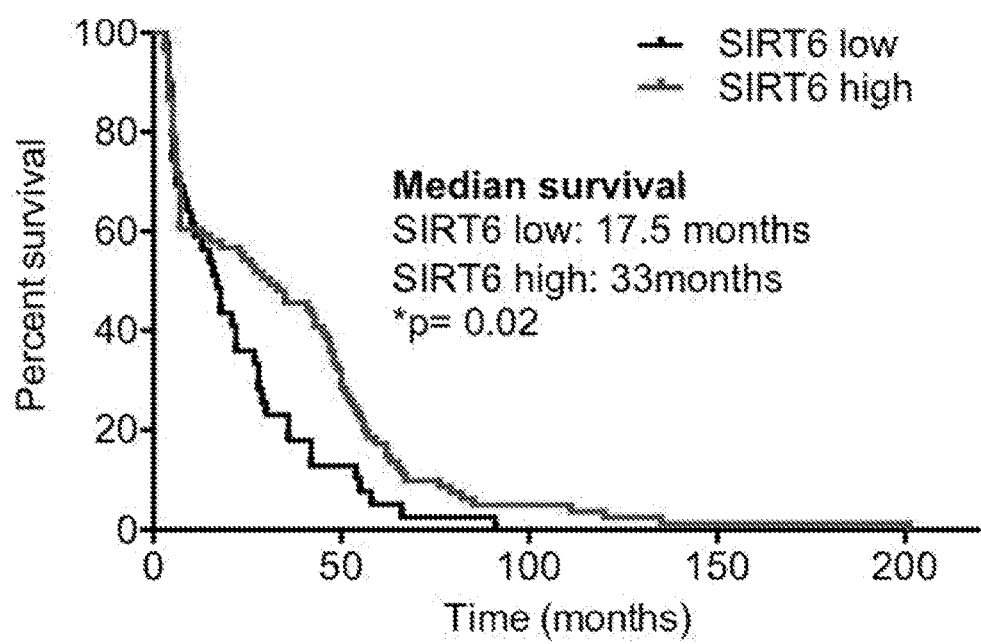
Figure 1C:
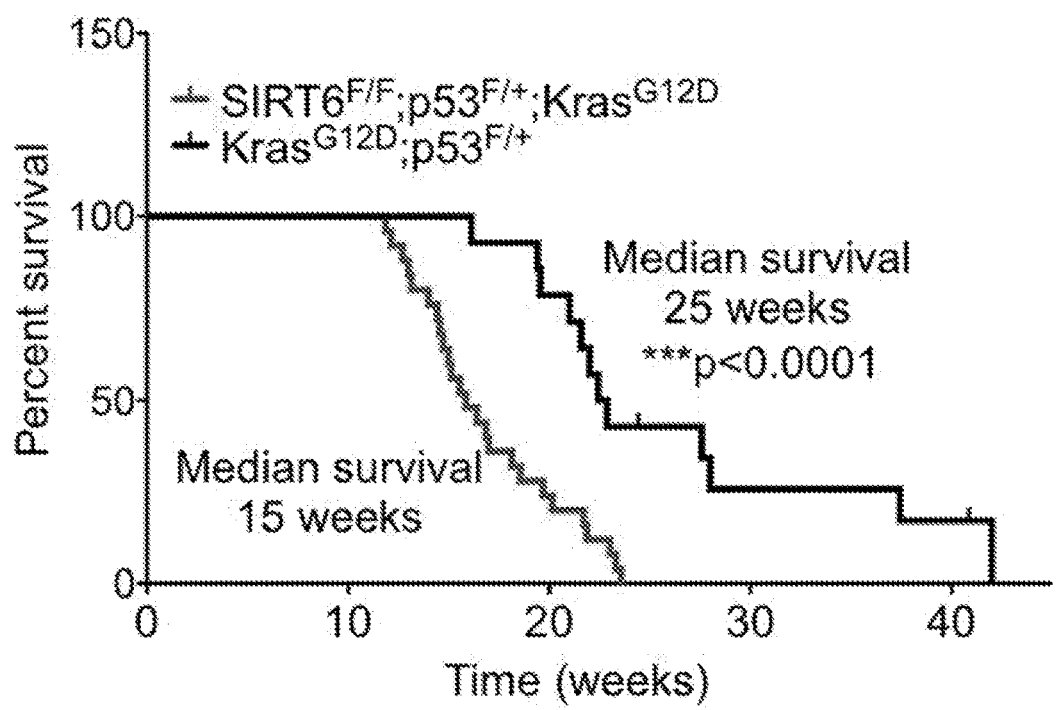
Figure 1D:
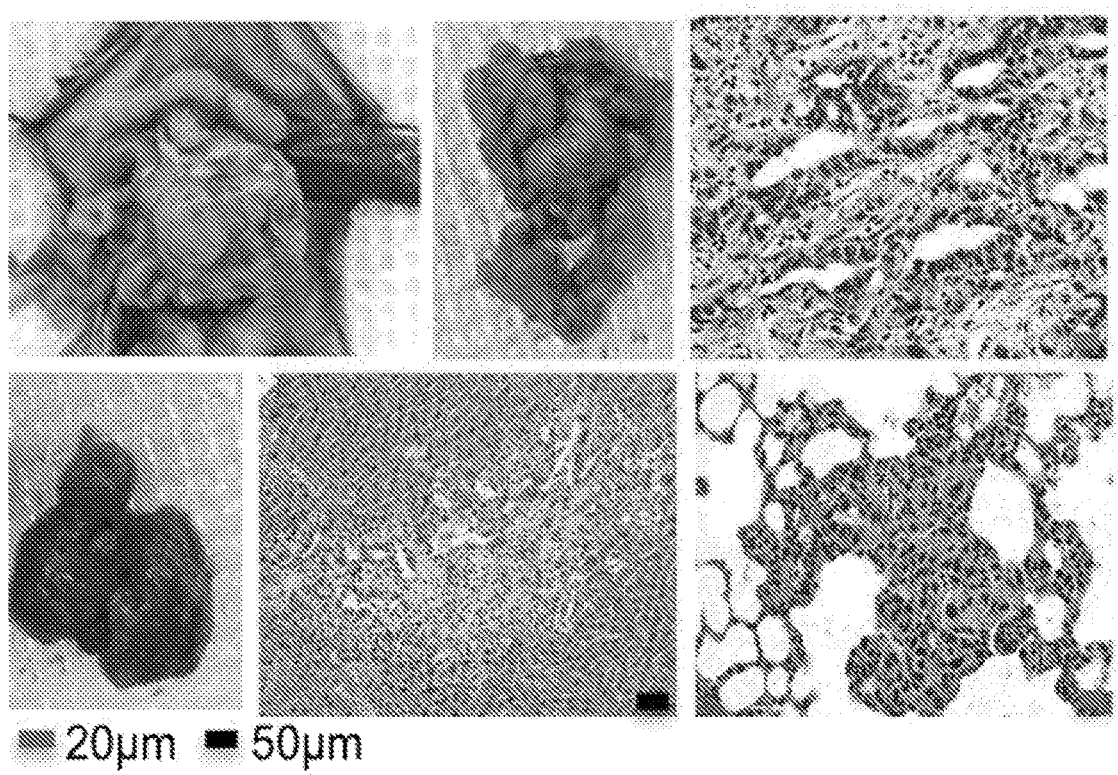
Figure 1E:
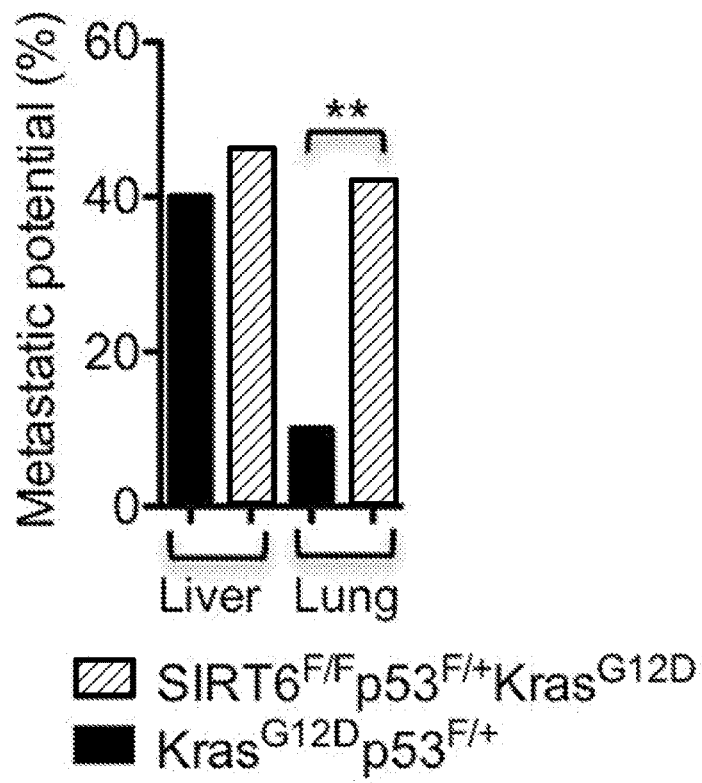
Figure 1F:
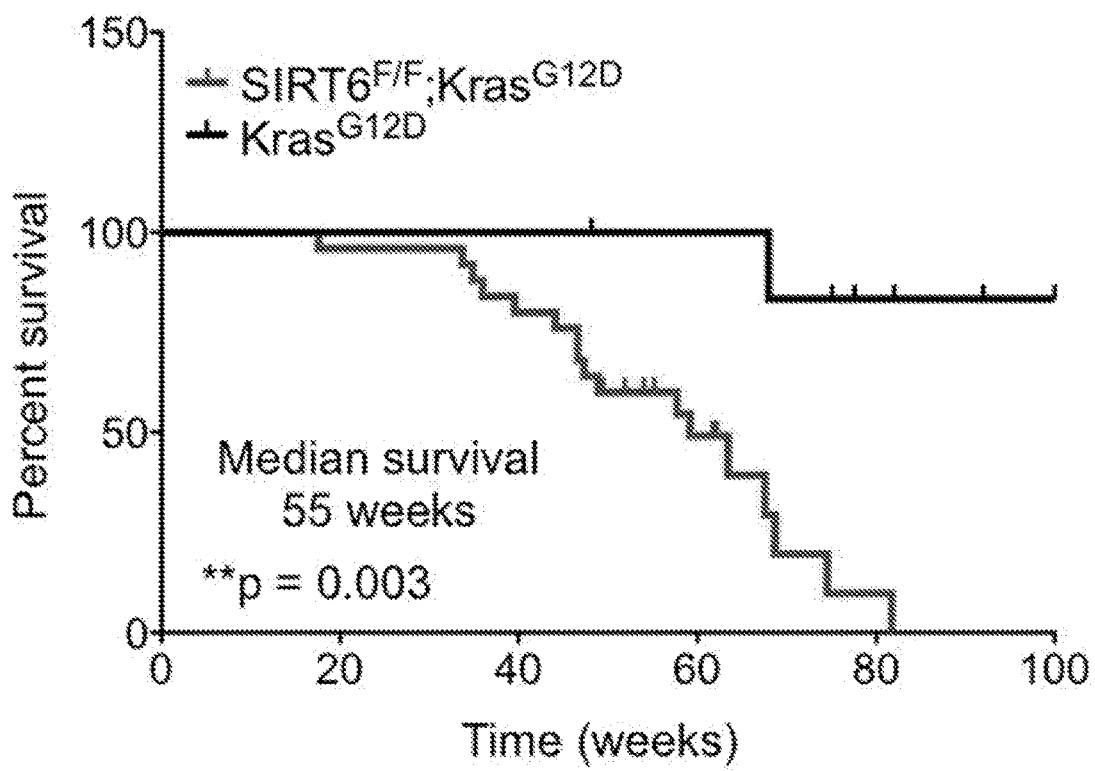
Figure 1G:
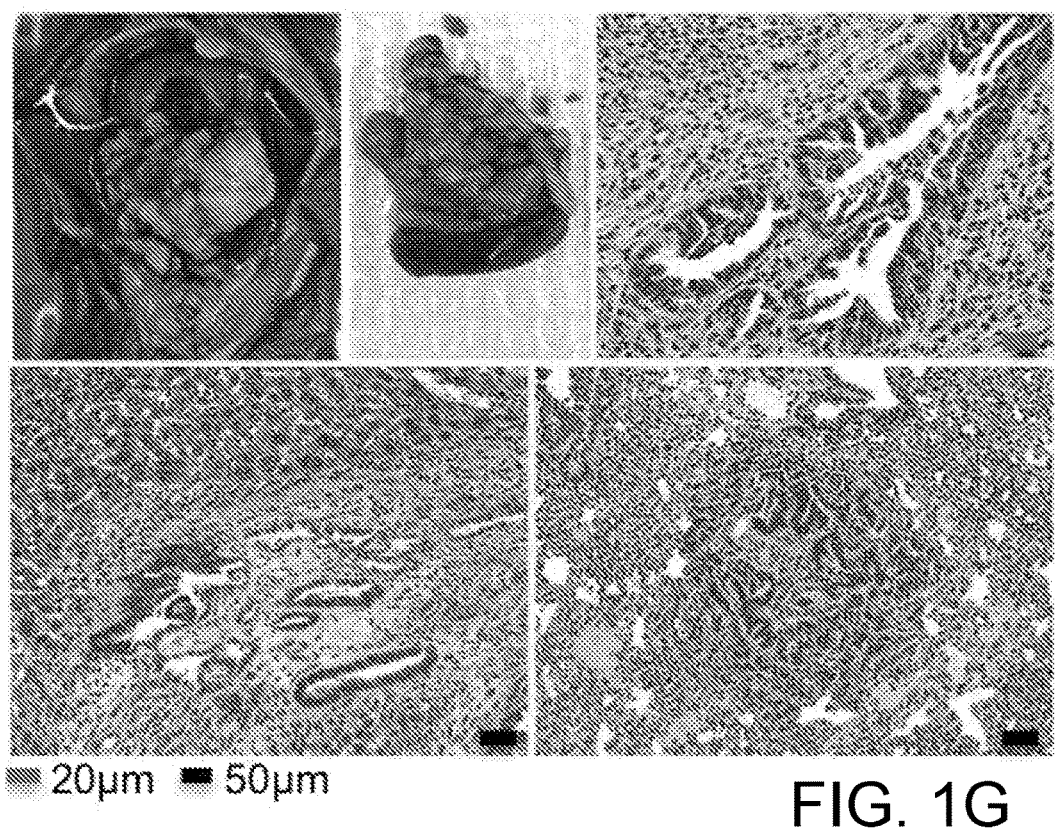
Figure 1H:
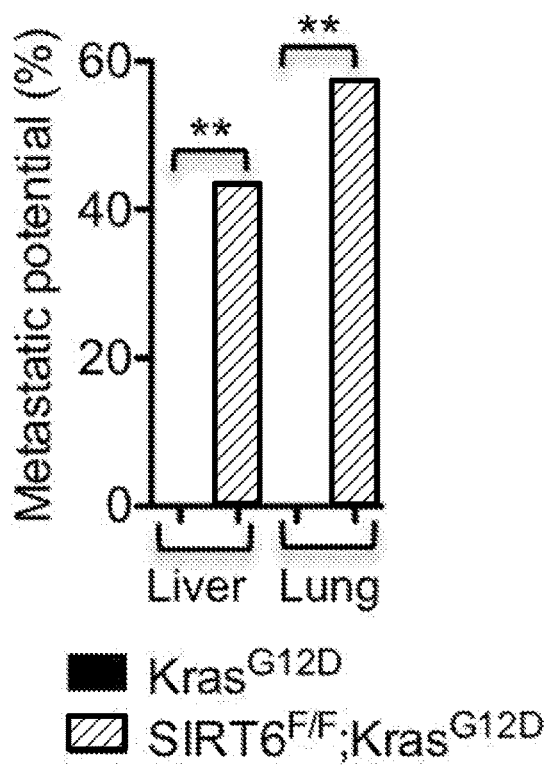

To determine the tissue expression pattern of SIRT6 in human PDAC tumors, tissue microarrays containing 120 pathologist-verified and clinically annotated PDAC samples were generated, including specific cohorts of 40 short-term (<6 months) and 40 long-term (>3 years) survivors. Staining of these samples using a validated antibody for SIRT6 revealed that ~30-40% of PDAC tumors demonstrated reduced SIRT6 expression compared to normal pancreas (FIG. 1A). Although the prognosis for this disease is already quite poor, patients who underwent surgical resection of a SIRT6$^{low}$ PDAC tumor had an even worse prognosis in this retrospective analysis, with a median overall survival of 17.5 months compared to 33 months in the SIRT6$^{high}$ tumors (FIG. 1B). The functional role of SIRT6 by knocking down SIRT6 in human pancreatic ductal epithelial (HPDE) cells was then evaluated. These studies revealed that SIRT6 actively represses both global levels of acetylated H3K56 and cellular proliferation in pancreatic ductal cells, prompting further exploration into the role of SIRT6 in the pathogenesis of PDAC in a physiologic context.

To determine whether SIRT6 delays the development of PDAC in a genetically engineered mouse model (GEMM), Sirt6 conditional knockout mice (Sirt6$^{fl/fl}$) were crossed with mice harboring a pancreas-specific Cre recombinase (p48-Cre), a floxed p53 allele (p53$^{fl/+}$), and a lox-STOP-lox (LSL) Kras$^{G12D}$ allele to generate LSL-Kras$^{G12D}$; p48-Cre mice with specific loss of one or both Sirt6 and p53 alleles in the pancreas. Remarkably, in the context of activated Kras in the pancreas, loss of Sirt6 greatly accelerated the development of lethal pancreatic tumors regardless of p53 status (FIGS. 1C-H). In addition to developing PDAC and high-grade pancreatic intraepithelial neoplasia (PanIN) at an earlier age, Sirt6-deficient tumors had a greater propensity to metastasize to the lung, compared to their Sirt6 wild-type (WT) counterparts (FIGS. 1D-E and 1G-H). Importantly, these results demonstrate that SIRT6 suppresses both the formation and metastasic spread of $KRAS^{G12D}$-driven PDAC and establish SIRT6 as a critical tumor suppressor in this disease.

Figure 2A:
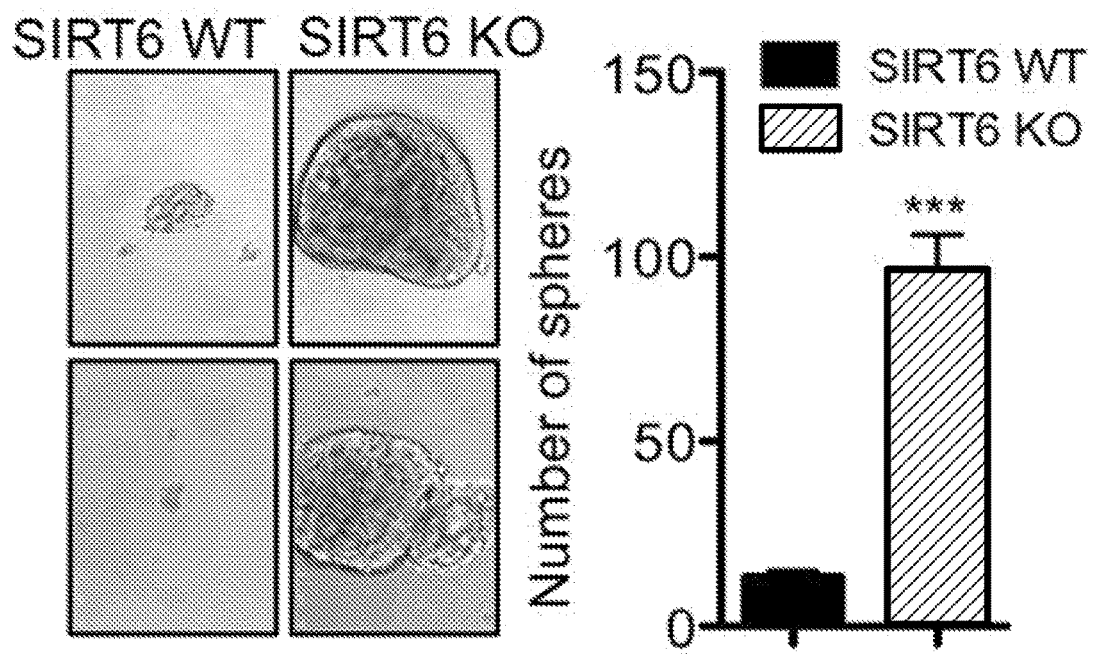
FIGS. 2A-2P are a series of 16 figures showing that SIRT6 suppresses proliferation of established PDAC through histone deacetylation. 2A, Murine PDAC cells were grown under restrictive, nonadherent conditions to induce tumor sphere formation, photomicrographs (left) and quantified (right). Two independent cell lines are represented. 2B-2E, Murine PDAC cells were engineered to express empty vector, SIRT6 WT or SIRT6 HY catalytically inactive mutant. 2B, Immunoblot of chromatin extract and WCL. 2C, Growth curve of a representative SIRT6 KO PDAC line. 2D, Quantification of tumor spheres formed by two independent SIRT6 KO PDAC lines and grown as in 2A. 2E, Tumor weights (left) and gross image of SIRT6 KO PDAC cell line grown for 3 weeks as a subcutaneous xenograft (n=5 per genotype). 2F, Immunoblot of WCL in human PDAC cell lines (below) Image J quantifications of SIRT6/actin ratio.
Figure 2B:
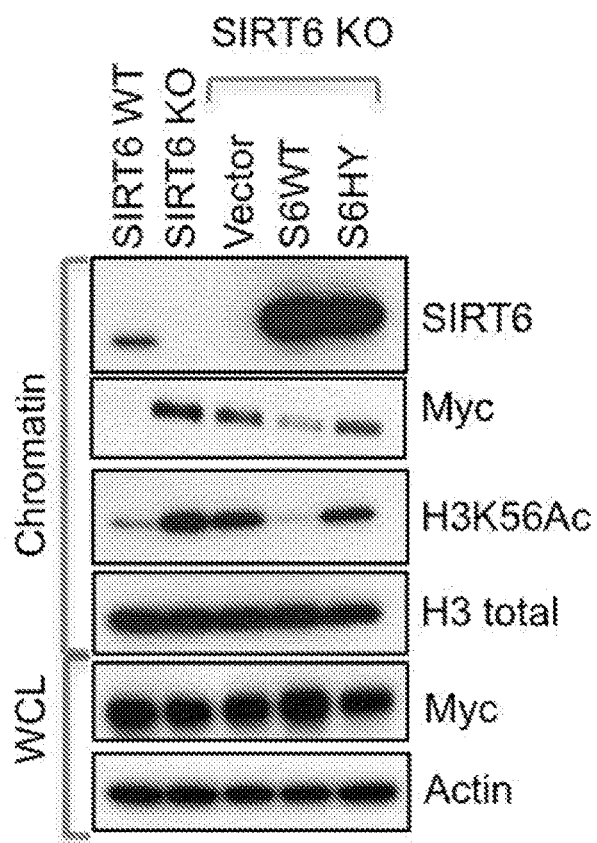
Figure 2C:
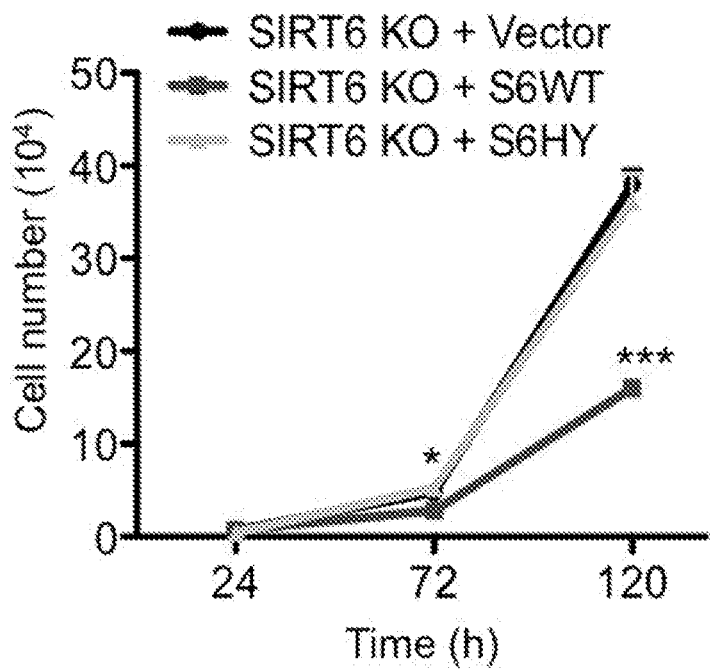
Figure 2D:
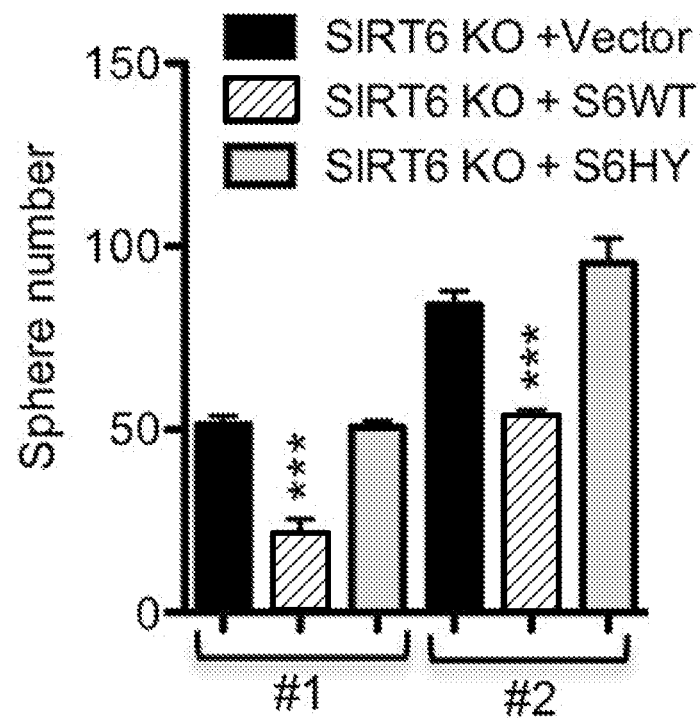
Figure 2E:
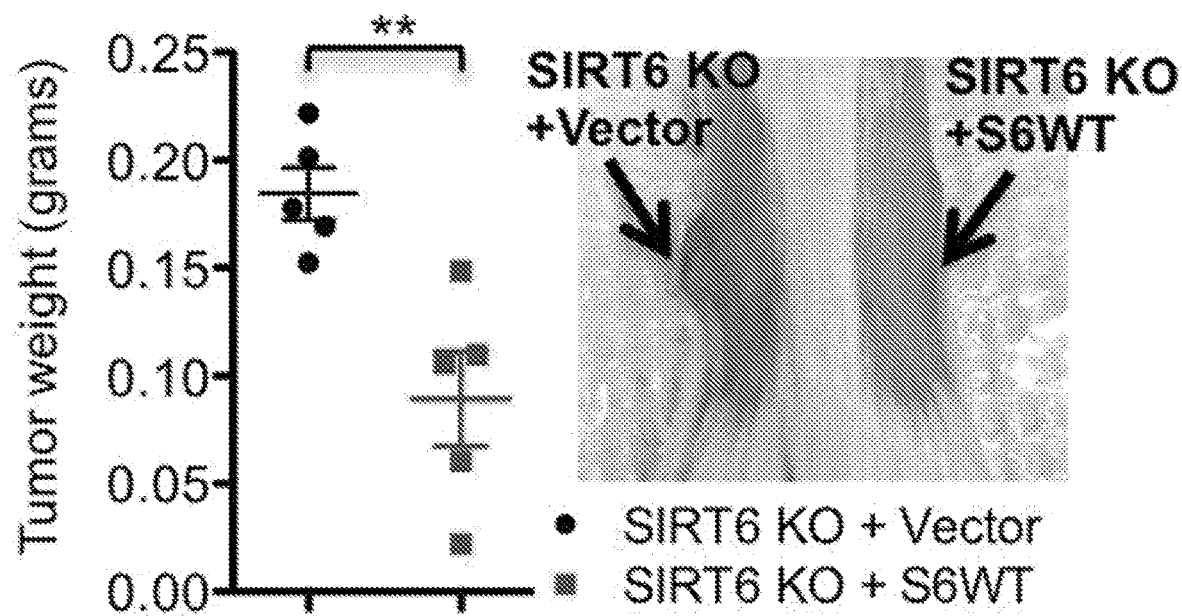
Figure 2F:
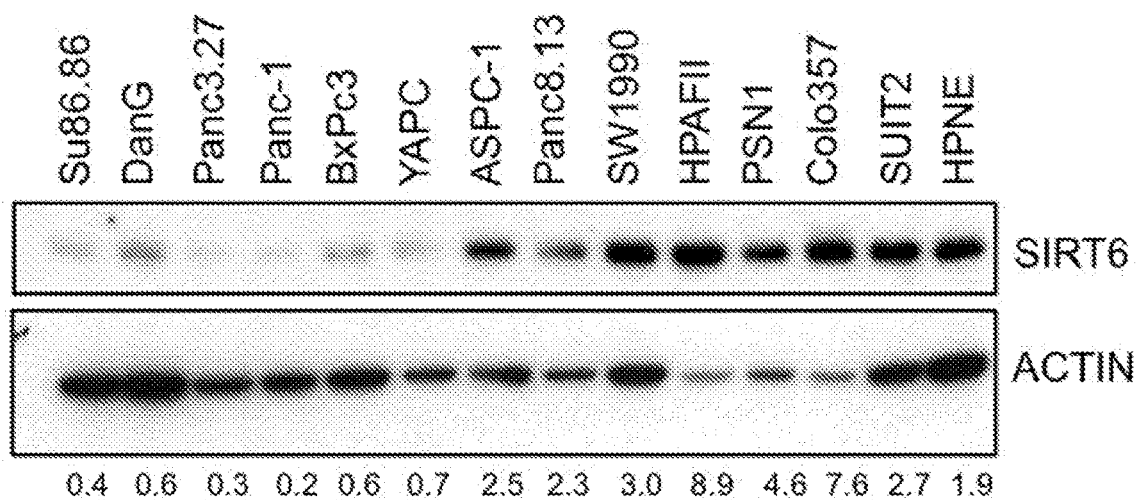
Figure 2G:
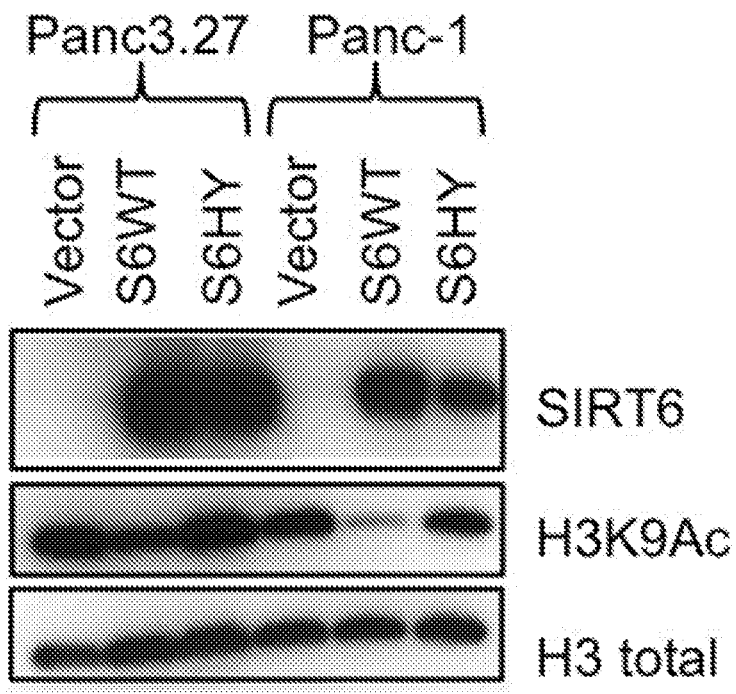
Figure 2H:
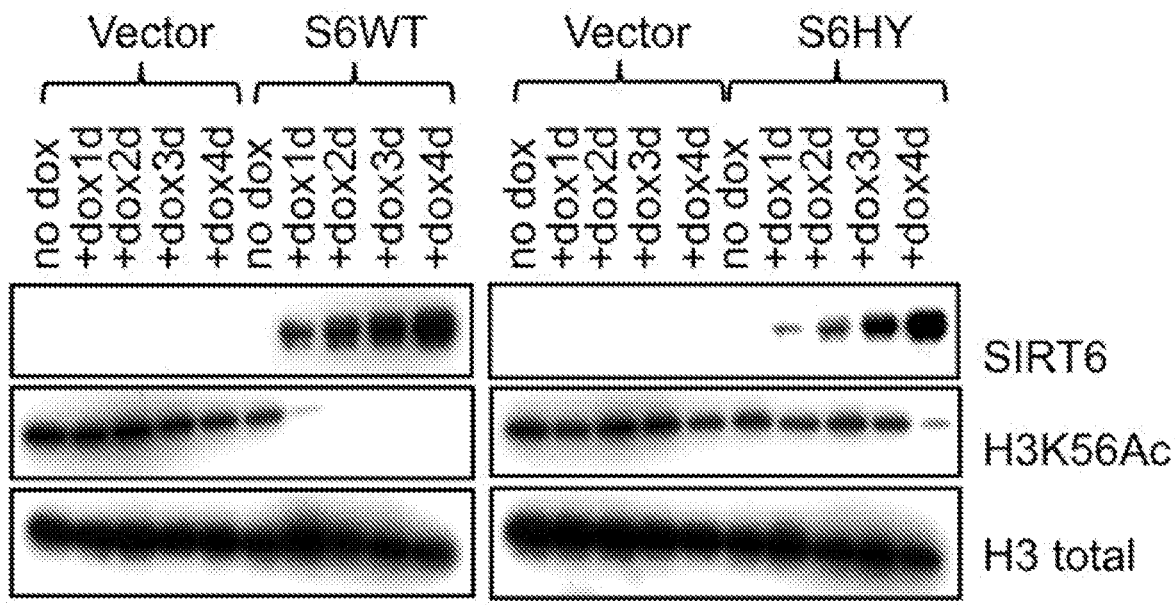
Figure 2I:
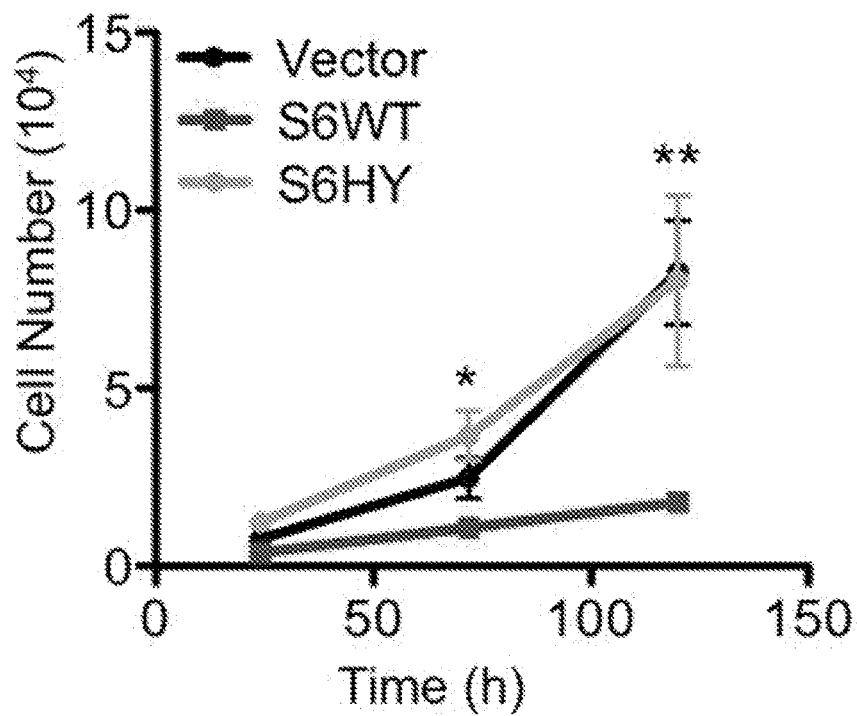
Figure 2J:
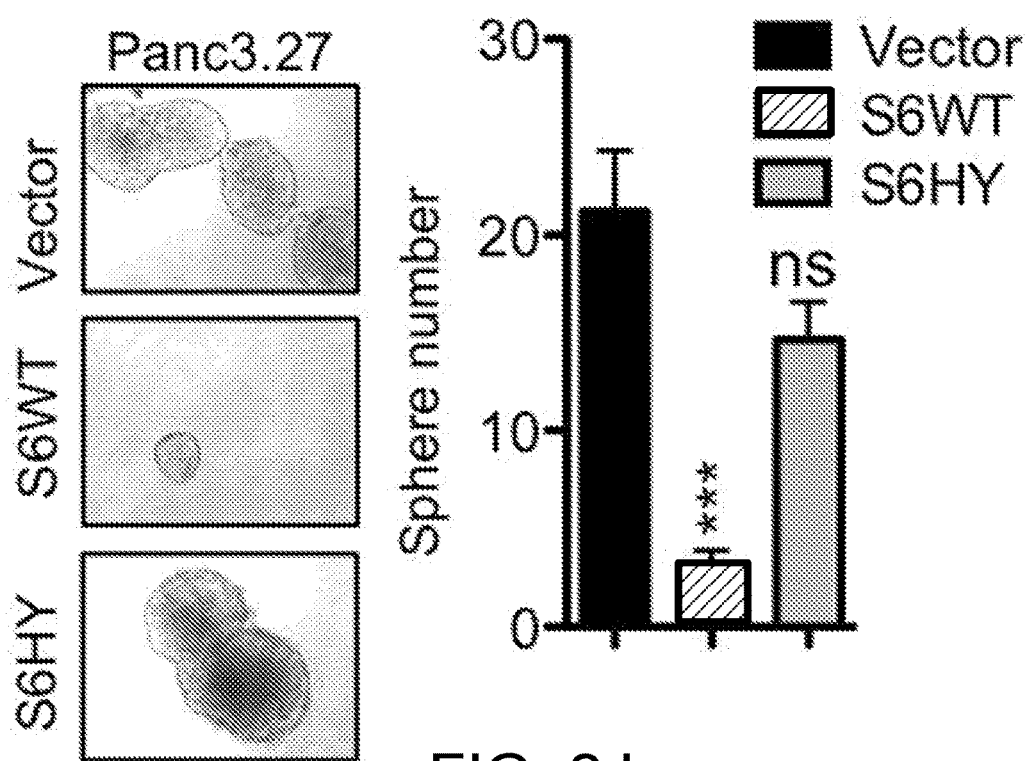

Example 2: SIRT6 Suppresses Proliferation of Established PDAC Though Histone Deacetylation To understand how the loss of this bioenergetic sensor influences the biology of established tumor cells, cell lines were derived from $Sirt6^{f/f}$; $Kras^{G12D}$; $p53^{f/+}$; p48-Cre (SIRT6 KO) and $Sirt6^{+/+}$; $Kras^{G12D}$; $p53^{f/+}$; p48-Cre (SIRT6 WT) murine tumors. Interestingly, SIRT6 KO PDAC cell lines were highly enriched for tumor sphere forming cells compared to SIRT6 WT cells grown under restrictive culture conditions, which suggested an enhanced tumorigenic potential (FIG. 2A). In accordance with the role of SIRT6 as a histone deacetylase and repressor of Myc-mediated transcription (Sebastian et al., 2012), PDAC cells lacking SIRT6 had increased global levels of H3K56Ac as well as increased chromatin-bound Myc compared to SIRT6 WT cell lines, although total levels of Myc in the whole cell lysate were similar between the two genotypes (FIG. 2B). The direct role of SIRT6 histone deacetylase activity in regulating these phenotypes was confirmed by the fact that WT but not catalytically inactive SIRT6 (S6HY) reduced global levels of H3K56Ac, chromatin-bound Myc, cell proliferation and tumor sphere formation (FIGS. 2B-D). Finally, restoration of SIRT6 expression in SIRT6 KO PDAC cells also slowed tumor growth in vivo (FIG. 2E). To validate these findings in human PDAC, SIRT6 levels were analyzed in a panel of patient-derived PDAC lines. Consistent with the analysis of human PDAC tissues, SIRT6 protein levels were reduced in 6 out of 13 (46%) of the human PDAC cell lines surveyed when compared to HPNE cells (FIG. 2F). Restoration of SIRT6 expression in human PDAC cell lines that exhibit reduced levels of SIRT6 ($SIRT6^{low}$) suppressed H3K9Ac and H3K56Ac levels, cell cycle progression and cellular proliferation, while inducing apoptosis and robustly inhibiting tumor sphere formation in a manner that required SIRT6 deacetylase activity (FIGS. 2G-J). Thus, the loss of this $NAD^+$-dependent histone deacetylase leads to hyperacetylation of chromatin and increased cellular proliferation in both normal pancreatic ductal cells and PDAC.

Figure 2K:
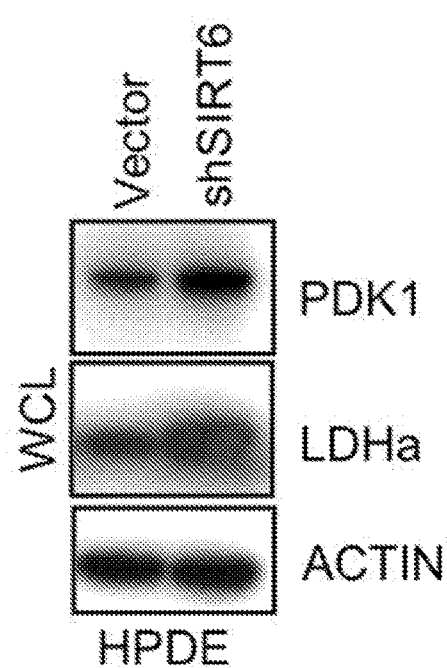
Figure 2L:
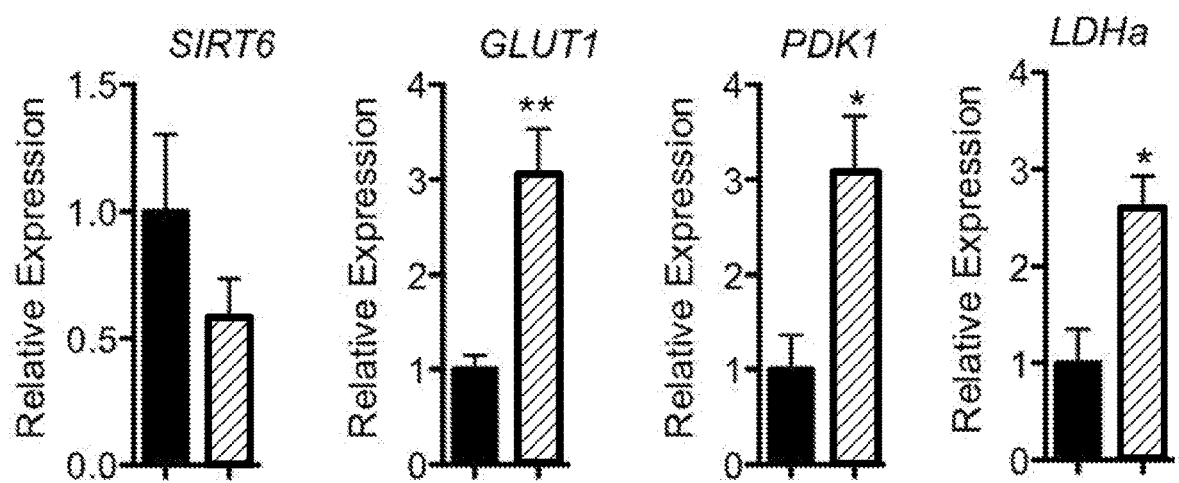
Figure 2M:
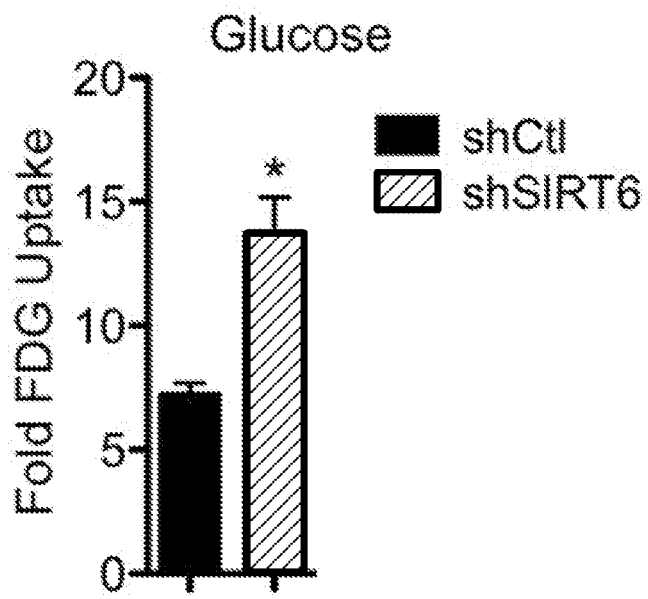
Figure 2N:
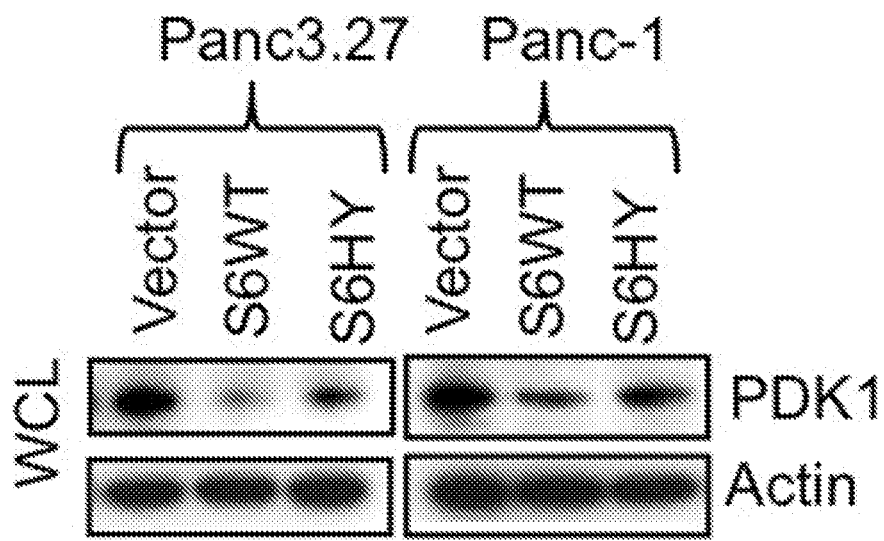
Figure 2O:
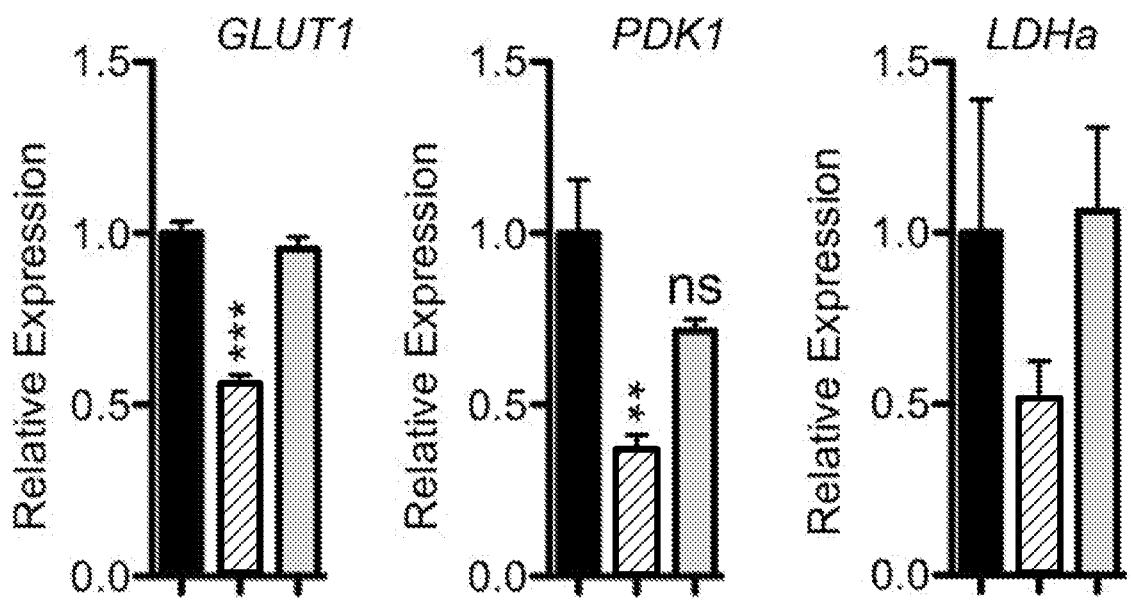
Figure 2P:
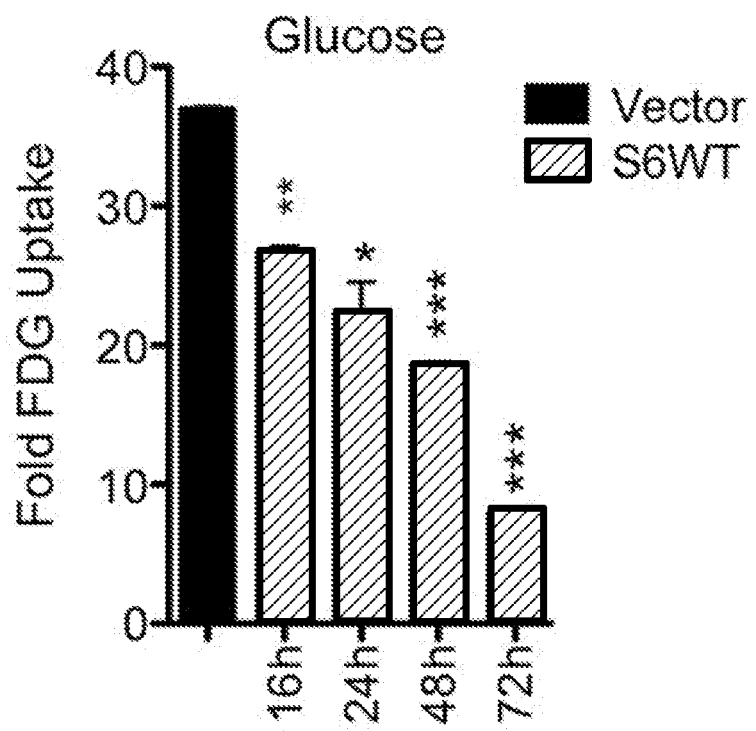

SIRT6 is a central regulator of glycolytic metabolism (Sebastian et al., 2012; Zhong et al., 2010). Consistent with this finding, knockdown of SIRT6 in HPDE cells resulted in increased expression of HIF1α target genes involved in glycolytic metabolism, such as pyruvate dehydrogenase 1 (PDK1), lactate dehydrogenase a (LDHA), and the glucose transporter (GLUT1) (FIGS. 2K and 2L). These gene expression changes corresponded with an increase in uptake of the fluorescently labeled glucose analog 2-(N-7-nitrobenz-2-oxa-1,3,diazol-4-yl)amino)-2-deoxyglucose (2-NBDG) (FIG. 2M). Conversely, when SIRT6 levels were restored in $SIRT6^{low}$ PDAC cell lines, glycolytic gene expression and glucose uptake were all repressed (FIGS. 2N-P). Likewise, SIRT6 KO PDAC cells demonstrated relatively high expression of Pdk1, Ldha and Pfkm as well as 2-NBDG uptake compared to SIRT6 WT cells, and expression of SIRT6 reduced glycolytic gene expression. However, despite these increased levels of glucose uptake and glycolytic gene expression, knocking down Pdk1 or Ldha, both central regulators of glycolytic metabolism, had equivalent effects on SIRT6 WT and KO PDAC cells. In addition, pharmacologic inhibition of PDK1 with the small-molecule PDK1 inhibitor, dichloroacetate (DCA), inhibited growth of both SIRT6 WT and KO PDAC cell lines with similar potency. These results suggested that lack of SIRT6 does not render PDACs more sensitive to glycolysis inhibition. To fully evaluate the role of glycolysis in the accelerated formation of SIRT6 KO PDAC, SIRT6 KO and WT mice were treated with DCA in their drinking water from 4 weeks of age and monitored for the development of lethal PDAC tumors. Consistent with our in vitro results, DCA treatment minimally delayed the onset of SIRT6 KO PDAC. Overall, these results indicate that enhanced glycolysis plays a modest role in the increased aggressiveness of these SIRT6-deficient tumors, in contrast to what was previously observed in colon cancer (Sebastian et al., 2012).

Figure 3A:
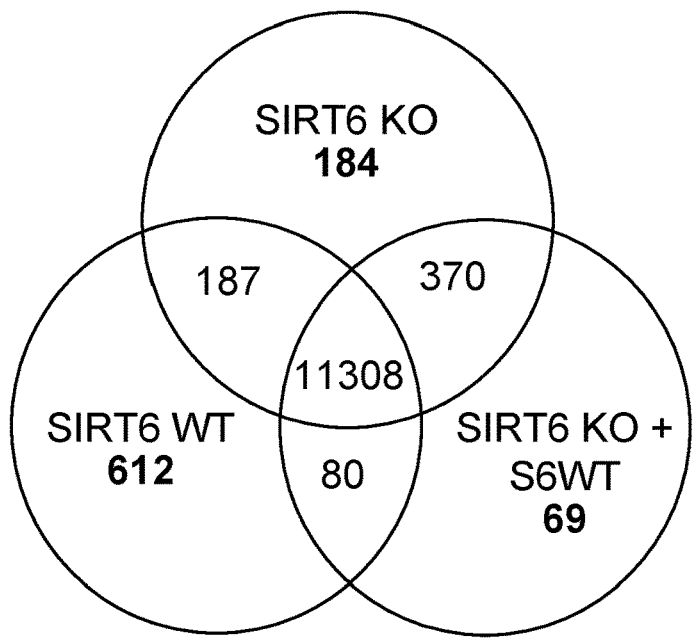
Figure 3B:
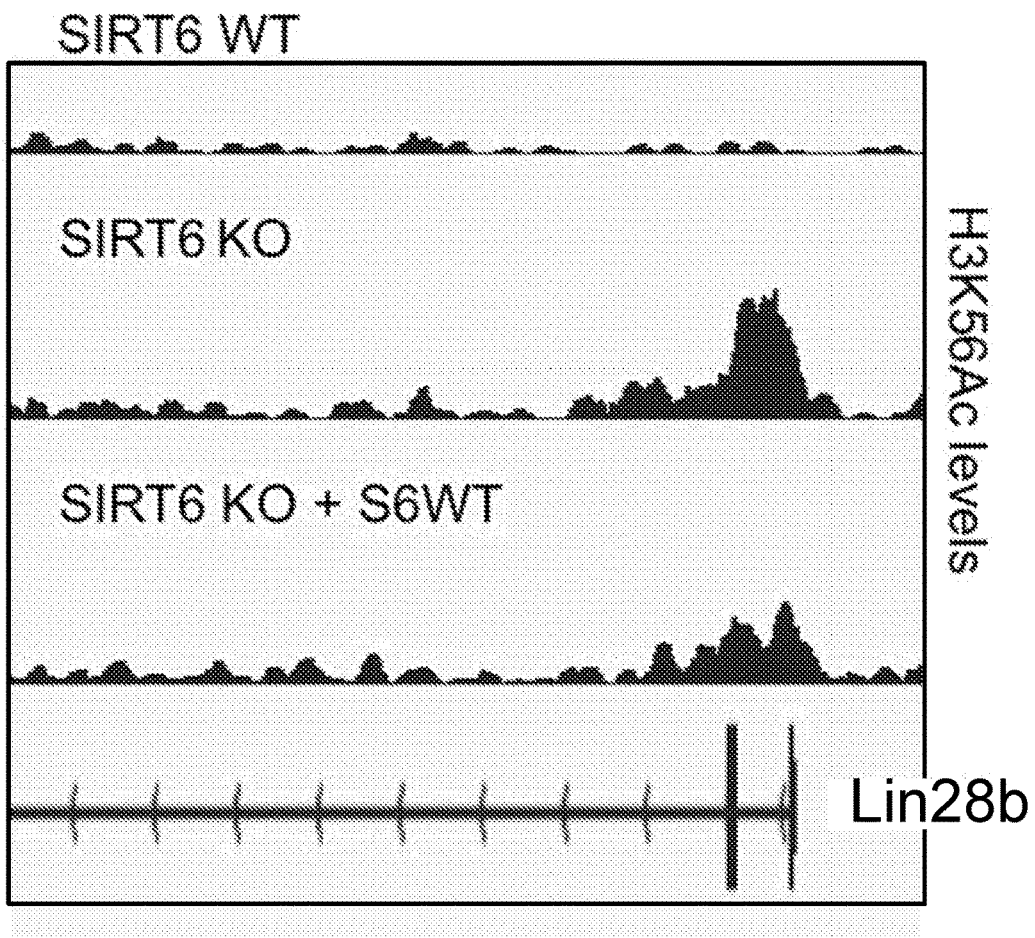

Example 3: SIRT6 Suppresses Expression of the Oncofetal Protein Lin28b in Human and Murine PDAC The resistance of SIRT6 KO PDAC cells to Pdk1 knockdown and the failure to reverse the SIRT6 KO phenotype with DCA treatment prompted us to investigate alternative pathways regulated by SIRT6 that could limit the growth of PDAC cells. Since expression of WT but not catalytically inactive SIRT6 slowed the growth of both human and murine PDAC cells, we hypothesized that these pathways would be regulated by the histone deacetylase activity of SIRT6. We therefore sought to identify novel genes regulated by SIRT6 histone deacetylase activity by performing chromatin immunoprecipitation (ChIP) of H3K56Ac marks (the main chromatin substrate of SIRT6) followed by next generation sequencing (ChIP-seq) on SIRT6 WT and SIRT6 KO murine PDAC cells, as well as SIRT6 KO cells engineered to express WT SIRT6 (SIRT6 KO+SIRT6 WT). In SIRT6 KO cells, a total of 12,049 genes were identified that are decorated with H3K56Ac within 1 kilobase (kb) of their transcription start site. To identify genes that were dynamically regulated by SIRT6, genes were isolated that were only marked in SIRT6 KO cells but not SIRT6 WT cells, and which lost this mark upon re-expression of SIRT6 (FIG. 3A). The remaining 184 gene promoters were then ranked based on fold change of H3K56Ac in SIRT6 KO compared to SIRT6 WT cells. Intriguingly, the RNA-binding protein Lin28b was the top candidate in this list (FIG. 3B).

Although highly expressed in embryonic tissues, Lin28b is fully silenced during differentiation and in healthy adult cells (Moss and Tang, 2003; Rybak et al., 2008; Yang and Moss, 2003), but may be aberrantly reactivated in a variety of human cancers (Iliopoulos et al., 2009; Thornton and Gregory, 2012; Viswanathan et al., 2009). While Lin28b has been correlated with advanced disease and poor prognosis (King et al., 2011; Lu et al., 2009; Viswanathan et al., 2009), its functional role and mechanism of reactivation in human cancer remain poorly understood. Furthermore, neither Lin28b expression, its regulation nor its functional role in PDAC have previously been explored. Although the Myc transcription factor can bind to consensus sequences within the Lin28b promoter (Chang et al., 2009), overexpression of Myc does not seem sufficient to drive its expression, suggesting that additional cofactors or epigenetic modifications are required (Viswanathan and Daley, 2010). The high levels of H3K56Ac over the Lin28b gene promoter in SIRT6 KO PDAC cells prompted us to explore whether loss of the epigenetic modifier SIRT6 may be one such mechanism of reactivation and whether the expression of Lin28b may drive the growth of a specific subset of PDAC.

Figure 3C:
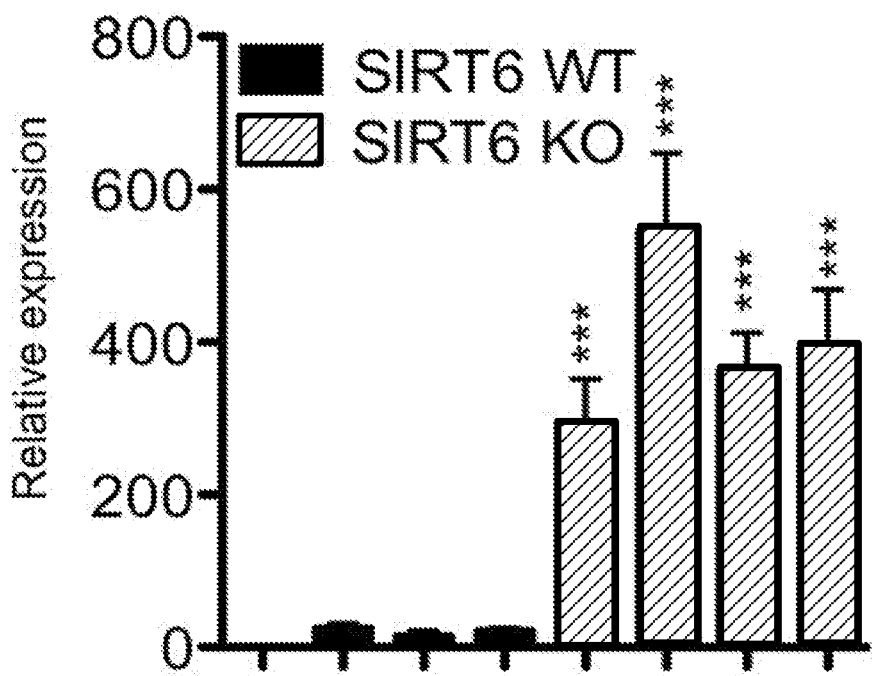
Figure 3D:
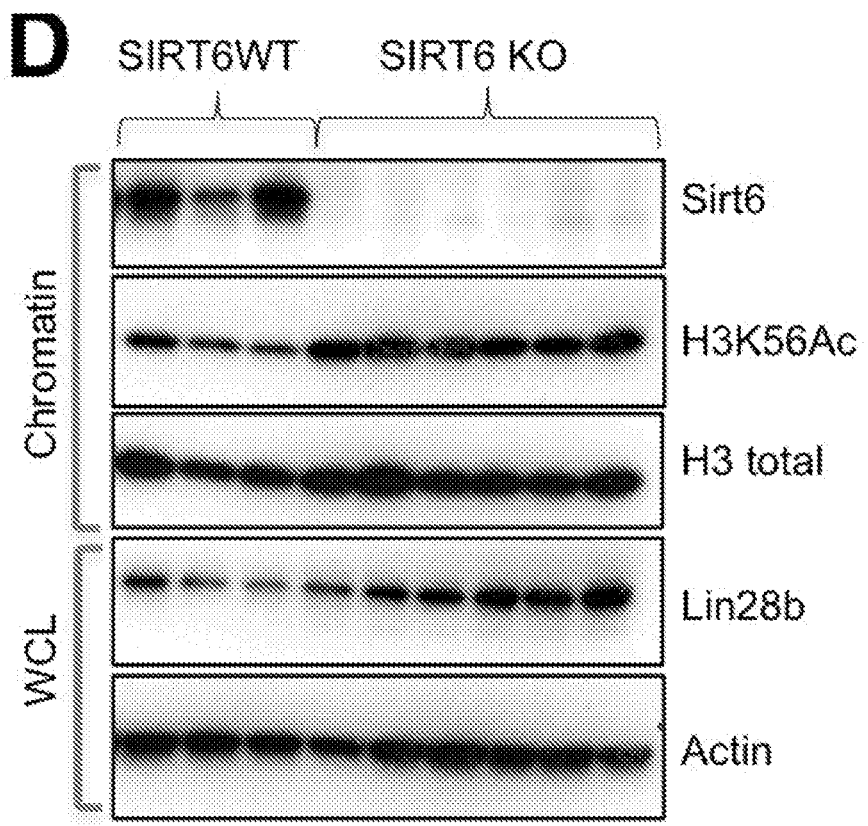
Figure 3E:
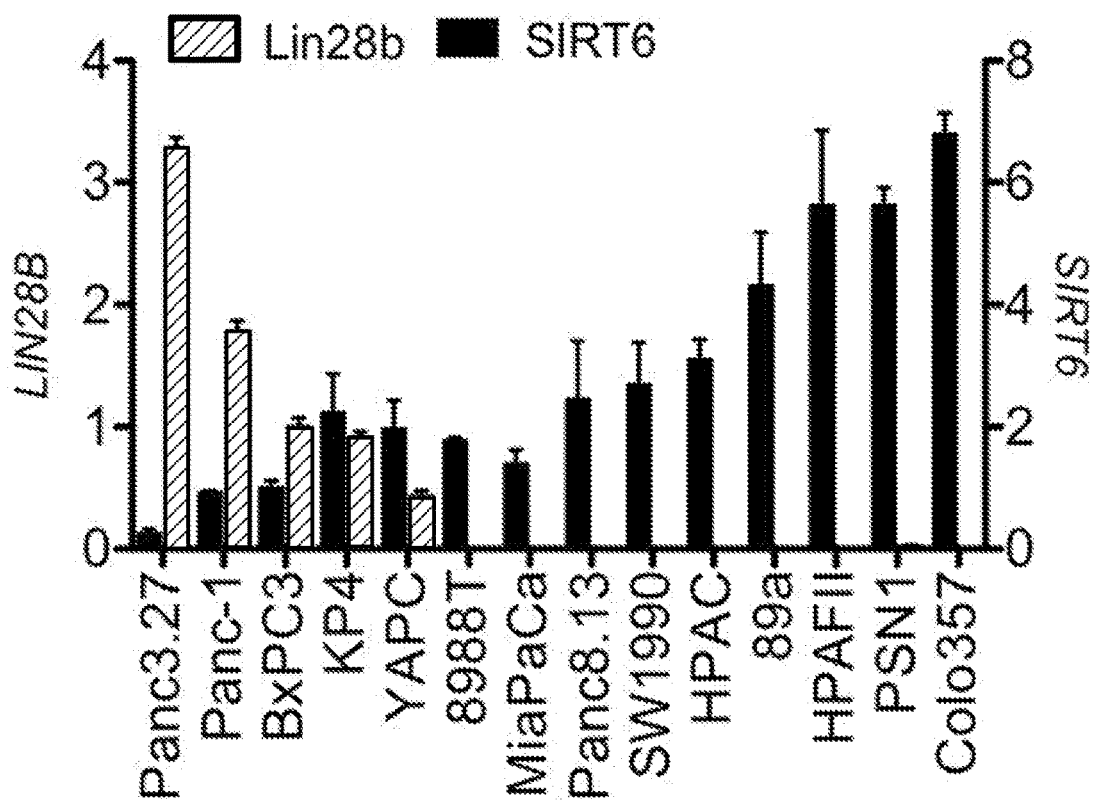
Figure 3F:
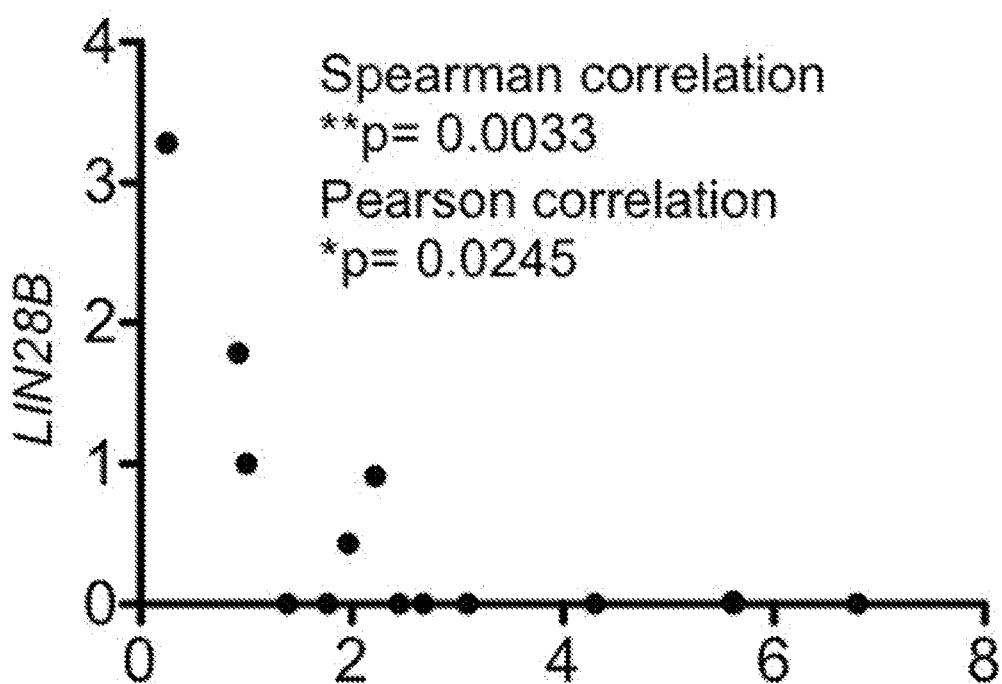
Figure 3G:
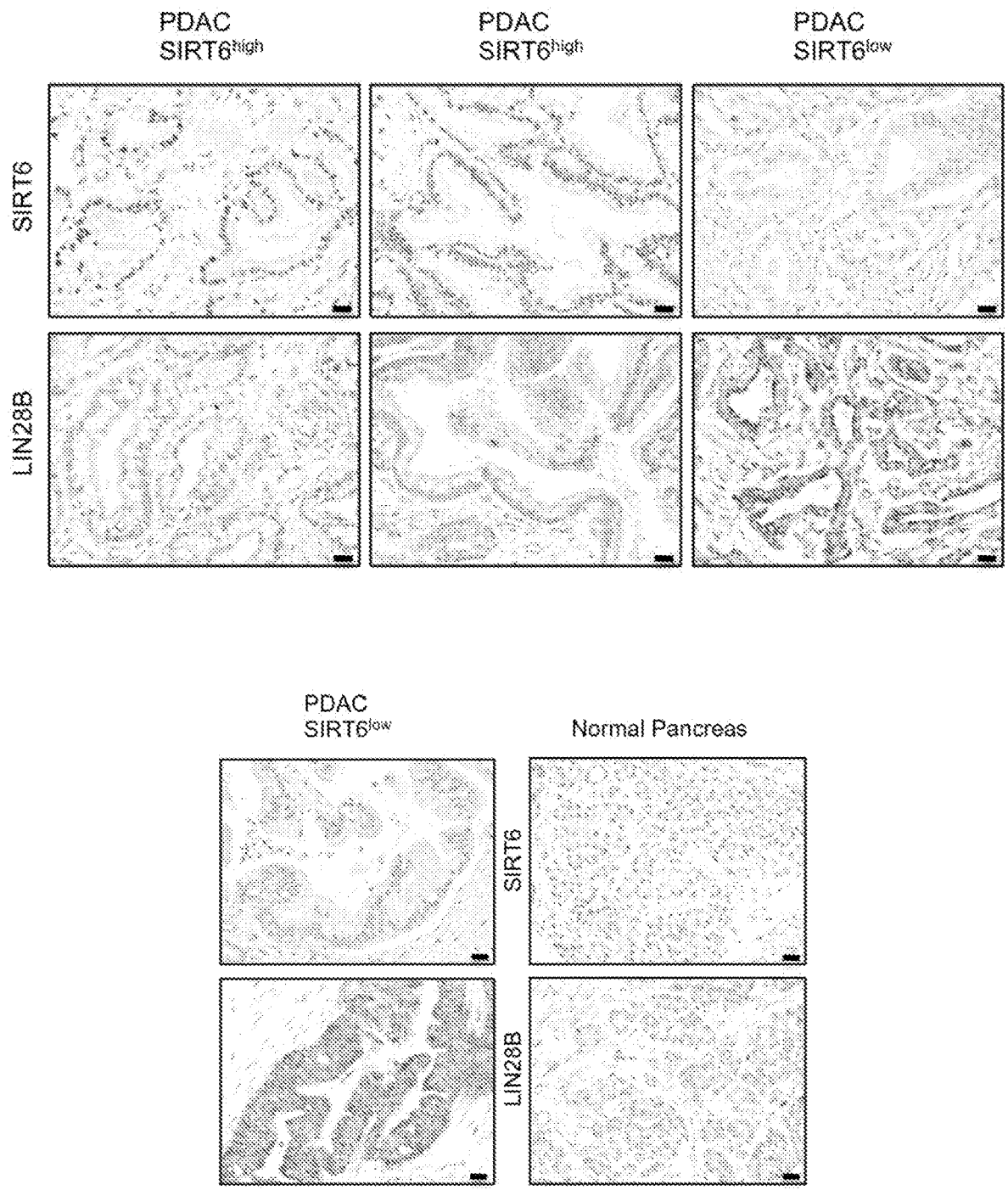

Strikingly, all SIRT6 KO PDAC mouse lines analyzed exhibited far higher Lin28b expression than SIRT6 WT PDAC lines, both at the RNA and protein level (FIGS. 3C and 3D). Similar differences were seen in vivo, as PDAC tumors from SIRT6 KO mice were also universally positive for LIN28B, while SIRT6 WT PDAC tumors demonstrated only background levels of staining for LIN28B by immunohistochemistry. Remarkably, expression of SIRT6 and LIN28B were also inversely correlated in human PDAC cell lines by quantitative real-time PCR (qRT-PCR) (FIGS. 3E and 3F). To define the physiological significance of these observations, expression of LIN28B was analyzed directly in our panel of 120 human PDAC patient samples. Consistently, tumors with low or undetectable levels of SIRT6 exhibited robust staining for LIN28B (FIG. 3G). Lastly, ectopic expression of WT, but not catalytically inactive SIRT6, suppressed expression of LIN28B in Panc3.27 cells (FIGS. 3H and 3I) and in 2 independent murine SIRT6 KO PDAC lines (FIG. 3J) confirming that loss of SIRT6 leads to the reactivation of Lin28b in both human and murine PDAC. Interestingly, SIRT6 may also regulate Lin28b expression in non-epithelial tissues as restoration of SIRT6 reversed the elevated levels of Lin28b expression observed in an immortalized murine embryonic fibroblast (MEF) cell line (Mostoslaysky et al., 2006).

Figure 4A:
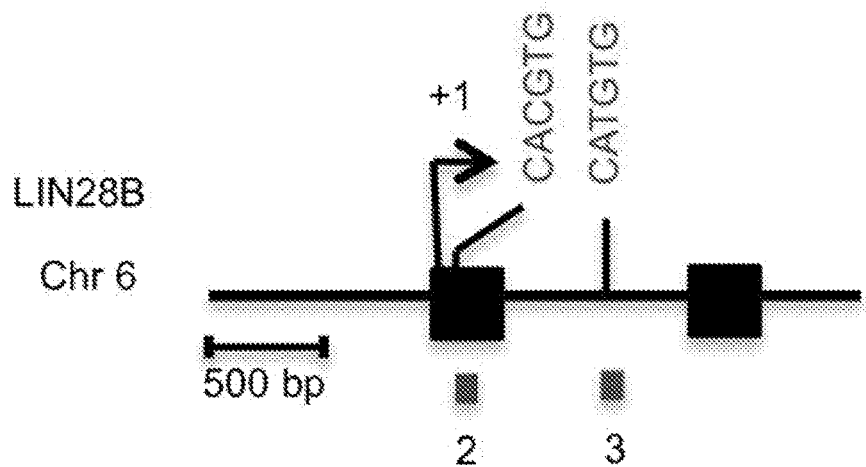
Figure 4B:
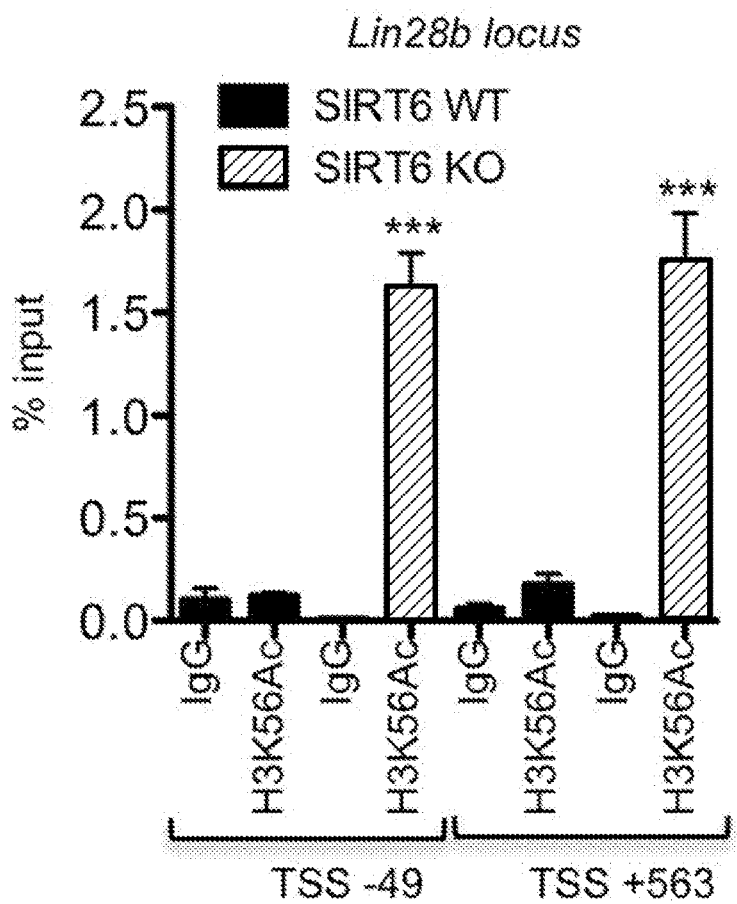
Figure 4C:
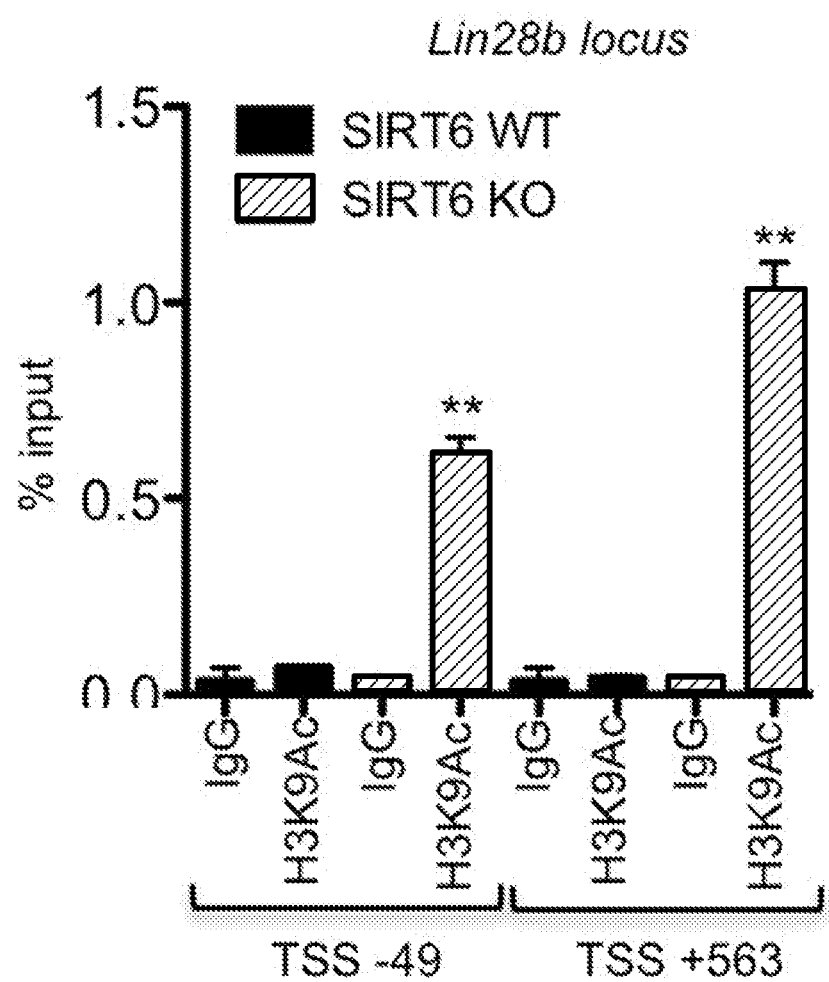
Figure 4D:
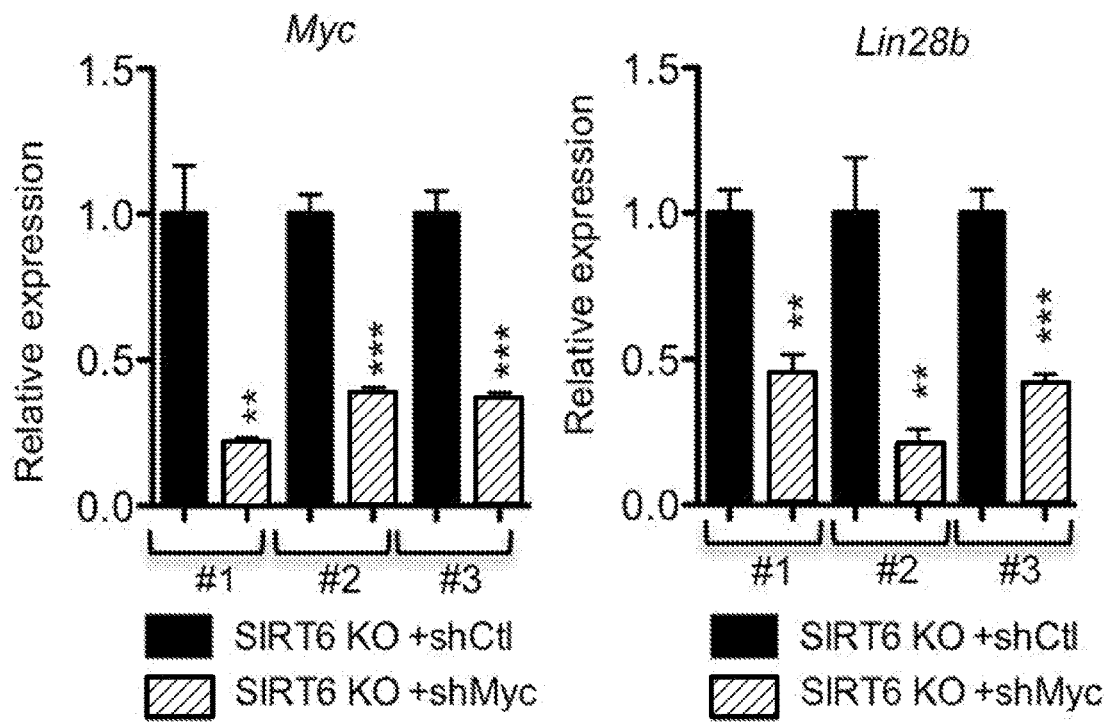
Figure 4E:
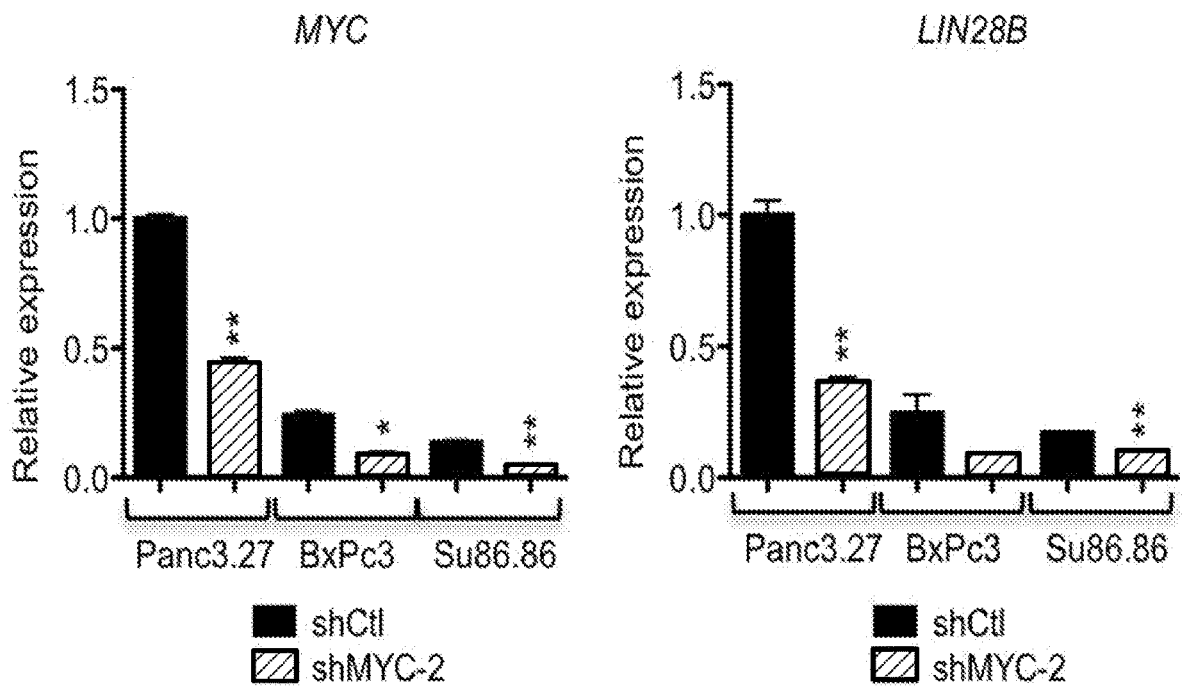
Figure 4F:
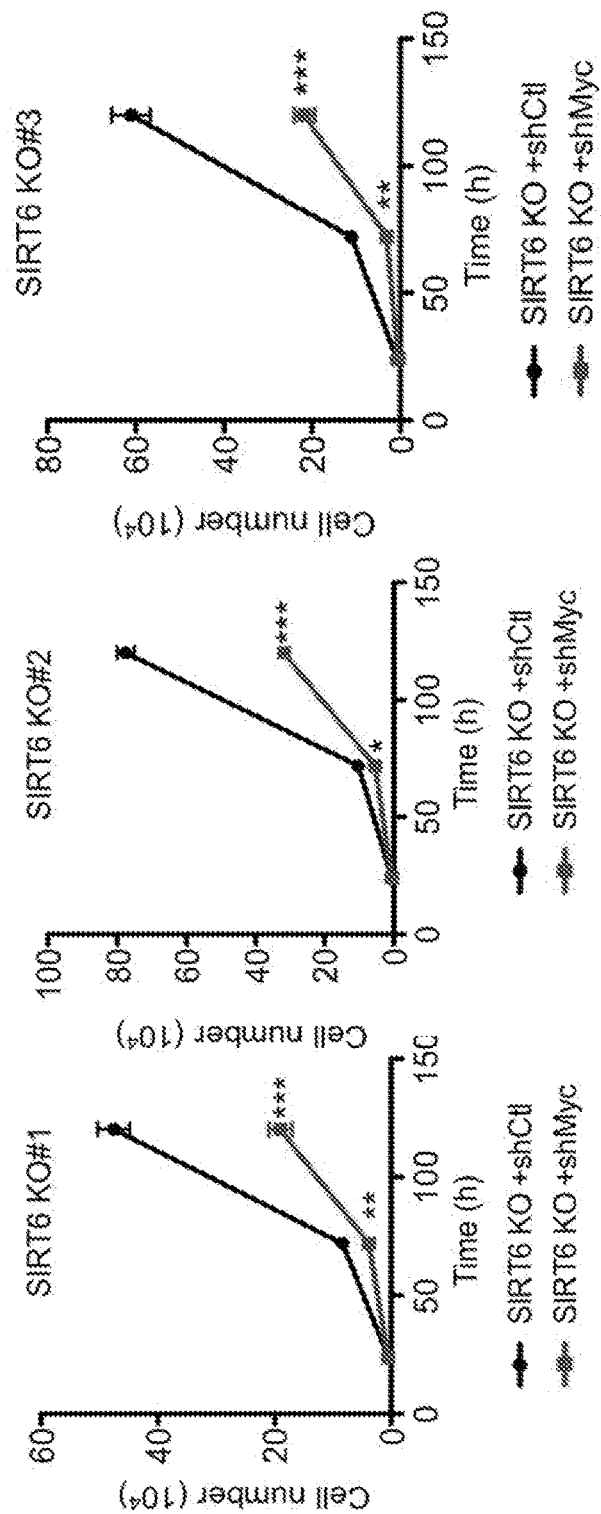
Figure 4G:
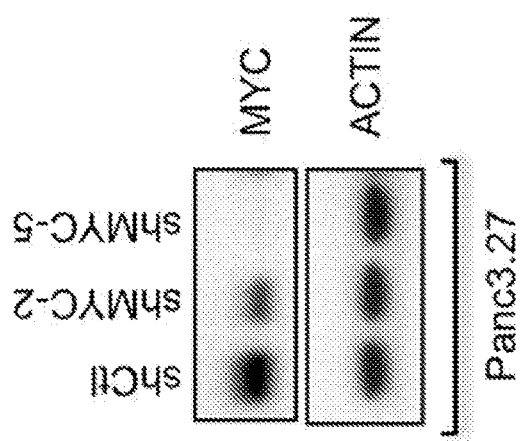
Figure 5A:
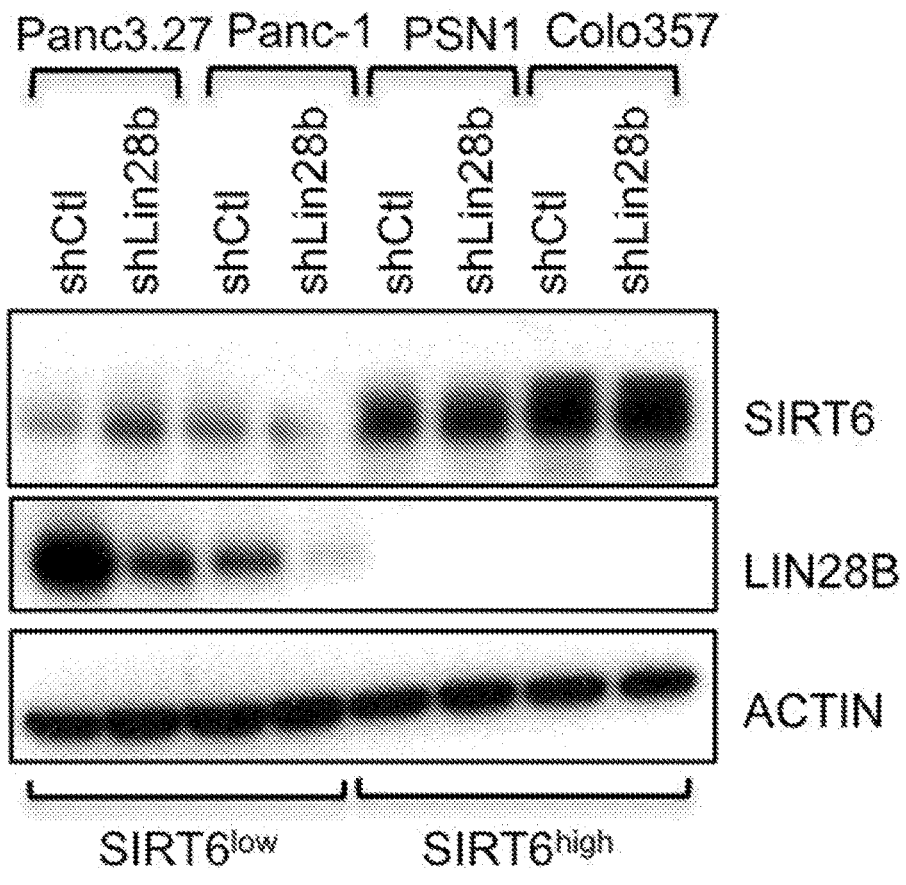
Figure 5B:
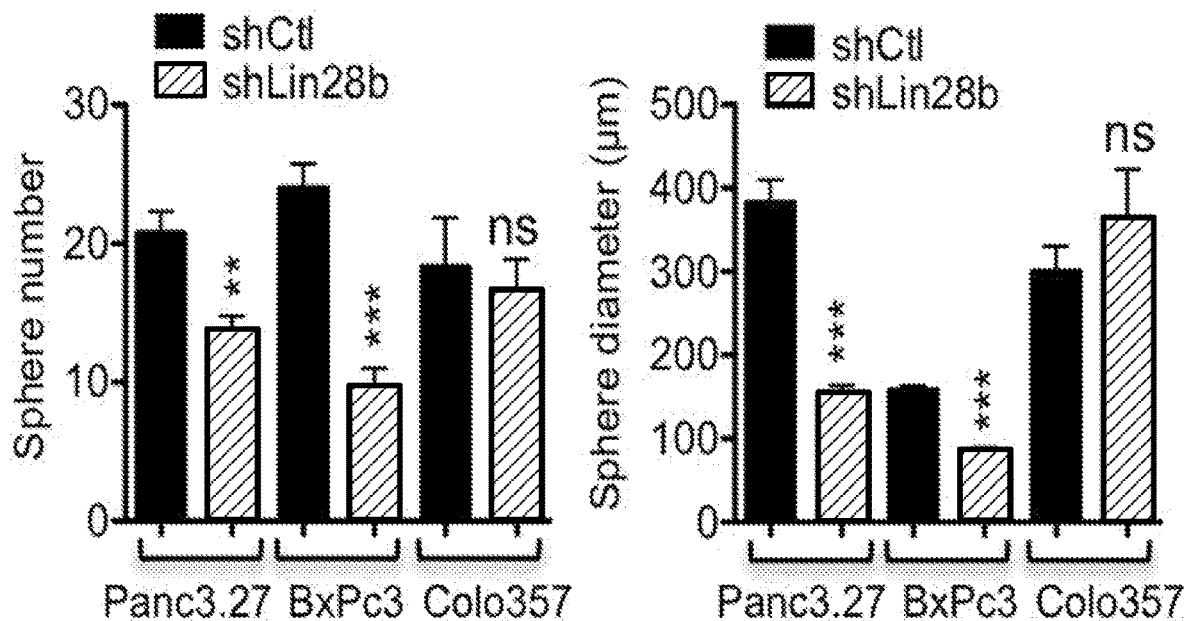
Figure 5C:
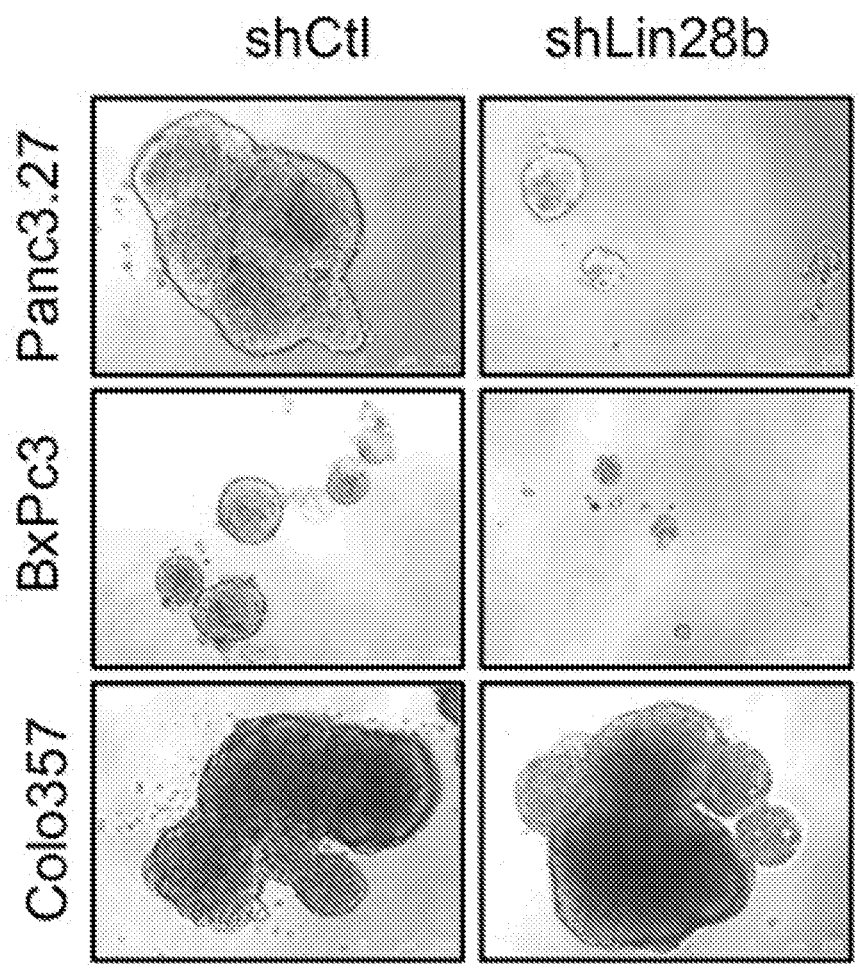
Figure 5D:
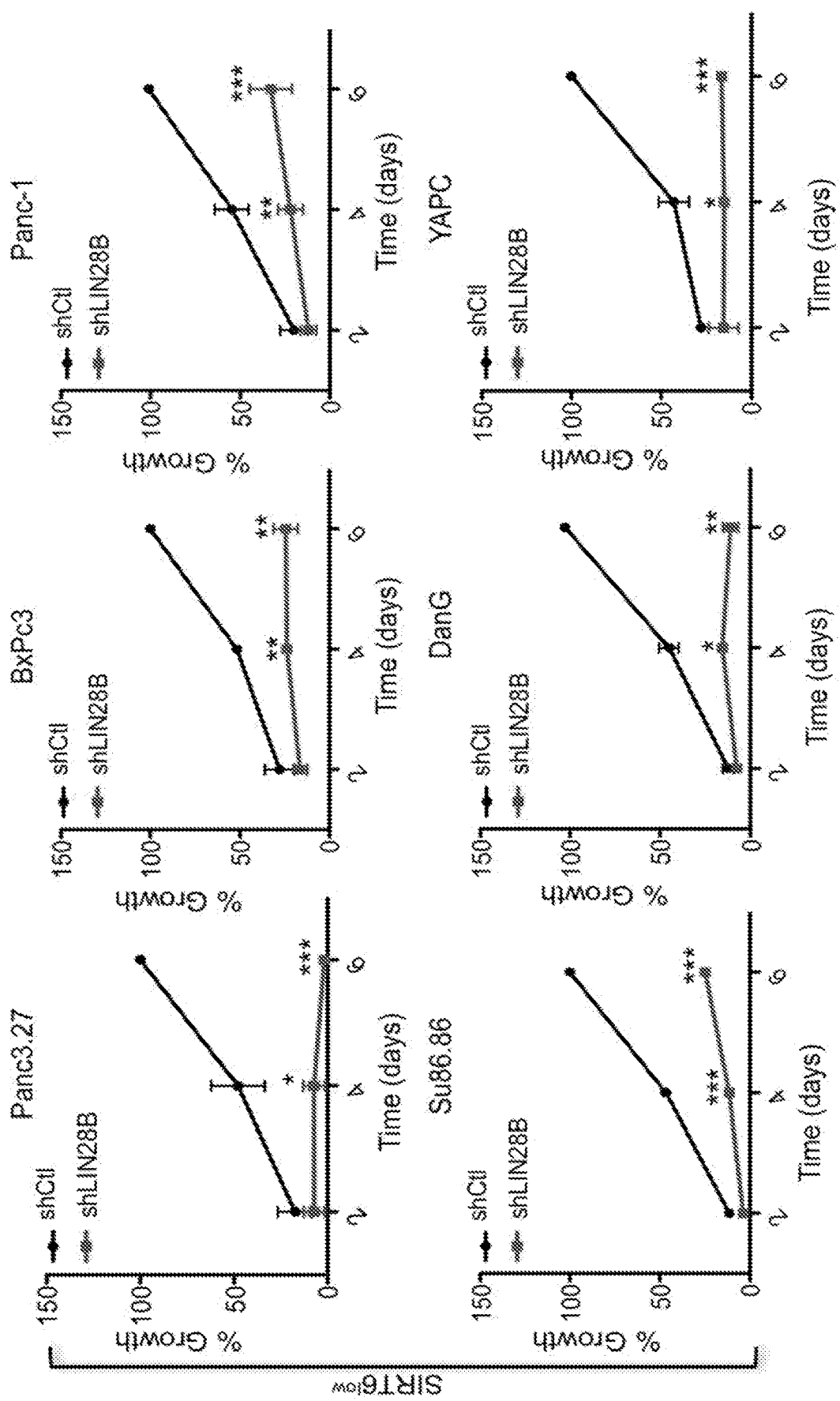
Figure 5E:
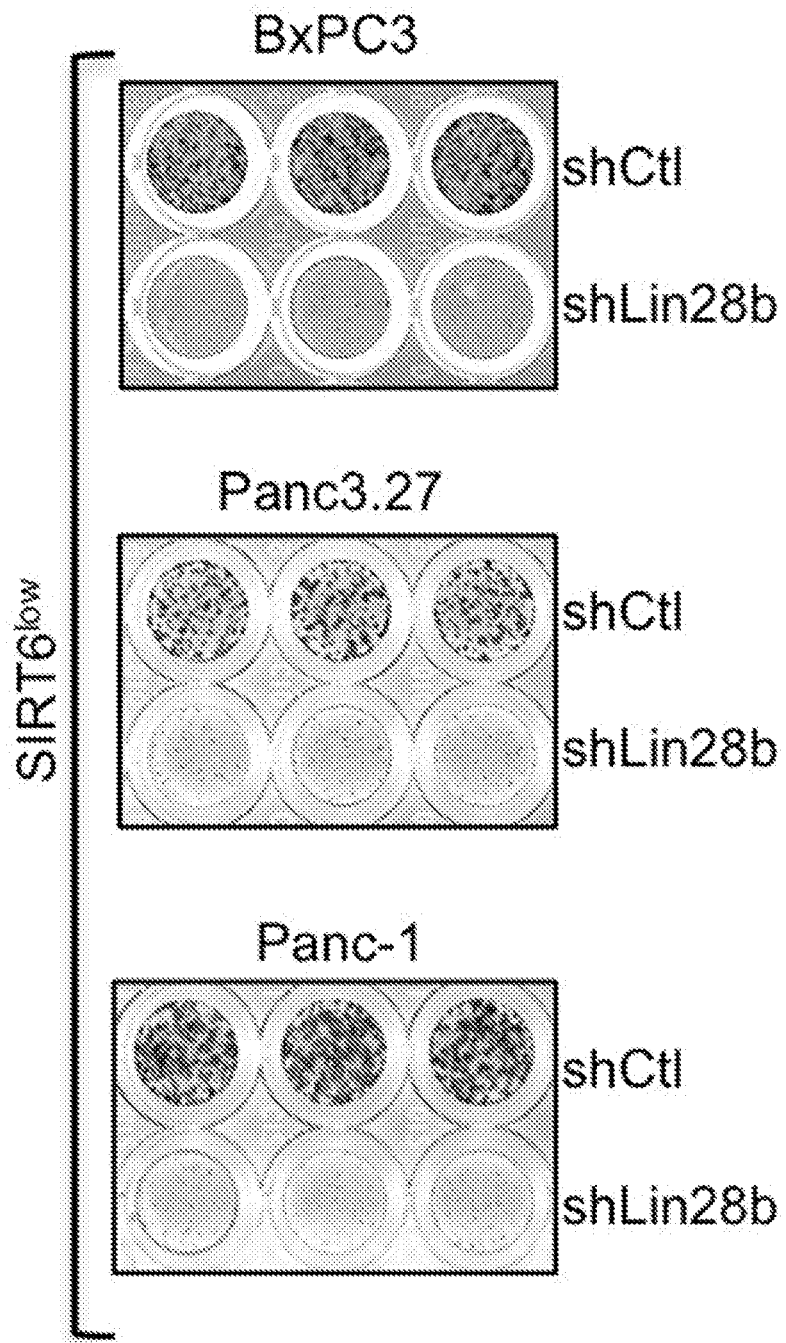
Figure 5H:
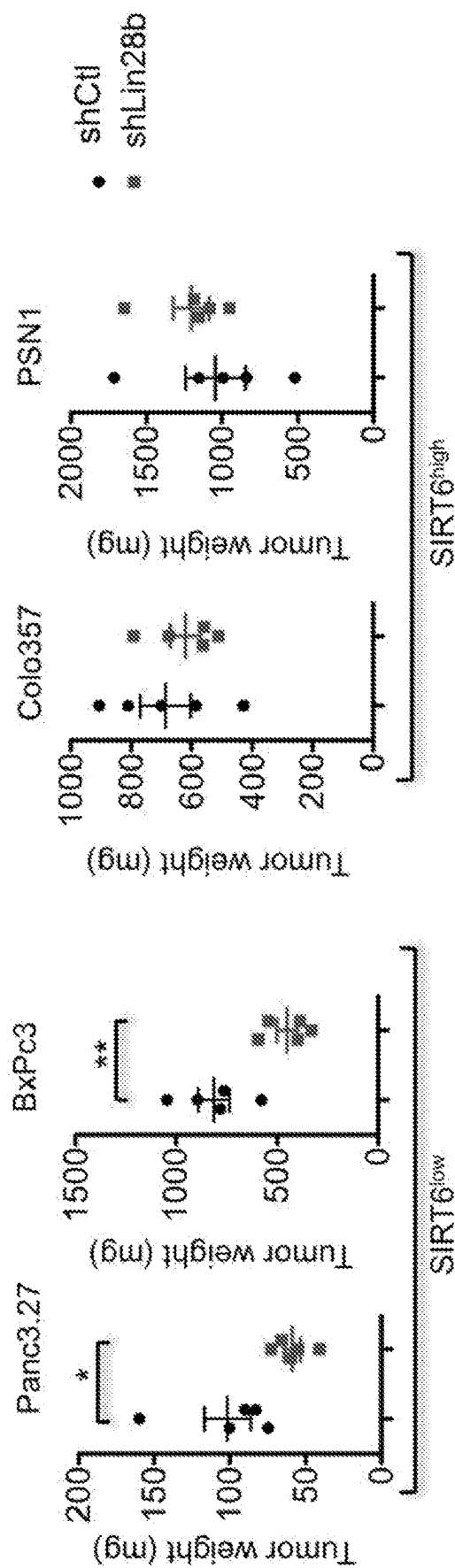

Example 4: SIRT6 Co-Represses Myc-Driven Transcription of Lin28b Through Histone Deacetylation SIRT6 represses Myc-dependent transcription by deacetylating histone marks, resulting in an inaccessible chromatin structure (Sebastian et al., 2012). Therefore, chromatin immunoprecipitation (ChIP) assays were used to interrogate whether SIRT6 may co-repress Myc at the Lin28b locus. Interestingly, SIRT6 KO cells had significantly increased levels of H3K56Ac and H3K9Ac compared to SIRT6 WT cells at two known Myc binding sites within the Lin28b promoter, suggesting an open and permissive chromatin conformation (FIGS. 4B-C). Direct binding of SIRT6 to these Myc binding sites within the Lin28b promoter was confirmed in SIRT6 KO MEFs transfected with either WT SIRT6 or S6HY, whereas only WT SIRT6 could remove H3K56Ac and H3K9Ac marks in this region. Furthermore, we found that this was a dynamic and constitutive process in human PDAC cells with high levels of SIRT6 (SIRT6$^{high}$), such as COLO357 cells, where acute loss of SIRT6 by shRNA-mediated knockdown resulted in increased H3K9 and H3K56 acetylation in a homologous region of the human LIN28B promoter. The critical role of Myc in driving Lin28b expression in PDAC was confirmed by knocking down Myc in three independent SIRT6 KO murine and SIRT6$^{low}$ human PDAC cell lines, which resulted in a consistent and proportional reduction in Lin28b expression (FIGS. 4D and 4E). Consistent with their antagonistic relationship, Myc knockdown phenocopied restoration of SIRT6 expression in both SIRT6 KO murine and SIRT6$^{low}$ human PDAC cells, where reduced cellular proliferation rates and tumor sphere formation were observed (FIGS. 4F-J). Taken together, these data strongly support a mechanism by which SIRT6 actively co-represses Myc-dependent transcription in both human and murine PDAC specifically at the Lin28b locus, through deacetylation of H3K56 and H3K9 chromatin marks.

Example 5: SIRT6$^{low}$ PDAC Cells are Addicted to Lin28b

The functional role of Lin28b in SIRT6 KO murine PDAC cells and SIRT6$^{low}$ human PDAC cells were examined by knocking down Lin28b with both shRNA and siRNA, which resulted in potent suppression of cell proliferation and tumor sphere formation in two independent murine SIRT6 KO cell lines, while two independent SIRT6 WT PDAC lines were completely insensitive to the same treatment. More importantly, both shRNA and siRNA against LIN28B also markedly reduced the proliferation, tumor sphere forming ability and in vivo xenograft growth of several human SIRT6$^{low}$ PDAC lines without any discernable effect on the growth of human PDAC lines with normal levels of SIRT6 (SIRT6$^{high}$) (FIGS. 5D-H). As with restoration of SIRT6 expression, knockdown of Lin28b led to both G1 cell cycle arrest and induction of apoptosis in two independent SIRT6$^{low}$ lines. Thus, LIN28B is both upregulated and critically required for the growth and survival of this subset of PDAC cancers, as defined by loss of SIRT6 expression.

Example 6: Let-7 Suppresses Igf2bps and Hmga2 Expression and PDAC Cell Growth The most well-characterized function of Lin28b is to inhibit the biogenesis of a family of 12 tumor suppressor microRNAs (miRNAs), collectively referred to as let-7 (Heo et al., 2008; Newman et al., 2008; Pasquinelli et al., 2000; Rybak et al., 2008; Viswanathan et al., 2008). Mature let-7 miRNAs are found in a reciprocal pattern with Lin28b, suppressed in embryonic tissues and highly expressed in normal adult cells (Bussing et al., 2008; Moss and Tang, 2003; Rybak et al., 2008; Yang and Moss, 2003), where it can promote the degradation of a number of targets involved in carcinogenesis (Johnson et al., 2005; Mayr et al., 2007; Sampson et al., 2007), including Insulin Growth Factor 2 Binding Proteins (IGF2BPs) and High Mobility Group AT-Hook 2 (HMGA2) (Boyerinas et al., 2008; Mayr et al., 2007; Nguyen et al., 2014; Park et al., 2007; Polesskaya et al., 2007). To determine whether Lin28b may drive the growth and survival of PDAC cells through the inhibition of let-7, the levels of let-7 miRNA family members were measured following Lin28b knockdown in our human SIRT6$^{low}$ PDAC cells. Indeed, the expression of almost all let-7 family members increased following Lin28b knockdown. To assess the functional significance of this let-7 reactivation, exogenous mimetics of the let-7c and let-7d family members were transfected into human PDAC cells, and they specifically inhibited the growth of the SIRT6$^{low}$ cell lines BxPc3 and Panc-1 without any significant effect on the growth of the SIRT6$^{high}$ cell line COLO357. We also obtained a miRNA which mimics let-7g, but has been mutated so that it is unable to be bound and degraded by Lin28b (Piskounova et al., 2008). Ectopic expression of this let-7g mimetic (7S21L) potently inhibited both proliferation and tumor sphere forming ability of SIRT6$^{low}$ PDAC cell lines. Importantly, growth inhibition following ectopic expression of let-7 mimetics was also accompanied by a reduction in the expression of let-7 target genes, IGF2BP1, IGF2BP3, and HMGA2 as well as LIN28B, which is also directly inhibited by let-7 as a part of a feedback loop (Rybak et al., 2008). Thus, multiple let-7 family members potently and selectively inhibit the growth of SIRT6$^{low}$ PDAC cells, potentially through the suppression of let-7 target genes.

Figure 6A:
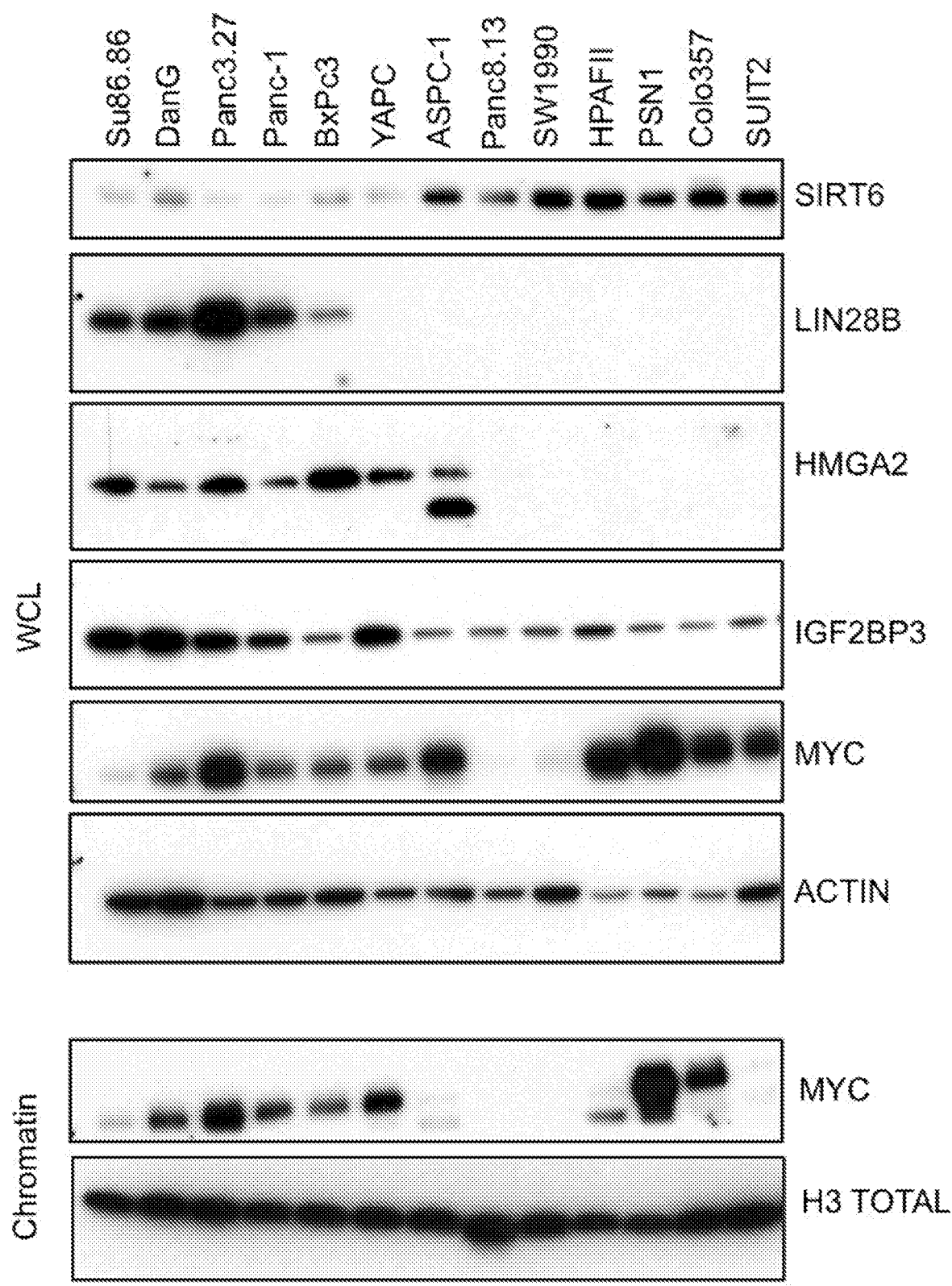
Figure 6B:
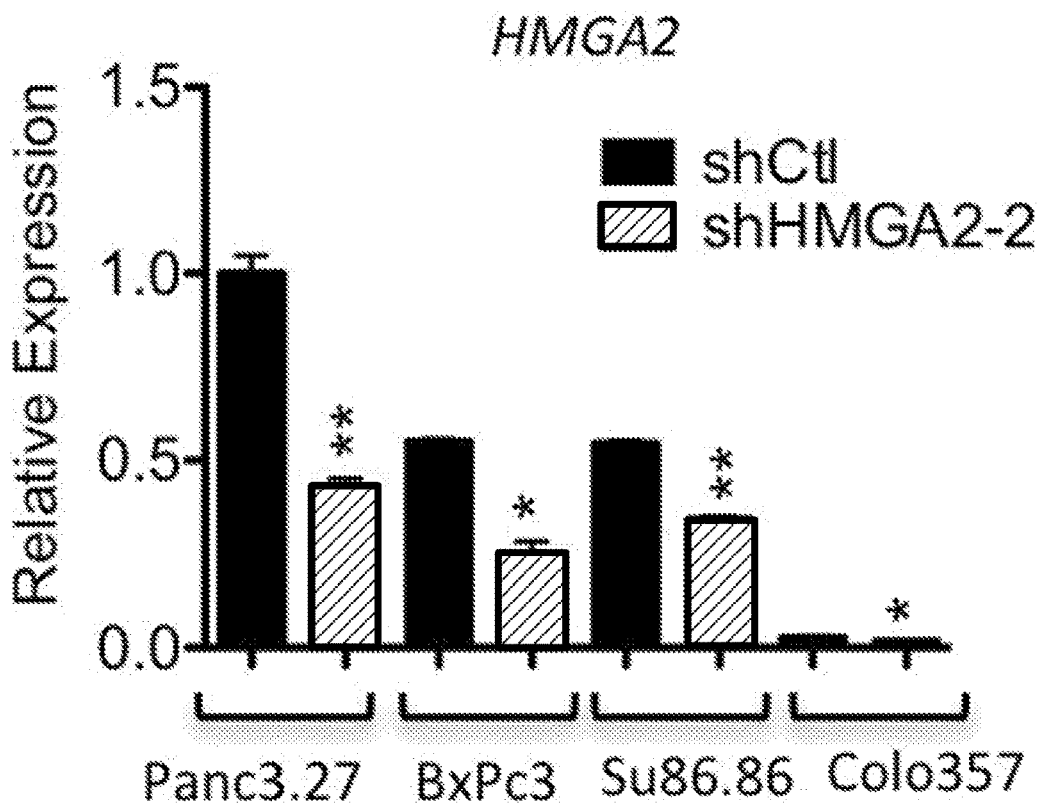
Figure 6C:
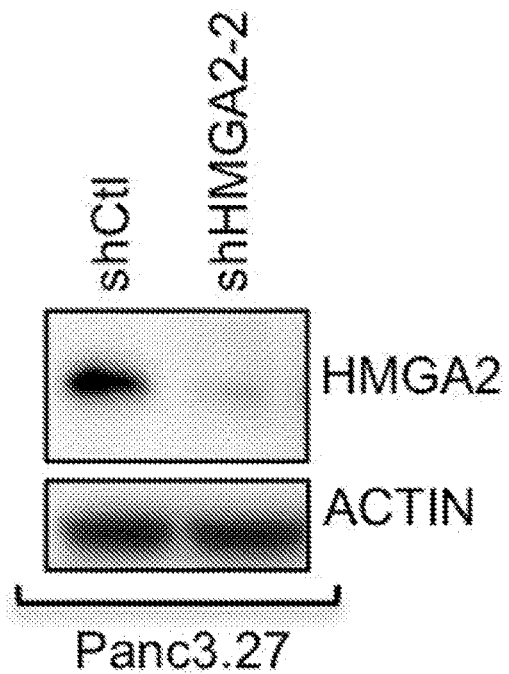
Figure 6D:
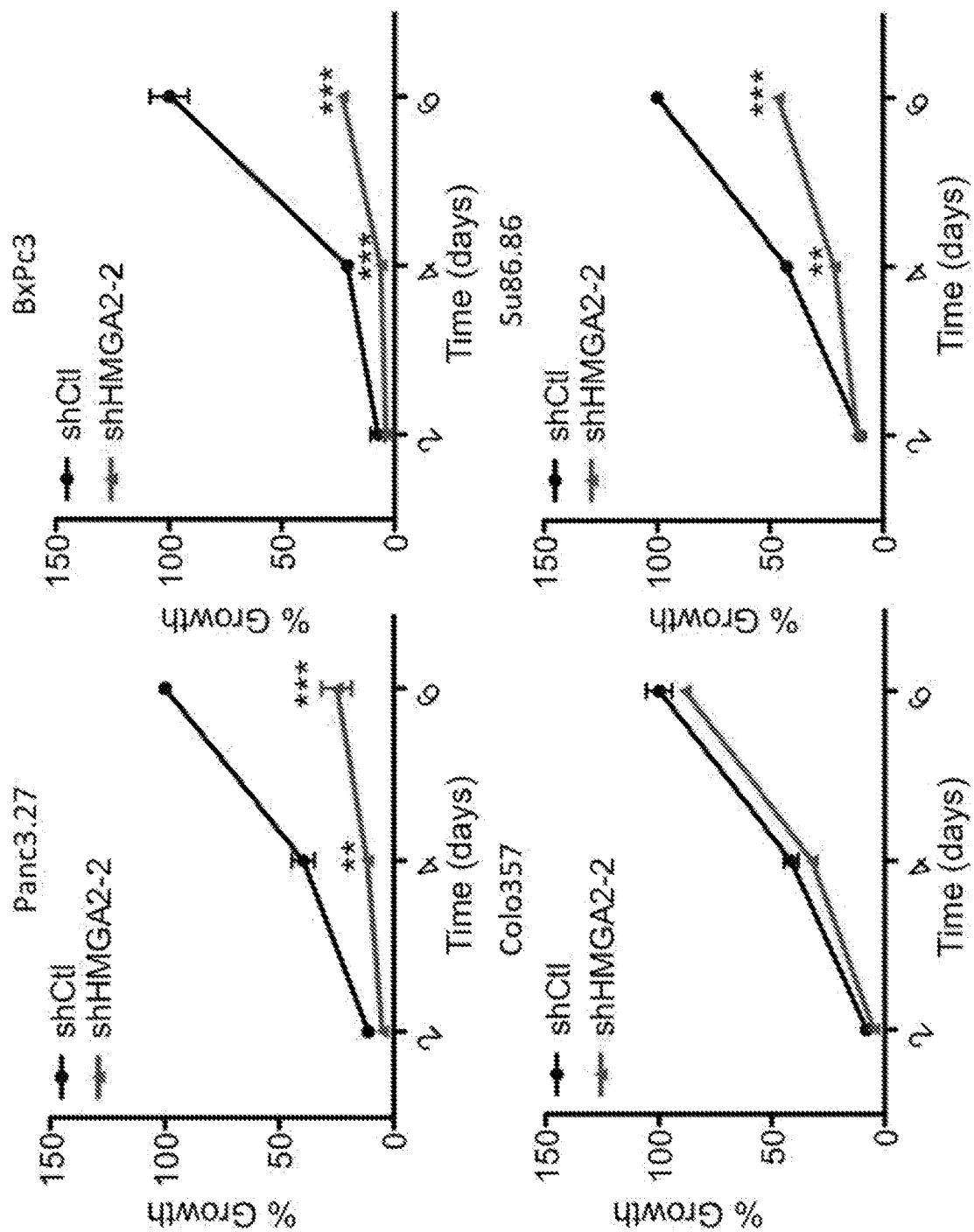
Figure 6E:
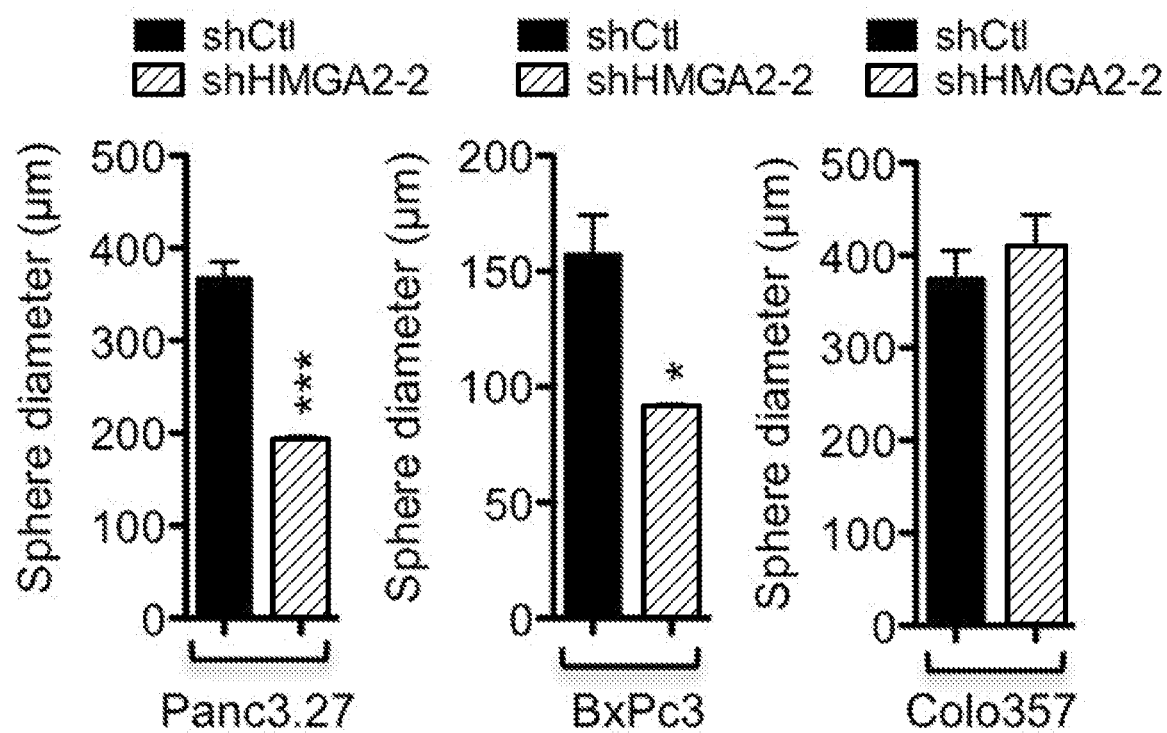
Figure 6E:
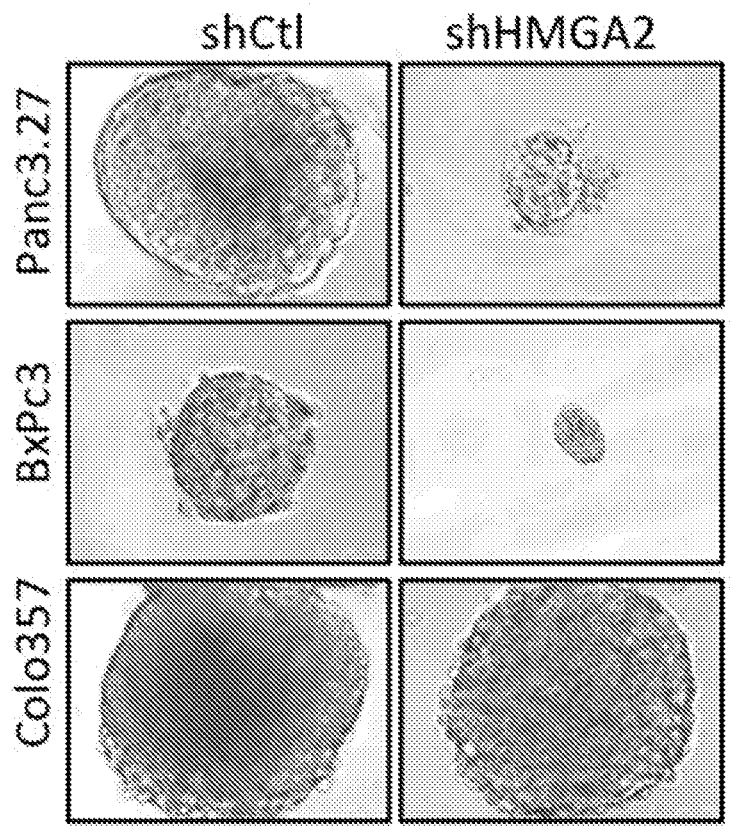
Figure 6F:
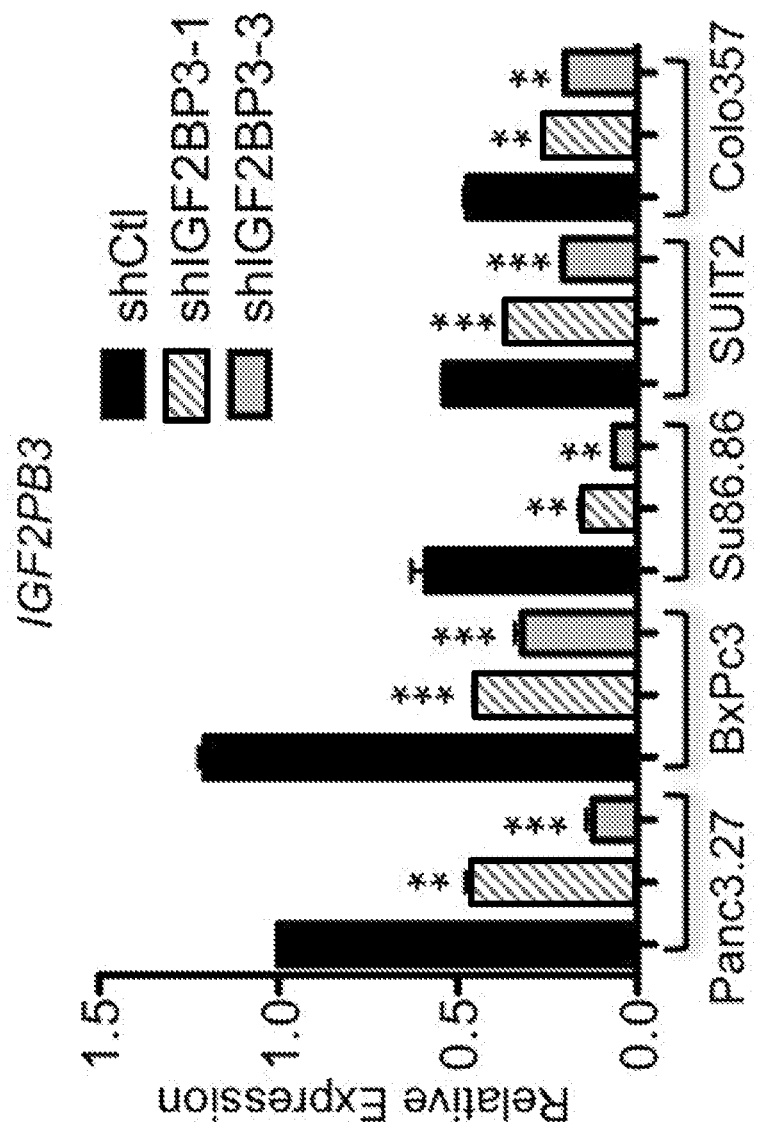
Figure 6G:
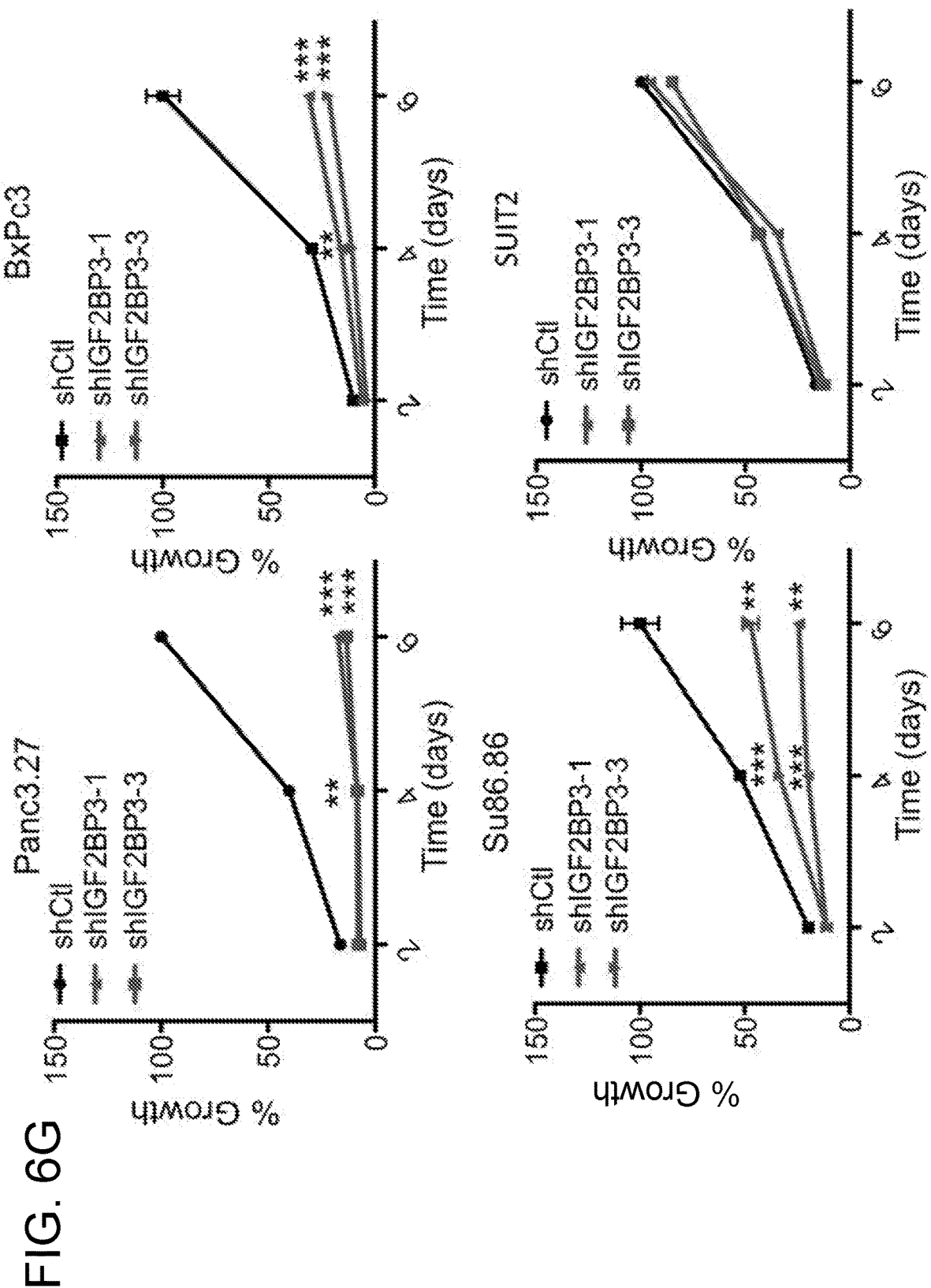
Figure 6H:
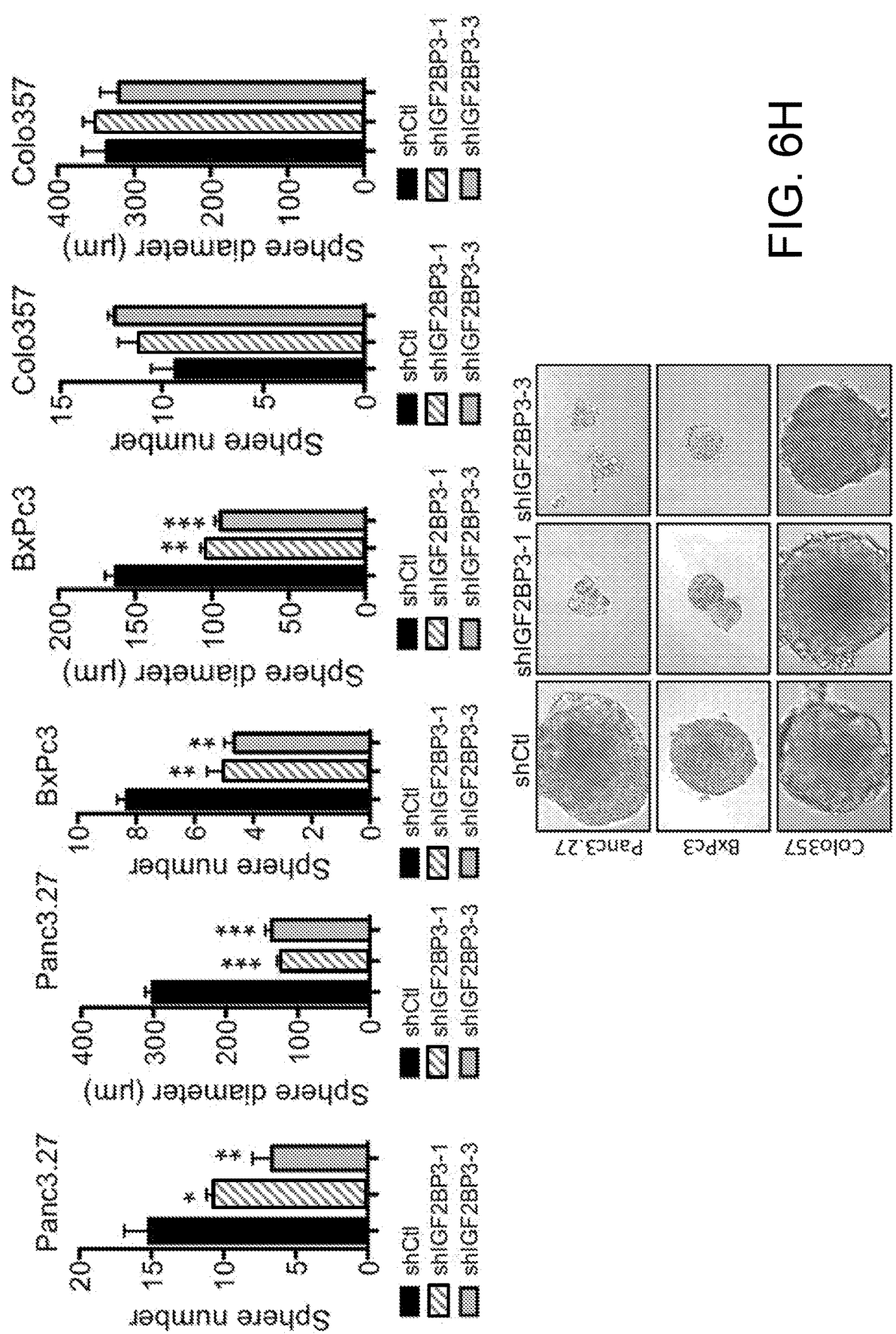

Example 7: SIRT6$^{low}$ PDAC are Dependent on let-7 Target Genes for Growth Interestingly, high expression of Igf2bp1 and Igf2bp3, which are both directly inhibited by let-7, is correlated with increased aggressiveness and metastasis in pancreatic tumors (Thakur et al., 2008; Yantiss et al., 2005), and in support of a causal role in transformation, transgenic overexpression of mouse Igf2bp3 (IMP3/KOC) leads to increased cell proliferation and metaplasia of pancreatic acinar cells (Wagner et al., 2003). Both Igf2bp1 and Igf2bp3 were highly upregulated in our SIRT6 KO cells relative to SIRT6 WT cells and in our human SIRT6$^{low}$ PDAC cells (FIG. 6A). In addition, HMGA2 is another let-7 target gene that is associated with advanced tumor grade and lymph node metastasis in PDAC (Piscuoglio et al., 2012) and, strikingly, was universally expressed in SIRT6$^{low}$ lines, but almost completely absent in all SIRT6$^{high}$ lines analyzed (FIG. 6A). Restoration of WT but not catalytically inactive SIRT6 in SIRT6 KO murine and SIRT6$^{low}$ human PDAC cells reduced expression of both Lin28b and let-7 target genes, confirming the direct role of SIRT6 in regulating this pathway. While these findings are consistent with a model whereby SIRT6 acts upstream of the Lin28b/let-7 axis to suppress Lin28b expression, enhance let-7 levels and inhibit expression of let-7 target genes, the functional role of each of these let-7 target genes in driving the growth of PDAC cells has not yet been clearly established. Therefore, either HMGA2 or IGF2BP3 was knocked down in a panel of human PDAC cell lines. Remarkably, although the Lin28b/let-7 pathway has many known targets, knock-down of either HMGA2, IGF2BP1, or IGF2BP3 was sufficient to inhibit both proliferation and tumor sphere formation in SIRT6$^{low}$ PDAC cells without any discernable effect on SIRT6$^{high}$ PDAC cells (FIGS. 6B-H). Further, knock-down of Igf2bp3 with siRNA specifically slowed growth of SIRT6 KO cells but had no effect on SIRT6 WT murine PDAC cells. Thus, multiple let-7 target genes may cooperate to drive the growth of SIRT6$^{low}$ PDAC.

Example 8: Increased Expression of LIN28B and let-7 Target Genes Correlates with Poor Survival in PDAC These observations prompted us to investigate the relevance of this pathway to the human disease. As shown previously, loss of SIRT6 expression in human PDAC tumors defined a subset of patients with a worse prognosis (FIG. 1B). Strikingly, elevated expression of LIN28B also correlated with poor prognosis in our same cohort of 120 patient samples (FIG. 7A). Moreover, gene set enrichment analysis (GSEA) comparing PDAC tumors (Badea et al., 2008; Biankin et al., 2012; Pei et al., 2009; Perez-Mancera et al., 2012; Zhang et al., 2012) and cell lines (Barretina et al., 2012) with high versus low expression of LIN28B revealed that LIN28B$^{high}$ tumors were strongly enriched for the expression of Myc targets, as well as for let-7 targets, curated in three independent gene sets (FIG. 7B). This finding was further validated in the CCLE dataset (FIG. 7C). More specifically, the oncofetal targets of let-7, which includes the IGF2BPs and HMGA2, were upregulated in LIN28B$^{high}$ tumors in three independent datasets (FIG. 7D). Accordingly, loss of let-7 expression, as measured by in-situ hybridization (ISH) for let-7a, also corresponded to a shorter overall survival. Finally, expression of these oncofetal targets IGF2BP3 and HMGA2 correlated both with each other and a worse prognosis in the cancer genome atlas (TCGA) dataset (FIGS. 7E and 7F). Taken together, our findings are consistent with a model whereby loss of SIRT6 in PDAC allows for aberrant hyperacetylation of the Lin28b promoter, enhancing Myc-driven transcription of Lin28b, which then inhibits the let-7 family of miRNA. This allows for the reactivation of let-7 target genes such as HMGA2 and IGF2BPs, which serve to drive the growth and survival of a highly aggressive form of pancreatic cancer (FIG. 7G).

REFERENCES

Aaltonen, L. A., Hamilton, S. R., World Health Organization and International Agency for Research on Cancer. (2000). Pathology and genetics of tumours of the digestive system (Lyon Oxford: IARC Press; Oxford University Press).

Badea, L., Herlea, V., Dima, S. O., Dumitrascu, T., and Popescu, I. (2008). Combined gene expression analysis of whole-tissue and microdissected pancreatic ductal adenocarcinoma identifies genes specifically overexpressed in tumor epithelia. Hepato-gastroenterology 55, 2016-2027.

Barretina, J., Caponigro, G., Stransky, N., Venkatesan, K., Margolin, A. A., Kim, S., Wilson, C. J., Lehar, J., Kryukov, G. V., Sonkin, D., et al. (2012). The Cancer Cell Line Encyclopedia enables predictive modelling of anticancer drug sensitivity. Nature 483, 603-607.

Bell, J. L., Wachter, K., Muhleck, B., Pazaitis, N., Kohn, M., Lederer, M., and Huttelmaier, S. (2013). Insulin-like growth factor 2 mRNA-binding proteins (IGF2BPs): post-transcriptional drivers of cancer progression? Cellular and molecular life sciences: CMLS 70, 2657-2675.

Biankin, A. V., Waddell, N., Kassahn, K. S., Gingras, M. C., Muthuswamy, L. B., Johns, A. L., Miller, D. K., Wilson, P. J., Patch, A. M., Wu, J., et al. (2012). Pancreatic cancer genomes reveal aberrations in axon guidance pathway genes. Nature 491, 399-405.

Boyerinas, B., Park, S. M., Shomron, N., Hedegaard, M. M., Vinther, J., Andersen, J. S., Feig, C., Xu, J., Burge, C. B., and Peter, M. E. (2008). Identification of let-7-regulated oncofetal genes. Cancer research 68, 2587-2591.

Bussing, I., Slack, F. J., and Grosshans, H. (2008). let-7 microRNAs in development, stem cells and cancer. Trends in molecular medicine 14, 400-409.

Chang, T. C., Zeitels, L. R., Hwang, H. W., Chivukula, R. R., Wentzel, E. A., Dews, M., Jung, J., Gao, P., Dang, C. V., Beer, M. A., et al. (2009). Lin-28B transactivation is necessary for Myc-mediated let-7 repression and proliferation. Proceedings of the National Academy of Sciences of the United States of America 106, 3384-3389.

de Vries, N. A., Hulsman, D., Akhtar, W., de Jong, J., Miles, D. C., Blom, M., van Tellingen, O., Jonkers, J., and van Lohuizen, M. (2015). Prolonged Ezh2 Depletion in Glioblastoma Causes a Robust Switch in Cell Fate Resulting in Tumor Progression. Cell reports.

Donner, A. J., Szostek, S., Hoover, J. M., and Espinosa, J. M. (2007). CDK8 is a stimulus-specific positive coregulator of p53 target genes. Molecular cell 27, 121-133.

Etchegaray, J. P., Chavez, L., Huang, Y., Ross, K. N., Choi, J., Martinez-Pastor, B., Walsh, R. M., Sommer, C. A., Lienhard, M., Gladden, A., et al. (2015). The histone deacetylase SIRT6 controls embryonic stem cell fate via TET-mediated production of 5-hydroxymethylcytosine. Nature cell biology 17, 545-557.

Fitamant, J., Kottakis, F., Benhamouche, S., Tian, H. S., Chuvin, N., Parachoniak, C. A., Nagle, J. M., Perera, R. M., Lapouge, M., Deshpande, V., et al. (2015). YAP Inhibition Restores Hepatocyte Differentiation in Advanced HCC, Leading to Tumor Regression. Cell reports.

Funato, K., Major, T., Lewis, P. W., Allis, C. D., and Tabar, V. (2014). Use of human embryonic stem cells to model pediatric gliomas with H3.3K27M histone mutation. Science 346, 1529-1533.

Furukawa, T., Duguid, W. P., Rosenberg, L., Viallet, J., Galloway, D. A., and Tsao, M. S. (1996). Long-term culture and immortalization of epithelial cells from normal adult human pancreatic ducts transfected by the E6E7 gene of human papilloma virus 16. The American journal of pathology 148, 1763-1770.

Heo, I., Joo, C., Cho, J., Ha, M., Han, J., and Kim, V. N. (2008). Lin28 mediates the terminal uridylation of let-7 precursor MicroRNA. Molecular cell 32, 276-284.

Iliopoulos, D., Hirsch, H. A., and Struhl, K. (2009). An epigenetic switch involving NF-kappaB, Lin28, Let-7 MicroRNA, and IL6 links inflammation to cell transformation. Cell 139, 693-706.

Jackson, E. L., Willis, N., Mercer, K., Bronson, R. T., Crowley, D., Montoya, R., Jacks, T., and Tuveson, D. A. (2001). Analysis of lung tumor initiation and progression using conditional expression of oncogenic K-ras. Genes & development 15, 3243-3248.

Johnson, S. M., Grosshans, H., Shingara, J., Byrom, M., Jarvis, R., Cheng, A., Labourier, E., Reinert, K. L., Brown, D., and Slack, F. J. (2005). RAS is regulated by the let-7 microRNA family. Cell 120, 635-647.

Kawaguchi, Y., Cooper, B., Gannon, M., Ray, M., MacDonald, R. J., and Wright, C. V. (2002). The role of the transcriptional regulator Ptf1a in converting intestinal to pancreatic progenitors. Nature genetics 32, 128-134.

King, C. E., Cuatrecasas, M., Castells, A., Sepulveda, A. R., Lee, J. S., and Rustgi, A. K. (2011). LIN28B promotes colon cancer progression and metastasis. Cancer research 71, 4260-4268.

Kugel, S., Feldman, J. L., Klein, M. A., Silberman, D. M., Sebastian, C., Mermel, C., Dobersch, S., Clark, A. R., Getz, G., Denu, J. M., et al. (2015). Identification of and Molecular Basis for SIRT6 Loss-of-Function Point Mutations in Cancer. Cell reports.

Lei, X. X., Xu J., Ma, W., Qiao, C., Newman, M. A., Hammond, S. M., and Huang, Y. (2012). Determinants of mRNA recognition and translation regulation by Lin28. Nucleic Acids Res. 40, 3574-84

Li, H., and Durbin, R. (2009). Fast and accurate short read alignment with Burrows-Wheeler transform. Bioinformatics 25, 1754-1760.

Liang, K., and Keles, S. (2012). Detecting differential binding of transcription factors with ChIP-seq. Bioinformatics 28, 121-122.

Lu, L., Katsaros, D., Shaverdashvili, K., Qian, B., Wu, Y., de la Longrais, I. A., Preti, M., Menato, G., and Yu, H. (2009). Pluripotent factor lin-28 and its homologue lin-28b in epithelial ovarian cancer and their associations with disease outcomes and expression of let-7a and IGF-II. European Journal of Cancer 45, 2212-2218.

Marino, S., Vooijs, M., van Der Gulden, H., Jonkers, J., and Berns, A. (2000). Induction of medulloblastomas in p53-null mutant mice by somatic inactivation of Rb in the external granular layer cells of the cerebellum. Genes & development 14, 994-1004.

Mayr, C., Hemann, M. T., and Bartel, D. P. (2007). Disrupting the pairing between let-7 and Hmga2 enhances oncogenic transformation. Science 315, 1576-1579.

Mootha, V. K., Lindgren, C. M., Eriksson, K. F., Subramanian, A., Sihag, S., Lehar, J., Puigserver, P., Carlsson, E., Ridderstrale, M., Laurila, E., et al. (2003). PGC-1 alpha-responsive genes involved in oxidative phosphorylation are coordinately downregulated in human diabetes. Nature genetics 34, 267-273.

Moss, E. G., and Tang, L. (2003). Conservation of the heterochronic regulator Lin-28, its developmental expression and microRNA complementary sites. Developmental biology 258, 432-442.

Mostoslaysky, R., Chua, K. F., Lombard, D. B., Pang, W. W., Fischer, M. R., Gellon, L., Liu, P., Mostoslaysky, G., Franco, S., Murphy, M. M., et al. (2006). Genomic instability and aging-like phenotype in the absence of mammalian SIRT6. Cell 124, 315-329.

Newman, M. A., Thomson, J. M., and Hammond, S. M. (2008). Lin-28 interaction with the Let-7 precursor loop mediates regulated microRNA processing. Rna 14, 1539-1549.

Nguyen, L. H., Robinton, D. A., Seligson, M. T., Wu, L., Li, L., Rakheja, D., Comerford, S. A., Ramezani, S., Sun, X., Parikh, M. S., et al. (2014). Lin28b is sufficient to drive liver cancer and necessary for its maintenance in murine models. Cancer cell 26, 248-261.

Nielsen, J., Kristensen, M. A., Willemoes, M., Nielsen, F. C., and Christiansen, J. (2004). Sequential dimerization of human zipcode-binding protein IMP1 on RNA: a cooperative mechanism providing RNP stability. Nucleic acids research 32, 4368-4376.

Noubissi, F. K., Elcheva, I., Bhatia, N., Shakoori, A., Ougolkov, A., Liu, J., Minamoto, T., Ross, J., Fuchs, S. Y., and Spiegelman, V. S. (2006). CRD-BP mediates stabilization of betaTrCP1 and c-myc mRNA in response to beta-catenin signalling. Nature 441, 898-901.

Park, S. M., Shell, S., Radjabi, A. R., Schickel, R., Feig, C., Boyerinas, B., Dinulescu, D. M., Lengyel, E., and Peter, M. E. (2007). Let-7 prevents early cancer progression by suppressing expression of the embryonic gene HMGA2. Cell cycle 6, 2585-2590.

Pasquinelli, A. E., Reinhart, B. J., Slack, F., Martindale, M. Q., Kuroda, M. I., Maller, B., Hayward, D. C., Ball, E. E., Degnan, B., Muller, P., et al. (2000). Conservation of the sequence and temporal expression of let-7 heterochronic regulatory RNA. Nature 408, 86-89.

Pei, H., Li, L., Fridley, B. L., Jenkins, G. D., Kalari, K. R., Lingle, W., Petersen, G., Lou, Z., and Wang, L. (2009). FKBP51 affects cancer cell response to chemotherapy by negatively regulating Akt. Cancer cell 16, 259-266.

Perez-Mancera, P. A., Rust, A. G., van der Weyden, L., Kristiansen, G., Li, A., Sarver, A. L., Silverstein, K. A., Grutzmann, R., Aust, D., Rummele, P., et al. (2012). The deubiquitinase USP9X suppresses pancreatic ductal adenocarcinoma. Nature 486, 266-270.

Piscuoglio, S., Zlobec, I., Pallante, P., Sepe, R., Esposito, F., Zimmermann, A., Diamantis, I., Terracciano, L., Fusco, A., and Karamitopoulou, E. (2012). HMGA1 and HMGA2 protein expression correlates with advanced tumour grade and lymph node metastasis in pancreatic adenocarcinoma. Histopathology 60, 397-404.

Piskounova, E., Viswanathan, S. R., Janas, M., LaPierre, R. J., Daley, G. Q., Sliz, P., and Gregory, R. I. (2008). Determinants of microRNA processing inhibition by the developmentally regulated RNA-binding protein Lin28. The Journal of biological chemistry 283, 21310-21314.

Polesskaya, A., Cuvellier, S., Naguibneva, I., Duquet, A., Moss, E. G., and Harel-Bellan, A. (2007). Lin-28 binds IGF-2 mRNA and participates in skeletal myogenesis by increasing translation efficiency. Genes & development 21, 1125-1138.

Robinson, M. D., McCarthy, D. J., and Smyth, G. K. (2010). edgeR: a Bioconductor package for differential expression analysis of digital gene expression data. Bioinformatics 26, 139-140.

Ryan, D. P., Hong, T. S., and Bardeesy, N. (2014). Pancreatic adenocarcinoma. The New England journal of medicine 371, 1039-1049.

Rybak, A., Fuchs, H., Smirnova, L., Brandt, C., Pohl, E. E., Nitsch, R., and Wulczyn, F. G. (2008). A feedback loop comprising lin-28 and let-7 controls pre-let-7 maturation during neural stem-cell commitment. Nature cell biology 10, 987-993.

Sampson, V. B., Rong, N. H., Han, J., Yang, Q., Aris, V., Soteropoulos, P., Petrelli, N. J., Dunn, S. P., and Krueger, L. J. (2007). MicroRNA let-7a down-regulates MYC and reverts MYC-induced growth in Burkitt lymphoma cells. Cancer research 67, 9762-9770.

Schaeffer, D. F., Owen, D. R., Lim, H. J., Buczkowski, A. K., Chung, S. W., Scudamore, C. H., Huntsman, D. G., Ng, S. S., and Owen, D. A. (2010). Insulin-like growth factor 2 mRNA binding protein 3 (IGF2BP3) overexpression in pancreatic ductal adenocarcinoma correlates with poor survival. BMC cancer 10, 59.

Sebastian, C., Zwaans, B. M., Silberman, D. M., Gymrek, M., Goren, A., Zhong, L., Ram, O., Truelove, J., Guimaraes, A. R., Toiber, D., et al. (2012). The histone deacetylase SIRT6 is a tumor suppressor that controls cancer metabolism. Cell 151, 1185-1199.

Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: a knowledge-based approach for interpreting genome-wide expression profiles. Proceedings of the National Academy of Sciences of the United States of America 102, 15545-15550.

Taniuchi, K., Furihata, M., Hanazaki, K., Saito, M., and Saibara, T. (2014). IGF2BP3-mediated translation in cell protrusions promotes cell invasiveness and metastasis of pancreatic cancer. Oncotarget 5, 6832-6845.

Thakur, A., Bollig, A., Wu, J., and Liao, D. J. (2008). Gene expression profiles in primary pancreatic tumors and metastatic lesions of Ela-c-myc transgenic mice. Molecular cancer 7, 11.

Thornton, J. E., and Gregory, R. I. (2012). How does Lin28 let-7 control development and disease? Trends in cell biology 22, 474-482.

Viswanathan, S. R., and Daley, G. Q. (2010). Lin28: A microRNA regulator with a macro role. Cell 140, 445-449.

Viswanathan, S. R., Daley, G. Q., and Gregory, R. I. (2008). Selective blockade of microRNA processing by Lin28. Science 320, 97-100.

Viswanathan, S. R., Powers, J. T., Einhorn, W., Hoshida, Y., Ng, T. L., Toffanin, S., O'Sullivan, M., Lu, J., Phillips, L. A., Lockhart, V. L., et al. (2009). Lin28 promotes transformation and is associated with advanced human malignancies. Nature genetics 41, 843-848.

Waddell, N., Pajic, M., Patch, A. M., Chang, D. K., Kassahn, K. S., Bailey, P., Johns, A. L., Miller, D., Nones, K., Quek, K., et al. (2015). Whole genomes redefine the mutational landscape of pancreatic cancer. Nature 518, 495-501.

Wagner, M., Kunsch, S., Duerschmied, D., Beil, M., Adler, G., Mueller, F., and Gress, T. M. (2003). Transgenic overexpression of the oncofetal RNA binding protein KOC leads to remodeling of the exocrine pancreas. Gastroenterology 124, 1901-1914.

Wang, W. C., Lin, F. M., Chang, W. C., Lin, K. Y., Huang, H. D., and Lin, N. S. (2009). miRExpress: analyzing high-throughput sequencing data for profiling microRNA expression. BMC bioinformatics 10, 328.

Yang, D. H., and Moss, E. G. (2003). Temporally regulated expression of Lin-28 in diverse tissues of the developing mouse. Gene expression patterns: GEP 3, 719-726.

Yantiss, R. K., Woda, B. A., Fanger, G. R., Kalos, M., Whalen, G. F., Tada, H., Andersen, D. K., Rock, K. L., and Dresser, K. (2005). KOC (K homology domain containing protein overexpressed in cancer): a novel molecular marker that distinguishes between benign and malignant lesions of the pancreas. The American journal of surgical pathology 29, 188-195.

Ying, H., Kimmelman, A. C., Lyssiotis, C. A., Hua, S., Chu, G. C., Fletcher-Sananikone, E., Locasale, J. W., Son, J., Zhang, H., Coloff, J. L., et al. (2012). Oncogenic Kras maintains pancreatic tumors through regulation of anabolic glucose metabolism. Cell 149, 656-670.

Zhang, G., Schetter, A., He, P., Funamizu, N., Gaedcke, J., Ghadimi, B. M., Ried, T., Hassan, R., Yfantis, H. G., Lee, D. H., et al. (2012). DPEP1 inhibits tumor cell invasiveness, enhances chemosensitivity and predicts clinical outcome in pancreatic ductal adenocarcinoma. PloS one 7, e31507.

Zhang, Y., Liu, T., Meyer, C. A., Eeckhoute, J., Johnson, D. S., Bernstein, B. E., Nusbaum, C., Myers, R. M., Brown, M., Li, W., et al. (2008). Model-based analysis of ChIP-Seq (MACS). Genome biology 9, R137.

Zhong, L., D'Urso, A., Toiber, D., Sebastian, C., Henry, R. E., Vadysirisack, D. D., Guimaraes, A., Marinelli, B., Wikstrom, J. D., Nir, T., et al. (2010). The histone deacetylase Sirt6 regulates glucose homeostasis via Hif1 alpha. Cell 140, 280-293.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating PDAC in a subject, the method comprising:
providing a sample comprising pancreatic cells from the subject;
performing an assay to determine a level of SIRT6 expression in the sample;
comparing the level of SIRT6 expression in the sample to a reference level of SIRT6 expression; and
administering a therapeutically effective amount of a Lin28b inhibitor to a subject who has a level of SIRT6 expression in the sample below the reference level, wherein the Lin28b inhibitor comprises an inhibitory nucleic acid effective to specifically reduce expression of Lin28b, thereby treating PDAC in the subject.

2. The method of claim 1, wherein the inhibitory nucleic acid is a small interfering RNA molecule, antisense nucleic acid, LNA molecule, PNA molecule, or ribozyme.

3. The method of claim 1, wherein the inhibitory nucleic acid comprises a sequence of 5'-GCCTTGAGT-CAATACGGGTAA-3' (SEQ ID NO:3).

4. The method of claim 1, wherein the subject is a mammal.

5. The method of claim 1, wherein the subject is a human.

6. A method of diagnosing and treating PDAC in a subject, the method comprising:
providing a sample comprising pancreatic cells from the subject;
performing an assay to determine a level of Lin28b and SIRT6 expression in the sample;
comparing the levels of Lin28b and SIRT6 expression in the sample to reference levels of Lin28b and SIRT6 expression;
identifying a subject who has a level of Lin28b and SIRT6 expression in the sample above the reference level as having PDAC or having an increased risk of developing PDAC; and
administering a treatment for PDAC to the identified subject who has a level of Lin28b and SIRT6 expression in the sample that is above the reference level, wherein the treatment comprises an inhibitory nucleic acid effective to specifically reduce expression of Lin28b.

7. The method of claim 6, wherein the inhibitory nucleic acid is a small interfering RNA molecule, antisense nucleic acid, LNA molecule, PNA molecule, or ribozyme.

8. The method of claim 6, wherein the inhibitory nucleic acid comprises a sequence of 5'-GCCTTGAGT-CAATACGGGTAA-3' (SEQ ID NO:3).

9. The method of claim 6, wherein the level of Lin28b expression in the sample is determined by quantitative PCR, flow cytometry, or quantitative immunoassay.

10. The method of claim 6, wherein the subject is a mammal.

11. The method of claim 6, wherein the subject is a human.

* * * * *

UNITED STATES PATENT AND TRADEMARK OFFICE
CERTIFICATE OF CORRECTION

PATENT NO. : 10,588,920 B2
APPLICATION NO. : 15/563248
DATED : March 17, 2020
INVENTOR(S) : Raul Mostoslavsky, Sita Kugel and Anders M. Naar Page 1 of 1

It is certified that error appears in the above-identified patent and that said Letters Patent is hereby corrected as shown below:

In the Specification

In Column 1, Line 14, insert -- STATEMENT OF FEDERALLY SPONSORED RESEARCH
This invention was made with government support under Grant No. W81XWH-17-1-0517 awarded
by the Defense Advanced Research Projects Agency, and CA198109 awarded by the National
Institutes of Health. The government has certain rights in the invention. --

Signed and Sealed this
Twenty-third Day of May, 2023

Katherine Kelly Vidal
*Director of the United States Patent and Trademark Office*

SEQUENCE LISTING

```
<160> NUMBER OF SEQ ID NOS: 15

<210> SEQ ID NO 1
<211> LENGTH: 31
<212> TYPE: DNA
<213> ORGANISM: Artificial Sequence
<220> FEATURE:
<223> OTHER INFORMATION: laboratory-synthesized sequence

<400> SEQUENCE: 1
```

```
caggatcctt gttcccgtgg ggcagtcgag g                                    31

<210> SEQ ID NO 2
<211> LENGTH: 30
<212> TYPE: DNA
<213> ORGANISM: Artificial Sequence
<220> FEATURE:
<223> OTHER INFORMATION: laboratory-synthesized sequence

<400> SEQUENCE: 2
cagaattcct acaaaaagcc ccaccctccc                                      30

<210> SEQ ID NO 3
<211> LENGTH: 21
<212> TYPE: DNA
<213> ORGANISM: Artificial Sequence
<220> FEATURE:
<223> OTHER INFORMATION: laboratory-synthesized sequence

<400> SEQUENCE: 3
gccttgagtc aatacgggta a                                               21

<210> SEQ ID NO 4
<211> LENGTH: 21
<212> TYPE: DNA
<213> ORGANISM: Artificial Sequence
<220> FEATURE:
<223> OTHER INFORMATION: laboratory-synthesized sequence

<400> SEQUENCE: 4
gccacaacaa gttgttcaga a                                               21

<210> SEQ ID NO 5
<211> LENGTH: 21
<212> TYPE: DNA
<213> ORGANISM: Artificial Sequence
<220> FEATURE:
<223> OTHER INFORMATION: laboratory-synthesized sequence

<400> SEQUENCE: 5
cccaaggtag ttatccttaa a                                               21

<210> SEQ ID NO 6
<211> LENGTH: 21
<212> TYPE: DNA
<213> ORGANISM: Artificial Sequence
<220> FEATURE:
<223> OTHER INFORMATION: laboratory-synthesized sequence

<400> SEQUENCE: 6
cctgagacag atcagcaaca a                                               21

<210> SEQ ID NO 7
<211> LENGTH: 21
<212> TYPE: DNA
<213> ORGANISM: Artificial Sequence
<220> FEATURE:
<223> OTHER INFORMATION: laboratory-synthesized sequence

<400> SEQUENCE: 7
gcctcattct tatttcaaga t                                               21

<210> SEQ ID NO 8
<211> LENGTH: 21
<212> TYPE: DNA
<213> ORGANISM: Artificial Sequence
```

```
<220> FEATURE:
<223> OTHER INFORMATION: laboratory-synthesized sequence

<400> SEQUENCE: 8
cggtgaatga acttcagaat t                                              21

<210> SEQ ID NO 9
<211> LENGTH: 21
<212> TYPE: DNA
<213> ORGANISM: Artificial Sequence
<220> FEATURE:
<223> OTHER INFORMATION: laboratory-synthesized sequence

<400> SEQUENCE: 9
gcagtggtga atgtcaccta t                                              21

<210> SEQ ID NO 10
<211> LENGTH: 21
<212> TYPE: DNA
<213> ORGANISM: Artificial Sequence
<220> FEATURE:
<223> OTHER INFORMATION: laboratory-synthesized sequence

<400> SEQUENCE: 10
cctggcccat aataactttg t                                              21

<210> SEQ ID NO 11
<211> LENGTH: 21
<212> TYPE: DNA
<213> ORGANISM: Artificial Sequence
<220> FEATURE:
<223> OTHER INFORMATION: laboratory-synthesized sequence

<400> SEQUENCE: 11
gctgagtatt tctttcaagt t                                              21

<210> SEQ ID NO 12
<211> LENGTH: 21
<212> TYPE: DNA
<213> ORGANISM: Artificial Sequence
<220> FEATURE:
<223> OTHER INFORMATION: laboratory-synthesized sequence

<400> SEQUENCE: 12
cgtgaacatc ttcaagttca t                                              21

<210> SEQ ID NO 13
<211> LENGTH: 21
<212> TYPE: DNA
<213> ORGANISM: Artificial Sequence
<220> FEATURE:
<223> OTHER INFORMATION: laboratory-synthesized sequence

<400> SEQUENCE: 13
cgtctccctg aagtctctta a                                              21

<210> SEQ ID NO 14
<211> LENGTH: 21
<212> TYPE: DNA
<213> ORGANISM: Artificial Sequence
<220> FEATURE:
<223> OTHER INFORMATION: laboratory-synthesized sequence

<400> SEQUENCE: 14
gcctacatcc tgtccattca a                                              21
```

```
<210> SEQ ID NO 15
<211> LENGTH: 22
<212> TYPE: DNA
<213> ORGANISM: Artificial Sequence
<220> FEATURE:
<223> OTHER INFORMATION: laboratory-synthesized sequence

<400> SEQUENCE: 15
gcaagctgac cctgaagttc at                                              22
```